(12) United States Patent
Mecozzi et al.

(10) Patent No.: US 9,000,048 B2
(45) Date of Patent: Apr. 7, 2015

(54) FLUOROPOLYMER-BASED EMULSIONS FOR THE INTRAVENOUS DELIVERY OF FLUORINATED VOLATILE ANESTHETICS

(75) Inventors: Sandro Mecozzi, Madison, WI (US);
Robert A. Pearce, Madison, WI (US);
Jonathan P. Fast, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1239 days.

(21) Appl. No.: 11/946,174

(22) Filed: Nov. 28, 2007

(65) Prior Publication Data

US 2008/0234389 A1     Sep. 25, 2008

Related U.S. Application Data

(60) Provisional application No. 60/867,432, filed on Nov. 28, 2006.

(51) Int. Cl.
| A61K 31/08 | (2006.01) |
| A61K 9/00 | (2006.01) |
| A61K 9/107 | (2006.01) |
| A61K 47/34 | (2006.01) |

(52) U.S. Cl.
CPC ............ *A61K 9/0019* (2013.01); *A61K 9/1075* (2013.01); *A61K 31/08* (2013.01); *A61K 47/34* (2013.01)

(58) Field of Classification Search
None
See application file for complete search history.

(56) References Cited

U.S. PATENT DOCUMENTS

| 5,733,526 A | 3/1998 | Trevino et al. |
| 5,914,352 A | 6/1999 | Weers et al. |
| 5,929,177 A | 7/1999 | Kataoka et al. |
| 6,113,919 A | 9/2000 | Reiss et al. |
| 6,316,505 B1 | 11/2001 | Kabanov et al. |
| 6,322,805 B1 | 11/2001 | Kim et al. |
| 6,444,660 B1 | 9/2002 | Unger et al. |
| 6,808,720 B2 | 10/2004 | Unger |
| 6,864,386 B1 | 3/2005 | Zhang et al. |
| 6,903,173 B2 | 6/2005 | Cernohous et al. |
| 7,018,655 B2 | 3/2006 | Lele et al. |
| 2004/0116360 A1 | 6/2004 | Kwon |
| 2005/0033132 A1 | 2/2005 | Shults et al. |
| 2005/0214379 A1 | 9/2005 | Mecozzi et al. |
| 2005/0220880 A1 | 10/2005 | Lewis et al. |
| 2005/0287196 A1 | 12/2005 | Cho et al. |
| 2006/0240092 A1 | 10/2006 | Breitenkamp et al. |
| 2008/0194500 A1 | 8/2008 | Mecozzi et al. |

FOREIGN PATENT DOCUMENTS

| JP | 08-502753 T | 3/1996 |
| JP | 08-504811 T | 5/1996 |
| RU | 2162692 | 2/2001 |
| WO | WO94/09625 | 5/1994 |
| WO | WO94/14415 | 7/1994 |
| WO | PCT/US05/00100 | 7/2005 |
| WO | WO 2005/067517 | 7/2005 |
| WO | WO2005067517 | 7/2005 |
| WO | WO 2008/070490 | 6/2008 |

OTHER PUBLICATIONS

Abrol et al. (2004) "Formulation, Characterization and In Vitro Evaluation of Silymarin-Loaded Microspheres," *Drug Deliv.* 11:185-191.
Adams et al. (2003) "Amphiphilic Block Copolymers for Drug Delivery," *J. Pharm. Sci.* 92:1343-1355.
Akkar et al. (2003) "Formulation of Intravenous Carbamzepine Emulsions by SolEmuls Technology," *Eur. J. Pharmaceutics Biopharmaceutics* 55:305-312.
Akkar et al. (2003) "Intravenous Intraconazole Emulsion Produced by SolEmuls Technology," *Eur. J. Pharaceutics Biopharmaceutics* 56:29-36.
Akkar et al. (2004) "Solubilizing Poorly Soluble Antimycotic Agents by Emulsification Via a Solvent-Free Process," *AAPS PharmSciTech* 5(1).
Ashok et al. (2004) "In Vitro Characterization of PEGylated Phospholipid Micelles for Improved Drug Solubilization: Effects of PEG Chain Length and PC Incorporation," *J. Pharm. Sci.* 93(10):2476-2487.
Benita et al. (1993) "Submicron Emulsions as Colloidal Drug Carriers for Intravenous Administration: Comprehensive Physiocochemical Characterization," *J. Pharmaceutical Sci.* 82(11):1069-1079.
Benkwitz et al. (2004) "Influence of $GABA_A$ Receptor $\gamma 2$ Splice Variants on Receptor Kinetics and Isoflurane Modulation," *Anesthesiology* 101:924-936.
Biber et al. (1984) "Intravenous Infusion of Halothane Dissolved in Fat. Haemodynamic Effects in Dogs," *Acta Anaesthesiol Scand.* 28:385-389.
Bilgicer et al. (2001) "Programmed Self-Sorting of Coiled Coils with Leucine and Hexafluoroleucine Cores," *J. Am. Chem. Soc.* 123:11815-11816.

(Continued)

*Primary Examiner* — James Rogers
(74) *Attorney, Agent, or Firm* — Lathrop & Gage LLP

(57) ABSTRACT

The present invention provides therapeutic formulations, including therapeutic emulsions and nanoemulsions, and related methods for the delivery of fluorinated therapeutic compounds, including an important class of low boiling point perfluorinated and/or perhalogenated volatile anesthetics. Emulsion-based fluorinated volatile anesthetic formulations compatible with intravenous administration are provided that are capable of delivering and releasing amounts of fluorinated volatile anesthetic compounds effective for inducing and maintaining anesthesia in patients. Intravenous delivery of the present emulsion-based fluorinated volatile anesthetic formulations permits anesthetic levels in a patient to be selectively adjusted very rapidly and accurately without the need to hyperventilate patients and without the use of irritating agents.

31 Claims, 22 Drawing Sheets

(56) References Cited

OTHER PUBLICATIONS

Bilgicer et al. (2002) "Synthesis and Thermodynamic Characterization of Self-Sorting Coiled Coils," *Tetrahedron* 58:4105-4112.

Boileau et al. (1999) "Identification of Transduction Elements for Benzodiazepine Modulation of the GABA(A) Receptor: Three Residues are Required for Allosteric Coupling," *J. Neurosci.* 19:10213-10220.

Boileau et al. (2003) "Effects of γ2S Subunit Incorporation on $GABA_A$ Receptor Macroscopic Kinetics," *Neuropharmacology* 44:1003-1012.

Bourdon et al. (2000) "A Comparative Study of the Cellular Uptake, Localization and Photoxicity of *meta*-tetra (hydroxyphenyl) Chlorine Encapsulated in Surface-Modified Submicronic Oil/Water Carriers in HT29 Tumor Cells," *J. Photochem. Photobiol. B Biol.* 55:164-171.

Burt et al. (1999) "Development of Copolymers of Poly(D,L-Lactide) and Methoxypolyethylene Glycols as Micellar Carriers of Paclitaxel," *Coll. Surf. B. Biointerfaces* 16:191-171.

Capek, I. (2004) "Degradation of Kinetically-Stable o/w Emulsions," *Adv. Colloid Interface Sci.* 107:125-155.

Chansri et al. (2006) "Inhibition of Liver Metastasis by all-trans retinoic Acid Incorporated into O/W Emulsions in Mice," *Int. J. Pharmaceutics* 321(1-2):42-49.

Chesney et al. (2003) "Differential Uptake of Volatile Agents into Brain Tissue in Vitro. Measurement and Application of a Diffusion Model to Determine Concentration Profiles in Brain Slices," *Anesthesiology* 99:122-130.

Chiari et al. (2004) "Intravenous Emulsified Halogenated Anesthetics Produce Acute and Delayed Preconditioning Against Myocardial Infarction in Rabbits," *Anethesiology* 101:1160-1166.

Constantinides et al. (2000) "Formulation Development and Antitumor Activity of a Filter-Sterilizable Emulsion of Paclitaxel," *Pharmaceutical Research* 17(2):175-182.

Cruz et al. (2006) "Physico-Chemical Characterization and In Vivo Evaluation of Indomethacin Ethyl-Ester-Loaded Nanocapsules by PCS, TEM, SAXS, Interfacial Alkaline Hydrolysis and Antiedematogenic Activity," *J. Nanoscience Nanotechnol.* 6:3154-3162.

Cuignet et al. (2002) "A Second-Generation Blood Substitute (Perflubron Emulsion) Increases the Blood Solubility of Modern Volatile Anesthetics," *Anesth. Analg.* 95:368-372.

Davis et al. (Apr. 1981) "Ostwald Ripening and the Stability of Emulsion Systems: An Explanation for the Effect of an Added Third Component," *J. Colloid Interface Sci.* 80(2):508-511.

De Smet et al. (1999) "Ostwald Ripening of Alkane Emulsions in the presence of Surfactant Micelles," *Langmuir* 15:6745-6754.

Dias et al. (2007) "Pharmacokinetics and Tumor Uptake of a Derivatized Form of Paclitaxel Associated to a Cholesterol-Rich Nanoemulsion (LDE) in Patients in Gynecologic Cancers," *Cancer Chemother. Pharmacol.* 59:105-111.

Dong et al. (1984) "The Py Scale of Solvent Polarities," *Can. J. Chem.* 62:2560-2565.

Driscoll, D.F. (2006) "Lipid Injectable Emulsions: Pharmacopeial and Safety Issues," *Pharmaceutical Res.* 23(9):1959-1969.

Eger, E.I. (1998) "Current and Future Perspectives on Inhaled Anesthetics," *Pharmacotherapy* 18:895-910.

Eger et al. (1995) "Anesthesia by Intravenous Emulsified Isoflurane in Mice," *Can. J. Anesth.* 42:173-176.

El-Aasser et al. (2004) "Miniemulsions: Overview of Research and Applications," *J. Coating Technol. Res.* 1(1):20-31.

Erdlenbruch et al. (2000) "Transient and Controllable Opening of the Blood-Brain Barrier to Cytostatic and Antibiotic Agents by Alkylglycerols in Rats," *Exp. Brain. Res.* 135:417-422.

Flaim, S.F. (1994) "Pharmacokinetics and Side Effects of Perfluorocarbon-Based Blood Substitutes," *Art. Cells Blood Subs. Immob. Biotech.* 22(4):1043-1054.

Forster et al. (1998) "Applications of Emulsions," In; *Modern Aspects of Emulsion Science*, Binks, B. Ed., The Royal Society of Chemistry: Cambridge, pp. 395-426.

Forrest et al. (2006) "In Vitro Release of the mTOR Inhibitor Rapamycin from Poly(ethylene glycol)-*b*-poly(ε-caprolactone) Micelles," *J. Controlled Release* 110:370-377.

Franks et al. (1994) "Molecular and Cellular Mechanisms of General Anesthesia," *Nature* 367:607-614.

Franks et al. (1996) "Temperature Dependence on the Potency of Volatile General Anesthetics: Implications for in Vitro Experiments," *Anesthesiology* 84:716-720.

Friberg et al. (1978) "Emulsification and the HLB-Temperature," *J. Colloid Interface Sci.* 66:367-368.

Fujita et al. (1971) "Fluorocarbon Emulsion as a Candidate for Artificial Blood," *Eur. Surg. Res.* 3:436-453.

Gabizon et al. (May 1993) "Prolongation of the Circulation Time of Doxorubicin Encapsulated in Liposomes Containing a Polyethylene Glycol-Derivatized Phospholipid: Pharmocokinetic Studies in Rodents and Dogs," *Pharm. Res.* 10(5):703-708.

Greiner et al. (1993) "Fluorinated Surfactants Intended for Biomedical Uses," In; *Organofluorine Compounds in Medicinal Chemistry and Biomedical Applications*, Filler et al. Eds., Elsevier Science Publishers, pp. 339-380.

Halpern, D.F. (1993) "Recent Developments in Fluorine Substituted Volatile Anesthetics," In; *Organofluorine Compounds in Medicinal Chemistry and Biomedical Applications*, Filler et al. Eds., Elsevier Science Publishers, pp. 101-133.

Hapfelmeier et al. (2001) "Sevoflurane Potentiates and Blocks GABA-Induced Currents Through Recombinant Alpha(1)ss(2)gamma(2) GABA(A) Receptors: Implications for an Enhanced GABAergic Transmission," *Eur. J. Anesthesiology* 18:377-383.

Harris et al. (Mar. 2003) "Effect of Pegylation on Pharmaceuticals," *Nat. Rev. Drug Disc.* 2:214-221.

Higuchi et al. (1962) "Physical Degradation of Emulsions Via the Molecular Diffusion Route and the Possible Prevention Thereof," *J. Pharmaceutical Sci.* 51(5):459-466 *J. Pharm. Sci.* 51(5):459-466.

Hoang et al. (Aug. 31, 2004) "Aqueous Solubilization of Highly Fluorinated Molecules by Semifluorinated Surfactants," *Langmuir* 20(18):7347-7350.

Hoang et al. (2003) "Ostwald Ripening of Alkane in Water Emulsions Stabilized by Hexaethylene Glycol Dodecyl Ether," *Langmuir* 19:6019-6025.

Hoar et al. (1943) "Transparent Water-in-oil Dispersions: The Oleopathic Hydro-Micelle," *Nature* 152:102-103.

Holmgren et al. (1998) "Code for Collagen's Stability Deciphered," *Nature* 392:666-667.

Homgren et al. (1999) "A Hyperstable Collagen Mimic," *Chem. Biol.* 6(2):63-70.

Hung et al. (2006) "Development and Evaluation of Emulsion-Liposome Blends for Reservation Delivery," *J. Nanosci. Nanotechnol.* 6:2950-2958.

International Search Report, Corresponding to International Application No. PCT/US05/00100, Mailed Jul. 12, 2006.

International Search Report and Written Opinion, Corresponding to International Application No. PCT/US07/85710, Mailed Sep. 18, 2008.

Ishida et al. (2004) "Biodistribution Characteristics of Galactosylated Emulsions and Incorporated Probucol for Hapatocyte-Selective Targeting of Pipophilic Drugs in Mice," *Pharm. Res.* 21(6):932-939.

Izquierdo et al. (2002) "Formation and Stability of Nano-Emulsions Prepared Using the Phase Inversion Temperature Method," *Langmuir* 18:26-30.

Jadhav et al. (2006) "Applications of Microemulsion Based Drug Delivery System," *Curr. Drug Deliv.* 3:267-273.

Jafari et al. (2006) "Nano-Emulsion Production by Sonication and Microfluidization—A Comparison," *Int. J. Food. Properties* 9:475-485.

Johannesson et al. (1984) "Halothane Dissolved in Fat as an Intravenous Anesthetic to Rats," *Acta Anaesthesiol Scand.* 28(4):381-384.

Jones et al. (1999) "Polymeric Micelles: A New Generation of Colloidal Drug Carriers," *Eur. J. Pharm. Biopharm.* 48:101-111.

Jones et al. (2003) "Toxicological Perspectives on Perfluorinated Compounds," *Organohalogen. Comp.* 62:311-314.

(56) References Cited

OTHER PUBLICATIONS

Kabalnov et al. (1992) "Ostwald Ripening Theory: Applications to Fluorocarbon Emulsion Stability," *Adv. Colloid Interface Sci.* 38:69-97.
Kabalnov et al. (Dec. 1990) "Solubility of Fluorocarbons in Waster as a Key Parameter Determining Fluorocarbon Emulsion Stability," *J. Fluorine. Chem.* 50(3):271-284.
Kabalnov et al. (1996) "Macroemulsion Stability: The Oriented Wedge Theory Revisited," *Langmuir* 12:276-292.
Kalyanasundaram et al. (1976) "Environmental Effects on Vibronic Bans Intensities in Pyrene Monomer Fluorescence and their Application in Studies of Micellar Systems," *J. Am. Chem. Soc.* 99:2039-2044.
Kalyanasundaram, K. (1988) "Pyrene Fluorescence as a Probe of Fluorocarbon Micelles and their mixed Micelles with Hydrocarbon Surfactants," *Langmuir* 4:942-945.
Kawamoto et al. (1992) "Acute Pulmonary Edema After Intravenous Liquid Halothane in Digs," *Anesth. Analg.* 74:747-752.
Kennedy et al. (2004) "The Toxicology of Perfluorooctanoate," *Crit. Rev. Tox.* 34:351-384.
Khan et al. (2006) "Multiple Emulsions: An Overview," *Curr. Drug. Deliv.* 3:429-443.
Kim et al. (2002) "Pharmocokinetic and Pharmocodynamic Evaluation of Cyclosporin A O/W-Emulsion in Rats," *Int. J. Pharmaceutics* 249(1-2):149-156.
Kissa, E. (2001) "Polymeric Fluorinated Surfactants," In; *Fluorinated Surfactants and Repellents*, $2^{nd}$ ed., Surfactant Science Series, vol. 97, Marcel Dekker, Inc. pp. 15-28.
Komori et al. (2007) "Alteration of Therapeutic Efficacy of Lipid Micro Spheres Incorporating Prostaglandin E1 by Mixing with Aqueous Solution," *J. Pharmaceutical Sci.* 96(4):935-943.
Kopriva et al. (1969) "An Anesthetic Accident: Cardiovascular Collapse from Liquid Halothane Delivery," *Anesthesiology* 30:246-247.
Krafft et al. (1998) "Highly Fluorinated Amphiphiles and Colloidal Systems, and Their Applications in the Biomedical Field. A Contribution," *Biochimie* 80:489-514.
Krafft, M.P. (2001) "Fluorocarbons and Fluorinated Amphiphiles in Drug Delivery and Biomedical Research," *Adv. Drug Del. Rev.* 47:209-228.
Krafft et al. (1994) "Supramolecular Assemblies from Single Chain Perfluoroalkylated Phosphorylated Amphiphiless," *Coll. Surf. A* 84:113-119.
Krafft et al. (1991) "Detrimental Effect of Excess Lecithin on the Stability of Fluorocarbon/Lecithin Emulsions," *J. Phys. Chem.* 95:5673-5676.
Krafft, M.P. (2004) "Applications of Fluorous Compounds in Materials Chemistry," *Handbook of Fluorous Chemistry*, Gladysz et al. Eds., Wiley-VCH: Weinheim, CH. 12, pp. 478-504.
Krasowski et al. (2000) "The Actions of Ether, Alcohol and Alkane General Anesthetics on GABA and Glycine Receptors and the Effects of TM2 and TM3 Mutations," *Brit. J. Pharmacol.* 129:731-743.
Krishna et al. (1993) "Pharmacokinetics, Efficacy and Toxicity of Parenteral Haalofantrine in Uncomplicated Malaria," *Brit. J. Clin. Pharmacol.* 36:585-591.
Krishnadas et al. (Feb. 2003) "Sterically Stabilized Phospholipid Mixed Micelles: In Vitro Evaluation as a Novel Carrier for Water-Insoluble Drugs," *Pharm. Res.* 20(2):297-302.
Kwon et al. (1994) "Block Copolymer Micelles as Vehicles for Hydrophobic Drugs," *Colloids Surf. B. Biointerfaces* 2:429-434.
Kwon, G.S. (2003) "Polymeric Micelles for Delivery of Poorly Water-Soluble Compounds," *Crit. Rev. Ther. Drug Carrier Syst.* 20:357-403.
Kwon et al. (2003) "Polymeric Micelles for the Delivery of Polyene Antibiotics," *Polymeric Mater. Sci Eng.* 89:50-51.
Lance et al. (1995) "Structure and Toxicity of Amphotericin B/triglyceride Emulsion Formulations," *J. Antimicrob. Chemother.* 36(1):119-128.
Lau et al. (2004) "The Developmental Toxicity of Perfluoroalkyl Acids and their Derivatives," *Tox. Appl. Pharm.* 198:231-241.

Lavasanifar et al. (2001) "Micelles Self-Assembled from Poly(thylene oxide)-bloxk-poly-(N-hexyl stearate L-Aspartamide) by a Solvent Evaporation Method: Effect on the Solubilization and Haemolytic Activity of Amphotericin B," *J. Control. Rel.* 77:155-160.
Lavasanifar et al. (2002) "Poly(ethylene Oxide)-Block-Poly(L-Amino Acid) Micelles for Drug Delivery," *Adv. Drug Del. Rev.* 54:169-190.
Lifshitz et al. (1961) "The Kinetics of Precipitation from Supersaturated Solid Solutions," *J. Phys. Chem. Solids* 19(1-2):35-50.
Liu et al. (2007) "Preparation of Poly(butylene-co-ε-caprolactone carbonate) and Their use as Drug Carriers for a Controlled Delivery System," *J. Polym. Sci. A Polym. Chem.* 45(11):2152-2160.
Liu et al. (2006) "Formation and Stability of Paraffin Oil-in-Water Nano-Emulsions Prepared by the Emulsion Inversion Point Method," *J. Colloid Interface Sci.* 303:557-563.
Lixin et al. (2006) "A Less Irritant Norcantharidin Lipid Microspheres: Formulation and Drug Distribution," *Int. J. Pharmaceutics* 323(1-2):161-167.
Lo et al. (1987) "The Disposition and Bioavailability of Intravenous and Oral Nelbuphine in Healthy Volunteers," *J. Clin. Pharmacol.* 27:866-873.
Lukyanov et al. (May 7, 2004) "Micelles from Lipid Derivatives of Water-Soluble Polymers as Delivery Systems for Poorly Soluble Drugs," *Adv. Drug Deliv. Rev.* 56(9):1273-1289.
Madhusudhan et al. (2007) "1-O-alkylglycerol Stabilized Carbamazepine Intravenous o/w Nanoemulsions for Drug Targeting in Mice," *J. Drug Targeting* 15(2):154-161.
Martin et al. (2005) "Synthesis and Self-Assembly of Amphiphilic Semifluorinated Calix[4]arenes," *Supramol. Chem.* 17:9-15.
Martin et al. (2005) "Solution Self-Assembly and Solid-State Properties of Fluorinated Amphiphilic Calix[4]arenes," *Chem. Comm.* 39:4964-4966.
Martin et al. (2006) "Synthesis and pH-Dependent Self-Assembly of Semifluorinated Calix[4]arenes," *Tetrahedron* 63(25):5539-5547.
Mason et al. (2006) "Nanoemulsions: Formation, Structure and Physical Properties," *J. Phys. Condens. Matter* 18:R635-R666.
Medina et al. (2001) "Use of Ultrasound to prepare Lipid Emulsions of Lorazepam for Intravenous Injection," *Int. J. Pharmaceutics* 216(1-2):1-8.
Messina et al. (1998) "Perfluorocarbon-Hydrocarbon Self-Assembly. Part 3. Liquid Phase Interactions Between Perfluoroalkylhalides and Heteroatom Containing Hydrocarbons," *Tetrahedron Lett.* :9069-9072.
Miller, C.A. (2006) "Spontaneous Emulsification Recent Developments with Emphasis on Self-Emulsification," In; *Emulsions and Emulsion Stability*, $2^{nd}$ ed., Sjonlom, J. Ed., Marcel Dekker: New York, 132:107-126.
Monduzzi, M. (1998) "Self-Assembly in Fluorocarbon Surfactant Systems," *Curr. Opin. Coll. Int. Sci.* 3:467-477.
Mosqueira et al. (2006) "Surface-Modified and Conventional Nanocapsules as Novel Formations for Parental Delivery of Halofantrine," *J. Nanosci. Nanotechnol.* 6:3193-3202.
Mosqueira et al. (2004) "Efficacy and Pharmacokinetics of Intravenous Nanocapsule Formulations of Halofantrine in *Plasmodium berghei*-Infected Mice," *Antimicrobial Agents Chemother.* 48:1222.
Mozzi et al. (2002) "The Use of Lipid Emulsions for the IV Administration of a New Water Soluble Polyene Antibiotic, SPK-843," *J. Antimicrob. Chemother.* 49(2):321-325.
Müller et al. (2004) "SolEmuls—Novel Technology for the Formulation of I.V. Emulsions with Poorly Soluble Drugs," *Int. J. Pharmaceutics* 269(2):293-302.
Musser et al. (1999) "The Anesthetic and Physiologic Effects of an Intravenous Administration of a Halothane Lipid Emulsion (5% vol/vol)," *Aneth. Analg.* 88:671-675.
Nakajima, H. (1997) "Microemulsions in Cosmetics," In; *Industrial Applications of Microemulsions*, Solans et al. Eds., Marcel Decker: New York, pp. 175-197.
Neil et al. (2000) "Towards the Nonstick Egg: Designing Fluorous Proteins," *Chem. Biol.* 7:R153-R157.
Nordén et al. (2001) "Physiocochemical Characterization of a drug-Containing Phospholipid-Stabilized o/w Emulsion for Intravenous Administration," *Eur. J. Pharmaceutical Sci.* 13(4):393-401.

(56) References Cited

OTHER PUBLICATIONS

Oda et al. (2000) "Aggregation Properties and Mixing Behavior of Hydrocarbon, Fluorocarbon, and Hybrid Hydrocarbon-Fluorocarbon Cations Dimeric Surfactants," *Langmuir* 16:9759-9769.

Office Action, Corresponding to U.S. Appl. No. 11/028,948, Mailed Aug. 1, 2008.

Ozpolat et al. (2003) "Pharmacokinetics of Intravenously Administered Liposomal All-Trans-Retinoic Acid (ATRA) and Orally Administered ATRA in Healthy Volunteers," *J. Phram. Pharmaceutical Sci.* 6:292-301.

Palakurthi et al. (2005) "Biodisposition of PEG-Coated Lipid Microspheres of Indomethacin in Arthritic Rats," *Int. J. Pharmaceutics* 290(1-2):55-62.

Percec et al. (2002) "Cell Membrane as a Model for the Design of Semifluorinated Ion-Selective Nanostructures Supramolecular Systems," *Tetrahedron* 58:4031-4040.

Petsev et al. (1995) "Flocculation of Deformable Emulsion Droplets. II. Interaction Energy," *J. Colloid Interface Sci.* 176:201-213.

Pohlmann et al. (2002) "Spray-Dried Indomethacin-Loaded Polyester Nanocapsules and Nanospheres Development, Stability Evaluation and Nanotstructure Models," *Eur. J. Pharmaceutical Sci.* 16(4-5):305-312.

Primo et al. (2007) "Binding of Photophysical Studies of Biocompatible Magnetic Fluid in Biological Medium and Development of Magnetic Nanoemulsion: A New Candidate for Cancer Treatment," *J. Magnetism Magnetic Mater.* 310:2838-2840.

Ravey et al. (1988) "Comparative Study of Fluorinated and Hydrogenated Nonionic Surfactants," *Prog. Colloid Poly. Sci.* 76:234-241.

Riess J.G. (2002) "Fluorous Micro- and Nanophases with a Biomedical Perspective," *Tetrahedron* 58:4113-4131.

Riess, J.G. (2004) "Fluorous Materials for Biomedical Uses," In; *Handbook of Fluorous Chemistry*, Wiley-VCH, pp. 521-573.

Riess, J.G. (2001) "Oxygen Carriers (Blood Substitutes)-Raison d'Etre, Chemistry and Some Physiology," *Chem. Rev.* 101:2797-2919.

Riess, J.G. (1994) "Highly Fluorinated Systems for Oxygen Transport, Diagnosis and Drug Delivery," *Colloids Surf. A.* 84:33-48.

Reiss et al. (1992) "Stabilization of Fluorocarbon Emulsions by Sugar-Derived Perffluoroalkylated Surfactants and Co-surfactants," *Prog. Colloid Polym. Sci.* 88:123-130.

Reiss, J.G. (2005) "Understanding the Fundamentals of Perfluorocarbons and Perfluorocarbon Emulsions Relevant to In Vivo Oxygen Delivery," *Artificial Cells Blood Subdtitutes Biotechnol.* 33:47-63.

Rosier et al. (2001) "Advanced Drug Delivery Devices Via elf-Assembly of Amphiphilic Block Copolymers," *Adv. Drug Del. Rev.* 53:95-108.

Salager et al. (1982) "Surfactant-Oil-Water Systems Near the Affinity Inversion. Part I: Relationship Between Equilibrium Phase Behavior and Emulsion Type and Stability," *J. Dispersion Sci. Technol.* 3:279-292.

Sandison et al. (1970) "An Experimental Study of Pulmonary Damage Associated with Intravenous Injection of Halothane in Dogs," *Br. J. Anaesth.* 42:419-423.

Sarker, D.K. (2005) "Engineering of Nanoemulsions for Drug Delivery," *Curr. Drug Deliv.* 2:297-310.

Schmutz et al. (2003) "Fluorinated Vesicles Made from Combinations of Phospholipids and Semifluorinated Alkanes. Direct Experimental Evidence of the Location of Semifluorinated Alkane Within the Bilayer," *Langmuir* 19:4889-1894.

Schulman et al. (1959) "Mechanism of Formation and Structure of Micro Emulsions by Electron Microscopy," *J. Phys. Chem.* 63:1677-1680.

Seki et al. (2004) "A Nanometer Lipid Emulsion, Lipid Nano-Sphere (LNS), as a Parental Drug Carrier fro Passive Drug Targeting," *Int. J. Pharmaceutics* 273(1-2):75-83.

Sharma et al. (1988) "Novel Compositions of Emulsified Perfluorocarbons for Biological Uses," *Biomat. Art. Cells Art. Org.* 16:447-450.

Shawer et al. (2002) "VLDL-Resembling Phospholipid-Submicron Emulsion for Cholesterol-Based Targeting," *J. Pharmaceutical Sci.* 91(6):1405-1413.

Shinoda et al. (1968) "The Effect of Temperature on the Phase Equilibria and the Types of Dispersions of the Ternary System Composed of Water, Cyclohexane, and Nonionic Surfactant," *J. Colloid Interface Sci.* 26:70-74.

Slaughter et al. (2007) "Synthesis and Self-Assembly Properties of a Novel [poly9ethylene glycol0}-Fluorocarbon-Phospholipid Triblock Copolymer," *Tetrahedron Lett.* 48:3879-3882.

Smart, B.E. "Characteristics of C-F Systems," In; *Organofluorine Chemistry: Principles and Commercial Applications*, Plenum Press, New York, pp. 57-88.

Smart, B.E. (1983) "Fluorocarbons," In; *The Chemistry of Functional Groups*, Supplement D, John Wiley and Sons, pp. 603-655.

Solans et al. (2003) "Nano-Emulsions: Formation, Properties and Applications," In; *Adsorption and Aggregation of Surfactants in Solution*, Marcel Dekker, Inc.: New York, pp. 525-554.

Solans et al. (2005) "Nano-Emulsions," *Curr. Opin. Colloid Interface Sci.* 10:102-110.

Strippoli et al. (2000) "Anticandidal Activity of SPA-S-843, a New Polyenic Drug," *J. Antomicrob. Chemother.* 45:235-237.

Sutton et al. (1971) "Accidental Intravenous Injection of Halothane," *Br. J. Anaest.* 43:513-519.

Swanson et al. (1953) "Ultra-Short-Acting Thiobarbituric Acids," *Proc. Soc. Exp. Biol. Med.* 82:212-215.

Tadros et al. (2004) "Formation and Stability of Nano-Emulsions," *Adv. Colloid Interface Sci.* 108-109:303-318.

Tang et al. (2001) "Stabilization of Coiled-Coil Peptide Domains by Introduction of Trifluoroleucine," *Biochemistry* 40:2790-2796.

Taylor, P. (1998) "Ostwald Ripening in Emulsions," *Adv. Colloid Interface Sci.* 75:107-163.

Taylor, P. (2003) "Ostwald Ripening in Emulsions. Estimation of Solution Thermodynamics of the Disperse Phase," *Adv. Colloid Interface Sci.* 106:261-285.

Teixeira et al. (2005) "Development and Characterization of PLGA Nanospheres and Nanocapsules Containing Xanthone and 3-Methoxyxanthone," *Eur. J. Pharmaceutics Biopharmaceutics* 59:491-500.

Thurmond et al. (1999) "Shell Cross-Linked Polymer Micelled: Stabilized Assemblies with great Versatility and Potential," *Coll. Surf B* 16:45-54.

Tiwari et al. (2006) "Preparation and In Vitro Characterization of Multifunction nanoemulsions for Simultaneous MR Imaging and Targeted Drug Delivery," *J. Biomed. Nanotechnol.* 2:217-224.

Torchilin, V.P. (2001) "Structure and Design of Polymeric Surfactant-Based Drug Delivery Systems," *J. Controlled Release* 73:137-172.

Ueda et al. (2004) "Prolonged Circulation of Menatetrenone by Emulsions with Hydrogenated Castor Oils in Rats," *J. Controlled Release* 95(1):93-100.

van Etten et al. (Nov. 1995) "Sterically Stabilized Amphotericin B-Liposomes: Toxicity and Biodistribution in Mice," *J. Controlled Release* 37(1-2):123-129.

Vierling et al. (Feb. 2001) "Highly Fluorinated Amphiphiles as Drug and Gene Carrier and Delivery Systems," *J. Fluorine Chem.* 107(2):337-354.

Wang et al. (2006) "Submicron Lipid Emulsion as a Drug Delivery System for Nalbuphine and Its Prodrugs," *J. Controlled Release* 115(2):140-149.

Watkins et al. (1993) "*Falciparum* Malaria: Differential Effects of Antimalarial Drugs on Ex Vivo Parasite Viability During the Critical Early Phase of Therapy," *Am. J. Trop. Med. Hygiene* 49:106.

Weers et al. (1994) "The Effect of Molecular Diffusion on Initial Particle Size Distributions in Phospholipid-Stabilized Fluorocarbon Emulsions," *Colloids Surf. A Physiochem. Eng. Aspects* 84:81-87.

Wu et al. (1996) "Potentation by Sevoflurane of the γ-Aminobutyric Acid Induced Chloride Current in Acutely Dissociated CA1 Pyramidal Neurons from Rat Hippocampus," *Brit. J. Pharmacol.* 119:1013-1021.

(56) References Cited

OTHER PUBLICATIONS

Xue et al. (1997) "Perfectly Staggered and Twisted Difluorormethylsene Groups in Perfluoroalkyl Chains: Structure of M[$C_4F_9SO_2NSO_2C_4F_9$] (M=Na, K)," *Angew. Chem. Int. Ed. Engl.* 36:1331-1333.
Yeeprae et al. (2005) "Biodistribution Characteristics of Mannosylated and Fucosylated O/W Emulsions in Mice," *J. Drug Targeting* 13(8):479-487.
Yeeprae et al. (2006) "Effect of Mannose Density on Mannose Receptor-Mediated Cellular Uptake of Mannosylated O/W Emulsions by Macrophages," *J. Controlled Release* 114(2):193-201.
Yu et al. (2001) "mTOR, a Novel Target in Breast Cancer: The Effect of CCO-779, an mTOR Inhibitor, in Preclinical Models of Breast Cancer," *Endocrine-Related Cancer* 8:249-258.
Zalipsky, S. (1993) "Synthesis of an End-Group Functionalized polyethylene glycol-Lipid Conjugate for Preparation of Polymer-Grafted Liposomes," *Bioconj. Chem.* 4(4):296-299.
Zarif et al. (1993) "Alkyl and Perfluooalkyl Glycolipid-Based Supramolecular Assemblies," *Coll. Surf. A* 84:107-112.
Zhang et al. (1996) "Development of Amphiphilic Diblock Copolymers as Micellar Carriers of Taxol," *Int. J. Pharmaceutics* 132:195-206.
Zhou et al. (2006) "The Efficacy and Safety of Intravenous Emulsified Isoflurane in Rats," *Anesth. Analg.* 102:129-134.
Zimmerman et al. (1994) "Potentiation of $GABA_A$ Receptor Cl⁻ Current Correlates with in Vivo Anesthetic Potency," *J. Pharmacol. Experim. Ther.* 270:987-991.
Adams et al. (2003) "Relative Aggregation State and Hemolytic Activity of Amphotericin B Encapsulated by Poly(Ethylene Oxide)-*Block*-poly(*N*-hexyl-L-aspartamide)-acyl Conjugate Micelled: Effects of Acyl Chain Length," *J. Control. Release* 87:23-32.
Buszello et al. (2000) Emulsions as Drug Delivery Systems, In; *Pharmaceutical Emulsions and Suspensions*, Nielloud et al. Eds., Marcel Dekker: New York, 105:191-228.
Cuignet et al. (2002) "A Second-Generation Blood Substitute (Perflubron Emulsion) Increases the Blood Solubility of Modern Volatile Anesthetics In Vitro," *Anesth Analg.* 95:368-372.
Definition of the Word "Derivative," http://www.merriamwebster.com/dictionary/derivative, Downloaded Jan. 27, 2011.
Ettmayer et al. (May 6, 2004) "Lessons Learned from Marketed and Investigational Prodrugs," *J. Med. Chem.*47(10):2393-2404.
Fast et al. (Oct. 2008) "Fluoropolymer-Based Emulsions for the Intravenous Delivery of Sevoflurane," *Anesthesiology* 109(4):651-656.
Ferstandig, L.L. (1995) "Fluorinated Anesthetics," In; *Chemistry of Organic Fluorine Compounds II: A Critical Review*, Hudlický et al. Eds., ACS Monograph No. 18, American Chemical Society, Washington, D.C., pp. 1133-1137.
Hillaireau et al. (2006) "Polymeric Nanoparticles as Drug Carriers," In; *Polymers in Drug Delivery*, Uchegbu et al. Eds., CRC: Boca Raton, pp. 101-110.
Office Action Corresponding to U.S. Appl. No. 11/972,061, Mailed Feb. 8, 2011.
Office Actions and Response Corresponding to U.S. Appl. No. 11/028,948, Mailed between Aug. 1, 2008 and Apr. 15, 2009.
Riess et al. (1988) "Design, Synthesis and Evaluation of Fluorocarbons and Surfactants for in Vivo Applications New Perfluoroalkylated Polyhydroxylated Surfactants," *Biomat. Art. Cells Art. Org.* 16(1-3):421-430.
Stella, V.J. (2004) "Prodrugs as Therapeutics," *Exp. Opin. Ther. Patents.* 14(3):277-280.
Strickley, R.G. (Feb. 2004) "Solubilizing Excipients in Oral and Injectable Formulations," *Pharm. Res.* 21(2):201-230.
Testa et al. (1996) "Prodrugs Revisited: The 'Ad Hoc' Approach as a Complement to Ligand Design," *Med. Res. Rev.* 16(3):233-241.
Testa, B. (2004) "Prodrugs Research: Futile or Fertile," *Biochemical Pharmacology* 68:2097-2106.
Torchilin, V.P. (2004) "Targeted Polymeric Micelled for Delivery of Poorly Soluble Drugs," *CLMS Cell. Mol. Life Sci.* 61:2549-2559.
van den Temple, M. (1953) "Stability of Oil-In-Water Emulsions II; Mechanism of the Coagulation of an Emulsion," *Recl. Tray. Chim. Pays-Bas* 72:433-441.
Walstra et al. (1998) "Emulsion Formation," In; *Modern Aspects of Emulsion Science*, Binks, B. Ed., The Royal Society of Chemistry: Cambridge, pp. 56-99.
Wang et al. (2007) "Formulation, Preparation and Evaluation of Flunarizine-Loaded Lipid Microspheres," *J. Pharm. Pharmacol.* 59:351-357.
Weers et al. (1994) "Room Temperature Stable Perfluorocarbon Emulsions with Acceptable Half-Lives in the Reticuloendotherlial System," *Art. Cells Blood Subs. Immob. Biotech.* 22(4):1175-1182.
Wolff, M.E. (1994) Burger's Medicinal Chemistry and Drug Discovery vol. 1., *Principles and Practice*, 5th Ed. pp. 975-977.
Written Opinion Corresponding to International Application No. PCT/US05/00100, Mailed Jul. 12, 2006.
Yu et al. (2006) "Formulation and Evaluation of Nimodipine-Loaded Lipid Microspheres," *J. Pharm. Pharmacol.* 8:1429-1435.
Supplementary European Search Report corresponding to European Patent Application No. EP07871604, completed Apr. 10, 2013.
Hsu, et al., "Diminution of Phagocytosed Perfluorocarbon Emulsions Using Perfluoroalkylated Polyethylene Glycol Surfactant," May 18, 2001, *Biochemical and Biophysical Research Communications*, vol. 283, Issue 4, pp. 776-781.
Notice of Reasons for Rejection corresponding to Japanese Patent Application No. P2009-539451, dispatched Dec. 11, 2012 (includes English translation).

Sevoflurane

Isoflurane

Desflurane

FLUOROPOLYMER-BASED EMULSIONS FOR THE INTRAVENOUS DELIVERY OF FLUORINATED VOLATILE ANESTHETICS

CROSS-REFERENCE TO RELATED APPLICATIONS

This application claims the benefit of U.S. Provisional Patent Application 60/867,432 filed Nov. 28, 2006, which is hereby incorporated by reference in its entirety to the extent not inconsistent with the disclosure herein.

STATEMENT ON FEDERALLY SPONSORED RESEARCH OR DEVELOPMENT

This invention was made with United States government support awarded by the following agencies: NSF Grants: 0518112 and 0520527. The United States government has certain rights in this invention.

BACKGROUND OF THE INVENTION

Nanoemulsions are composed of nanoscale droplets of one immiscible liquid dispersed within another. Many drugs are hydrophobic, which leads to limited water solubility, causing the delivery of water-insoluble drugs to be a primary focus of drug delivery research. Emulsions provide a central oil core, stably dispersed in water, that can act as a reservoir for hydrophobic drugs. While emulsions have long been used for topical administration, the small size of nanoemulsions makes them potentially attractive for parenteral delivery. In addition to solubilization of hydrophobic drugs, emulsions can reduce pain or irritation upon injection, improve pharmacokinetics, allow for new forms of administration and can provide for sustained or targeted release.

Phospholipid-stabilized soybean oil emulsions were the first approved intravenous emulsion and have been used clinically as i.v. nutritional supplements for over 40 years. Emulsions have also been employed clinically for the delivery of anesthetic, anti-inflammatory and analgesic drugs as well as for blood substitutes. Clinical trials have investigated emulsion formulations for anti-fungal drugs, anti-cancer agents, and radio contrast agents. However, there has not been extensive study of emulsion formulations for the delivery of volatile anesthetics. FIG. 1 provides the chemical structures of several common fluorinated volatile general anesthetics. This class of general anesthetics comprises highly fluorophilic compounds comprising perfluoroethers and substituted perfluoroethers. Fluorine substitution in these compounds provides for use substantially safer than their corresponding hydrocarbon counterparts. Desflurane and sevoflurane, in particular, are the dominant fluorinated volatile anesthetics used in half the general anesthetics supplied in North America. Nanoemulsion delivery systems for anesthetic compounds has promise to enable a new class of intravenously deliverable anesthetic formulations potentially providing a viable alternative to conventional administration of anesthetics via inhalation.

There are many clinical scenarios where the use of intravenous formulations of fluorinated volatile anesthetics offers significant advantages. New applications of intravenous delivery of volatile agents in the modern operating room relate primarily to speed of onset of drug action. When drugs are delivered by inhalation there is an inherent delay in onset, as the concentration in the anesthetic circuit that leads to the patient rises more slowly than at the outflow from the anesthetic vaporizer. The concentration in the lungs rises more slowly still because delivery to the alveoli and transfer to the blood are limited by the rate of ventilation and blood flow. Thus, even with "overpressurization", in which concentrations higher than the desired equilibrium concentration are delivered transiently, changes in the level of anesthesia are much slower (minutes) than optimal in a rapidly changing clinical environment. This is the primary reason that intravenous agents such as thiopental and propofol are used for "induction" of anesthesia, followed by a transition to inhaled agents as the effects of the intravenous agents dissipate. If it were possible to perform intravenous induction using volatile agents themselves there would be no need to replace one anesthetic with another, thus simplifying the induction process and adding a measure of stability and safety.

There are a number of situations in which rapid changes in the level of anesthesia are required not just for induction of anesthesia and insertion of an endotracheal tube for mechanical ventilation, but also during the middle of surgical procedures. These are typically situations associated with intense but brief stimuli, such as the insertion of "head pins" to stabilize the skull for neurosurgical procedures or direct laryngoscopy for examination of the airway. Deep levels of anesthesia are required to blunt the hemodynamic consequences of these intense stimuli, which are sudden in onset but brief. The ability to rapidly change the level of anesthesia by injecting an agent directly into the bloodstream would prove extremely useful for these and other clinical applications. Further, the brief duration of anesthetic action following a single bolus injection may allow the duration of anesthetic effect to be matched precisely with the duration of the surgical stimulus, thus minimizing hemodynamic consequences and improving safety.

Similarly, during the majority of surgical procedures there is a period of time following intubation of the trachea that the level of surgical stimulation is very low or absent, as the patient is positioned and a sterile field is established. During this time a light plane of anesthesia is required so that blood pressure is maintained. At the time of the surgical incision anesthesia must be deepened quickly. At present this is accomplished by attempting to anticipate the timing of the incision by a minute or two and increasing the level of anesthesia early, so that as the blood pressure falls the incision is made and the blood pressure rises to the desired level. Thus, this is a time of rapid changes in blood pressure and heart rate. One of the major challenges facing the anesthesiologist is maintaining stable hemodynamics in the face of rapidly changing anesthetic requirements at the beginning of a surgical procedure. Again, by more closely matching the onset of anesthetic action with the onset of the surgical stimulus using intravenous anesthetic delivery, stability and safety may be improved substantially.

Beyond the advantages imparted by more rapid titration of drug levels, intravenous delivery has potential to allow or facilitate the use of volatile anesthetics outside of the traditional realm of the operating theater. These include the use of volatile agents for sedation, and for induction and maintenance of general anesthesia under circumstances where delivery via inhalation is difficult or impossible. For example, sedation is occasionally required in the MRI or CT suite, where it is necessary that patients remain still. In addition, sedation is also often required in the clinic for colonoscopy and other uncomfortable procedures. The rapid recovery profile permitted by volatile anesthetics would be ideal in these situations, and significantly more rapid than for the most popular current regimen of fentanyl and midazolam. Further, their ability to blunt responses to noxious stimuli would confer a distinct advantage over propofol, a new intravenous anesthetic that is increasingly used for sedation because of its rapid recovery profile, but that has little or no analgesic property Recently, substantial research has been directed at developing lipid-based delivery systems for the intravenous administration of fluorinated volatile anesthetics. Warltier et al. and Liu et al. have recently addressed the intravenous administration of halogenated anesthetics via lipid emulsions. (See, Chiari, P. C.; Pagel, P. S.; Tanaka, K.; Krolikowski, J. G.; Ludwig, L. M.; Trillo, R. A.; Puri, N.; Kersten, J. R.; Warltier, D. C. "Intravenous Emulsified Halogenated Anesthetics produce Acute and Delayed Preconditioning against Myocardial Infarction in Rabbits" Anesthesiology 2004, 101, 1160-1166; and Zhou, J.-X.; Luo, N.-F.; Liang, X.-M.; Liu, J. "The Efficacy and Safety of Intravenous Emulsified Isoflurane in Rats" Anesth. Analg. 2006, 102, 129-134). Warltier et al. report that emulsified anesthetics produce acute and delayed preconditioning against myocardial infarction. Liu et al. report that combinations of simple lipids such as soy bean oil and glycerol (Intralipid) could be used for making anesthetic emulsions. While these results demonstrate the potential feasibility of lipid emulsions for the delivery of volatile anesthetics, there are significant drawbacks to this approach which hinder its practical implementation. First, emulsions of volatile fluorinated anesthetics based on Intralipid are not expected to be stable over time at high anesthetic concentrations. The effectiveness of these formulations for intravenous administration of volatile anesthetics, therefore, is expected to degrade significantly as a function of time. This property is undesirable as it renders such lipid-based formulations short practical lifetimes and shelf lives. Second, common lipids such as Intralipid have been shown to emulsify a maximum of 3.6% in volume of sevoflurane. This substantial limitation on the volume of anesthetic capable of emulsification is expected to present a significant challenge for practical implementation of lipid-based delivery systems for intravenously administered fluorinated volatile anesthetics.

An alternative approach to emulsions, which employ micelle systems for the delivery of fluorinated volatile anesthetics, is described in U.S. Patent Publication US2005/0214379 (Mecozzi et al.) published on Sep. 29, 2005. Delivery systems are described comprising fluorinated block copolymers having a hydrophilic block and a fluorinated or semifluorinated block. Applicability of the delivery system for encapsulation and administration of a variety of fluorine containing therapeutic compositions, including sevoflurane, is reported. In this delivery system, fluorinated block copolymers are provided at a concentration larger than the critical micelle concentration so as to form stable supramolecular structures for encapsulating fluorophilic chemical compounds. Specifically, the block copolymers self assemble into micelles wherein the fluorinated or semifluorinated blocks of the copolymer orient toward and surround a fluorous core of the fluorine containing therapeutic. A variety of block copolymer compositions are report as useful for administration of fluorinated therapeutic compositions, include dual block copolymers having a poly(ethylene glycol) block and a perfluorinated alkane block.

It will be appreciated from the foregoing that delivery systems enabling the intravenous administration of fluorinated volatile anesthetics are needed to provide an alternative to vapor inhalation in general anesthesia. Systems and formulations capable of providing highly concentrated emulsions of anesthetic are needed to enable intravenous delivery of anesthetics in amounts required for important clinical applications. Systems and formulations providing concentrated emulsions of anesthetic exhibiting stable particle sizes and anesthetic concentrations are needed to allow practical implementation of intravenous fluorinated volatile anesthetics. Systems and formulations for intravenous delivery of fluorinated volatile anesthetics exhibiting a high degree of biocompatibility and low toxicity are needed.

SUMMARY OF THE INVENTION

The present invention provides therapeutic formulations, including therapeutic emulsions and nanoemulsions, and related methods for the delivery of fluorinated therapeutic compounds, including an important class of low boiling point perfluorinated and/or perhalogenated volatile anesthetics. Emulsion-based fluorinated volatile anesthetic formulations compatible with intravenous administration are provided that are capable of delivering and releasing amounts of fluorinated volatile anesthetic compounds effective for inducing and maintaining anesthesia in patients. Intravenous delivery of the present emulsion-based fluorinated volatile anesthetic formulations permits anesthetic levels in a patient to be selectively adjusted very rapidly and accurately without the need to hyperventilate patients and without the use of irritating agents.

In an embodiment, the present formulations comprise a combination of a surfactant, such as one or more semi-fluorinated block copolymers, and a stabilizing additive, such as one or more perhalogenated fluorocarbons, capable of generating an emulsion of a large amount of a fluorinated volatile anesthetic dispersed in an aqueous solution. Therapeutic formulations of the present invention include nanoemulsions comprising submicron droplets of fluorinated volatile anesthetic and stabilizing additive, dispersed in a continuous phase comprising an aqueous solution. In some embodiments, droplets of fluorinated volatile anesthetic and stabilizing additive of the emulsion are stabilized by the formation of supramolecular structures of self assembled semi-fluorinated block copolymer surfactants that reduce the interfacial tension with fluorinated liquids at the droplet interface. In some embodiments, for example, surfactant comprising semi-fluorinated block copolymers having a hydrophilic block and a fluorophilic block self-assemble upon emulsification to form supramolecular structures dispersed in an aqueous continuous phase, thereby encapsulating and stabilizing significant quantities of the fluorinated volatile anesthetic component in a fluorous inner droplet core. For example, the fluorophilic block of the semi-fluorinated block copolymer surfactant may be preferentially oriented toward and proximate to the fluorous internal core of the supramolecular structure, thereby functioning as a molecular recognition element for the fluorinated volatile anesthetic. Optionally, the dispersed phase droplets of fluorinated volatile anesthetic may also have a stabilizing additive component for providing useful chemical and physical properties. Anesthetic formulations of the present invention comprising emulsions and nanoemulsions having a perhalogenated fluorocarbon stabilizing additive component, for example, exhibit enhanced stability with respect to droplet size by decreasing the rate of Ostwald ripening, coagulation and/or phase separation processes.

The present therapeutic formulations provide enhanced delivery performance relative to conventional lipid-base delivery systems by enabling emulsions having higher concentrations of fluorinated volatile anesthetics. Compositions of this aspect of the present invention allow for efficient formulation, administration and delivery of anesthetic to a patient or subject. In some embodiments, the present emulsion-based formulations provide effective delivery to specific active sites on ion channels and neurotransmitter receptors of a patient. Therapeutic formulations of this aspect of the present invention also provide a high degree of versatility, as the composition of the semi-fluorinated block copolymer surfactant (e.g. length of the hydrophilic block, length of the fluorophilic block, number of carbon-fluorine bonds, etc.) and the amount and chemical composition of perhalogenated fluorocarbon stabilizing additive(s) may be selectively adjusted to: (i) enhance stability under delivery conditions, (ii) optimize the kinetics of release of the fluorinated therapeutic for a specific application (e.g. provide faster or slower release rates), and (iii) enhance the overall formulation stability of therapeutic nanoemulsions under storage conditions (e.g., increase useful self life).

In an aspect, the present invention provides therapeutic formulations, including emulsion and nanoemulsions, for the administration of fluorinated therapeutic compounds. A therapeutic formulation of this aspect comprises an aqueous solution; semi-fluorinated block copolymers having a hydrophilic block and a fluorophilic block; a fluorinated therapeutic compound; and a stabilizing additive. In an embodiment, the semi-fluorinated block copolymers function as a surfactant for encapsulating and/or stabilizing dispersed phase droplets of fluorinated therapeutic compound(s) and stabilizing additive(s). In an embodiment, the stabilizing additive is one or more perhalogenated fluorocarbon compounds. Useful therapeutic formulations of the present invention may be provide as a therapeutic emulsion comprising: a continuous phase comprising the aqueous solution; and a dispersed phase where the semi-fluorinated block copolymers stabilize the fluorinated therapeutic compound, and optionally the perhalogenated fluorocarbon stabilizing additive, wherein the droplets of the dispersed phase are dispersed in the continuous phase. As used herein, the term formulation refers to compositions prepared for a desired therapeutic use. Formulations of the present invention may be present in a form ready for administration to a subject or may be provided in a form that requires one or more additional steps prior to administration to a subject. Formulations of the present invention include therapeutic emulsions and include precursor compositions for therapeutic emulsions.

This aspect of the present invention is attractive for therapeutic formulations for delivery of fluorinated therapeutic compounds comprising an anesthetic, such as sevoflurane, isoflurane, desflurane, enflurane and/or methoxyflurane. In an embodiment, the therapeutic formulation of this aspect of the present invention comprises a nanoemulsion formulation wherein dispersed phase droplets comprise a fluorinated anesthetic and one or more stabilizing agents, wherein said dropets have an average diameter less than or equal to 1000 nanometers, preferably for some applications an average diameter less than or equal to 500 nanometers, and more preferably for some applications an average diameter less than or equal to 300 nanometers. Optionally, the therapeutic formulation of this aspect of the present invention is capable of delivery to a patient via parenteral administration, such as via intravenous injection.

The composition of the semi-fluorinated copolymer surfactant component is an important parameter for controlling the stability, pharmacokinetic properties and biocompatibility of the present formulations. For example, selection of the composition of the fluorophilic block (e.g., the number of carbons of a fluorinated or perfluorinated alkyl chain, number of carbon-fluorine bonds etc.) and/or the composition of the hydrophilic block (e.g., composition, size, molecular weight etc.) is selected so as to establish useful chemical or physical properties of the nanoemulsion for a given application, such as to enhance stability (e.g., shelf life) and/or provide desired release properties of the therapeutic formulation. In an embodiment, for example, the fluorophilic block of the semi-fluorinated copolymer surfactant component is a fluorinated alkyl chain, such as perfluorinated alkyl chain, semifluorinated alkyl chain, perhalogenated alkyl chain and/or saturated fluorinated or perfluorinated alkyl chain. Exemplary fluorophilic blocks of semi-fluorinated copolymers of the present invention have lengths of 6 to 16 carbons. In an embodiment, the hydrophilic block of the semi-fluorinated copolymer comprises polyoxygenated block of the polymer, such as a poly(ethylene glycol) block. Exemplary hydrophilic blocks of semi-fluorinated copolymers of the present invention include a poly(ethylene glycol) block having a molecular weight selected over the range of 500 g mol$^{-1}$ to 12,000 g mol$^{-1}$. Selection of the size/molecular weight of the poly(ethylene glycol) block in some compositions establishes the release rate of fluorinated anesthetic and/or stability with respect to ripening, coagulation and phase separation processes.

In an embodiment of the present invention particularly useful for delivery of fluorinated volatile anesthetic compounds, the semi-fluorinated block copolymer has the formula:

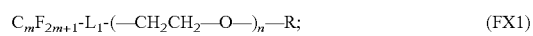

$$C_mF_{2m+1}\text{-}L_1\text{-}(\text{—}CH_2CH_2\text{—}O\text{—})_n\text{—}R; \quad \quad (FX1)$$

wherein m is selected from the range of 5 to 25, n is selected from the range of 10 to 270, $L_1$ is a linking group; and wherein R is a hydrogen, a methyl group, a substituted or unsubstituted alkoxy group, a substituted or unsubstituted alkyl group, a substituted or unsubstituted aryl group, a substituted or unsubstituted alkenyl; or a substituted or unsubstituted alkynyl group. Linking groups ($L_1$) in this aspect function to connect hydrophilic blocks (e.g. PEG) and fluorophilic blocks (e.g., fluorinated alkyl group) of the semifluorinated block copolymers. In an embodiment, the semi-fluorinated block copolymer has the chemical formula FX1, and the linking group ($L_1$) is selected from the group consisting of a substituted or unsubstituted alkyl group, a substituted or unsubstituted alkenyl; and a substituted or unsubstituted alkynyl group. In an embodiment, the linking group ($L_1$) is a $C_{1-10}$ alkyl group. In an embodiment, the semi-fluorinated block copolymer has the formula FX1, wherein R is a hydrogen, methyl group or an alkyl group.

In an embodiment of the present invention particularly useful for delivery of fluorinated volatile anesthetic compounds, the semi-fluorinated block copolymer has the formula:

$$C_mF_{2m+1}\text{-}(CH_2)_p\text{—}O\text{—}(\text{—}CH_2CH_2\text{—}O\text{—})_n\text{—}R; \text{ or} \quad (FX2)$$

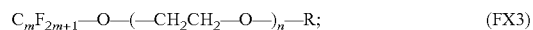

$$C_mF_{2m+1}\text{—}O\text{—}(\text{—}CH_2CH_2\text{—}O\text{—})_n\text{—}R; \quad \quad (FX3)$$

wherein m is selected from the range of 5 to 25, n is selected from the range of 10 to 270, p is selected from the range 1 to 10; and wherein R is a hydrogen, a methyl group, a substituted or unsubstituted alkoxy group, a substituted or unsubstituted alkyl group, a substituted or unsubstituted aryl group, a substituted or unsubstituted alkenyl; or a substituted or unsubstituted alkynyl group. In an embodiment, the semi-fluorinated block copolymer has the formula FX2 or FX3, wherein R is a hydrogen, methyl group or an alkyl group.

Selection of stabilizing additives, such as perhalogenated fluorocarbon compounds, having specific and well defined physical and chemical properties is also important in the present invention for providing therapeutic formulations providing enhanced delivery performance and stability, and for accessing therapeutic emulsions having large concentrations of fluorinated therapeutic compounds, such as emulsions having large concentrations of fluorinated volatile anesthetics. In some embodiments, for example, stabilizing agents are provided that comprise a component of the dispersed droplet phase that controls the release rate of fluorinated anesthetic from the droplets, thereby lowering the rate of droplet ripening processes such as Ostwald ripening. Stabilizing additives of this aspect are useful for providing therapeutic emulsions, including nanoemulsions, exhibiting stable droplets sizes and/or comprising droplets that undergo growth at rates sufficiently low to allow their use a therapeutic agents.

First, stabilizing additives, such as perhalogenated fluorocarbon stabilizing additives, preferably exhibit high fluorophilicity. Exemplary stabilizing additives, such as perhalogenated fluorocarbon stabilizing additives, have a high affinity for the fluorous block of the semifluorinated block copolymer, which leads to a low interfacial tension with the block copolymer. For some applications, the number of fluorine-carbon bonds is an important parameter in selecting a stabilizing additive, such as a perhalogenated fluorocarbon stabilizing additive, having an appropriately high fluorophilicity. Perhalogenated fluorocarbon stabilizing additives having between 12 to 25 carbon-fluorine bonds are desirable for some therapeutic formulations of the present invention. Alternatively, the number of carbon-fluorine bonds of the perhalogenated fluorocarbon stabilizing additive may be appropriately matched or otherwise related to the number of carbon-fluorine bonds of the fluorophilic block of the semifluorinated block copolymers.

Second, stabilizing additives, such as perhalogenated fluorocarbon stabilizing additives, preferably exhibit low solubility in water. Selection of stabilizing additives with low water solubility is useful for avoiding degradation of the present therapeutic emulsion caused by over-ripening of fluorinated therapeutic containing particles dispersed in a continuous aqueous phase. In an embodiment, the stabilizing additive, such as a perhalogenated fluorocarbon stabilizing additive, has a solubility in water less than or equal to 20 nanomolar. The particle ripening rate depends on the solubility of the additive. Accordingly, use of perfluorooctyl bromide (abbreviated as pfob), which has a solubility of 5 nM, provides for slow ripening. In principle, however, an additive that is slightly more water-soluble, for example 20 nM, will also slow the ripening but not as much as fluoroderivatives that are less soluble.

Third, stabilizing additives, such as perhalogenated fluorocarbon stabilizing additives, useful in the present therapeutic formulations are preferably chemically inert. Perfluorinated compounds, bromine substituted perfluorinated compounds and chlorine substituted perfluorinated compounds provide useful chemically inert perhalogenated fluorocarbon stabilizing additives in the present invention.

Fourth, stabilizing additives, such as perhalogenated fluorocarbon stabilizing additives, useful in the present therapeutic formulations preferably are rapidly excreted, for example having a circulatory half-time (i.e., the time for the concentration of perhalogenated fluorocarbon stabilizing additive to decrease by half in the circulation) less than two weeks.

Fifth, stabilizing additives, such as perhalogenated fluorocarbon stabilizing additives, useful in the present therapeutic formulations preferably have a molecular weight selected over the range of 460 amu to 520 amu. Compounds having molecular weights below this range are typically susceptible to having too high a vapor pressure, which can lead to lung emphysema and other pulmonary complications. Compounds having molecular weights below this range typically exhibit excretion times that are undesirably long.

Sixth, stabilizing additives, such as perhalogenated fluorocarbon stabilizing additives, useful in the present therapeutic formulations preferably are provided as high purity reagents. Benefits of the use of high purity reagents are that no toxicity, carcinogenic, mutagenic, teratogenic effects, or immunological reactions, have been reported for many fluorocarbons when provided in a sufficiently pure form and chosen within the appropriate molecular weight range (See above).

Useful perhalogenated fluorocarbon stabilizing additives include perfluorocarbons; bromine substituted perfluorocarbons; chlorine substituted perfluorocarbons; and bromine and chlorine substituted perfluorocarbons. In an embodiment, the perhalogenated fluorocarbon is one or more compounds selected from the group consisting of perfluorooctyl bromide; perfluorononyl bromide, perfluorodecyl bromide, perfluorodecalin; perfluorodichlorooctane; and bis-perfluorobutyl ethylene and perfluoro(methyldecalin). The present invention includes therapeutic formulations comprising a plurality of different perhalogenated fluorocarbon stabilizing additives.

In a therapeutic emulsion of the present invention, droplets dispersed in the continuous phase comprise self assembled supramolecular structures encapsulating the fluorinated therapeutic compound and, optionally the stabilizing agent. In an embodiment, supramolecular structures have an interior fluorous core comprising droplets of fluorinated therapeutic compound and stabilizing agent(s) encapsulated by the semifluorinated block copolymer surfactant. For example, the present invention includes formulations wherein the fluorophilic blocks of semi-fluorinated block copolymer surfactants are oriented toward and/or proximate to the interior fluorous core of the droplet comprising a mixture of fluorinated volatile anesthetic and stabilizing agent; and wherein the hydrophilic block is oriented distal to the interior fluorous core of the droplets (i.e. oriented toward the continuous aqueous phase).

The therapeutic formulations of the present invention include nanoemulsions comprising an aqueous continuous phase and dispersed phase droplets of fluorinated volatile anesthetic and stabilizing agent. In some embodiment, dispersed phase droplets of the nanoemulsion have an average diameter less than 1 micron, for example an average diameter selected from the range of 50 to 1000 nanometers. In some embodiments, dispersed phase droplets of nanoemulsions of the present invention have an average diameter less than or equal to 400 nanometers, for example droplets having average diameter selected over the range of 50 nanometers to 400 nanometers. Use of dispersed phase droplets having an average diameter less than or equal to 400 nanometers is beneficial for minimizing or eliminating toxicity of these droplets upon introduction into the blood stream. In some embodiments, dispersed phase droplets of nanoemulsions of the present invention are substantially homogeneous droplets.

In a therapeutic formulation of the present invention, the fluorinated therapeutic compound has a percentage by volume selected over the range of 5% to 25%, the perhalogenated fluorocarbon stabilizing additive has a percentage by volume selected over the range of 1% to 10%; and the semi-fluorinated block copolymers have a concentration selected over the range of 1 mg ml$^{-1}$ to 45 mg ml$^{-1}$. In a therapeutic emulsion of the present invention providing enhanced delivery performance relative to conventional lipid-base delivery systems the fluorinated therapeutic compound comprises greater than 5% of the volume of the therapeutic emulsion, for example comprising 5% to 30% of the volume of the therapeutic emulsion, and in some embodiments comprising 5% to 25% of the volume of the therapeutic emulsion.

In an embodiment, the fluorinated therapeutic compound is 5% to 25% by volume of the therapeutic formulation, the perhalogenated fluorocarbon stabilizing additive is 1% to 10% by volume of the therapeutic formulation; and the semi-fluorinated block copolymers have a concentration selected over the range of 1 mg ml$^{-1}$ to 45 mg ml$^{-1}$.

In another aspect, methods of administering the therapeutic formulations of the present are provided, including methods of administering therapeutic formulations containing fluorinated volatile anesthetics. In an embodiment, a method of administering a fluorinated therapeutic compound to a patient comprises the steps of: (i) providing a therapeutic formulation comprising: an aqueous solution; semi-fluorinated block copolymers having a hydrophilic block and a fluorophilic block; a fluorinated therapeutic compound; and a stabilizing additive such as a perhalogenated fluorocarbon stabilizing additive; (ii) emulsifying the therapeutic formulation, thereby making a therapeutic emulsion; and (iii) delivering the therapeutic emulsion to the patient. Therapeutic formulations useful for these methods of the present invention include all embodiments, compositions, preparations, phases (e.g., colloidal phases) and variations described above. In an embodiment, the therapeutic emulsion is delivered to the patient via intravenous injection. For example, the present invention includes methods wherein a volume of therapeutic emulsion selected over the range of 1 ml to 100 ml is injected to a patient at a rate selected over the range of 0.1 ml min$^{-1}$ to 20 ml min$^{-1}$, more preferably for some applications a rate selected over the range of 0.1 ml min$^{-1}$ to 5 ml min$^{-1}$. Alternatively, the present invention includes formulation and methods wherein a therapeutic emulsion is delivered to the patient via dialysis, absorption, transdermal delivery, or oral delivery.

In an exemplary embodiment of this aspect of the present invention the step of emulsifying the therapeutic formulation comprises the steps of: (i) adding the fluorinated therapeutic compound and the stabilizing additive, such as a perhalogenated fluorocarbon stabilizing additive, to the aqueous solution having the semi-fluorinated block copolymers therein, thereby generating a therapeutic mixture; and (ii) homogenizing the therapeutic mixture, thereby generating the therapeutic emulsion. Optionally, this method of the present invention further comprises the step of lowering the temperature of the therapeutic mixture during the homogenizing step. The step of homogenizing the therapeutic mixture may be carrier out by any means known in the art of colloid science and pharmacology including using a lower energy mixer and/or a microfluidizer. In some embodiments, a portion or all of the components of the therapeutic formulation are mixed below the critical micellar concentration. The temperature is subsequently lowered, the concentration of semifluorinated block copolymer is subsequently raised and/or other solution condition(s) is changed so as to initiate formation of supramolecular structures encapsulating the fluorinated therapeutic compound.

In another aspect, the present invention provides a method of making a therapeutic emulsion containing a fluorinated therapeutic compound comprising the steps of: (i) providing a therapeutic formulation comprising: an aqueous solution; semi-fluorinated block copolymers having a hydrophilic block and a fluorophilic block; a fluorinated therapeutic compound; and a stabilizing additive, such as a perhalogenated fluorocarbon stabilizing additive; and (ii) emulsifying the therapeutic formulation, thereby making the therapeutic emulsion.

Alternatively, the present include methods of making a therapeutic emulsion containing a fluorinated therapeutic compound, wherein an aqueous solution containing supramolecular structures, such as micelles, comprising the present block copolymers is provided. Next, the stabilizing additive, such as a perhalogenated fluorocarbon stabilizing additive, and fluorinated therapeutic compound are added and taken up by the preformed micelles, thereby resulting in a therapeutic formulation.

In another aspect, the present invention provides a method of stabilizing a therapeutic emulsion containing a fluorinated therapeutic compound, comprising the steps of: (i) providing a therapeutic formulation comprising: an aqueous solution; semi-fluorinated block copolymers having a hydrophilic block and a fluorophilic block; and a fluorinated therapeutic compound; (ii) adding a stabilizing additive, such as a perhalogenated fluorocarbon stabilizing additive, to said therapeutic formulation; and (iii) emulsifying said therapeutic formulation, thereby stabilizing said therapeutic emulsion.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

BRIEF DESCRIPTION OF THE DRAWINGS

FIG. 5 provides data corresponding to a time interval of approximately 15 days. It is noted that FIG. 18 provides a similar plot, including this data, wherein additional data is provided corresponding to a time interval extended to approximately 50 days.

FIG. 6 provides data corresponding to a time interval of approximately 3 days. It is noted that FIG. 17 provides a similar plot, including this data, wherein additional data is provided corresponding to a time interval extended to approximately 50 days.

FIG. 12 provide plots showing the Maximum amount of sevoflurane that can be stably emulsified. All emulsions contain 8% v/v perfluorooctyl bromide and 2.5% w/v F13M5.

FIG. 22 A shows a plot of droplet diameter as a function of time for perfluorooctyl bromide (pfob) percentages by volume ranging from 1% to 10%. FIG. 22 B shows a plot of ripening rate as a function of amount of additive. In these experiments the emulsions contain 20% by volume sevflurane and 1.5% weight by volume of the semifluorinated block copolymer surfactant F13M5.

DETAILED DESCRIPTION OF THE INVENTION

Figure 1:
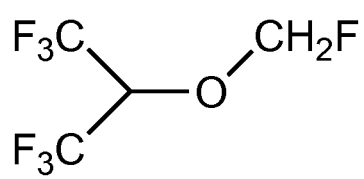
FIG. 1 provides chemical structures of common volatile general anesthetics.
Figure 1:
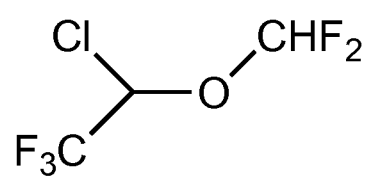
Figure 1:
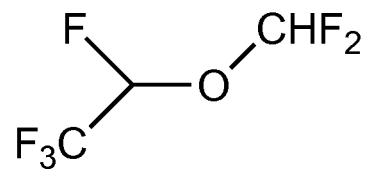

Referring to the drawings, like numerals indicate like elements and the same number appearing in more than one drawing refers to the same element. In addition, hereinafter, the following definitions apply:

"Supramolecular structure" refers to structures comprising an assembly of molecules. Supramolecular structures include assemblies of molecules, such as block copolymers having hydrophilic and fluorophilic blocks, which are selectively oriented such that hydrophilic portions of the molecules is oriented outward toward a continuous aqueous phase and such that fluorophilic portions of the molecules are oriented inward toward a fluorous inner core of the supramolecular structure. Supramolecular structures include, but are not limited to, micelles, vesicles, tubular micelles, cylindrical micelles, bilayers, folded sheets structures, globular aggregates, swollen micelles, and encapsulated droplets. Supramolecular structures of the present invention include self assembled structures. Supramolecular structures may comprise the dispersed phase of a colloid, such as an emulsion or nanoemulsion.

"Semi-fluorinated" refers to chemical compounds having at least one fluorine atom, for example molecules having at least one carbon-fluorine bond.

Fluorocarbons as used herein refer to chemical compounds that contain at least one carbon-fluorine bond. Many volatile anesthetics, such as sevoflurane, isoflurane, desflurane, enflurane and methoxyflurane, are fluorocarbons.

"Perfluorinated" and "perfluorocarbon" refers to chemical compounds that are analogs of hydrocarbons wherein all hydrogen atoms in the hydrocarbon are replaced with fluorine atoms. Perfluorinated molecules can also contain a number of other atoms, including bromine, chlorine, and oxygen. A bromine substituted perfluorocarbon is a perfluorocarbon wherein one or more of the fluorine atoms have been replaced with a bromine atom. A chlorine substituted perfluorocarbon is a perfluorocarbon wherein one or more of the fluorine atoms have been replaced with a chlorine atom. A chlorine and bromine substituted perfluorocarbon is a perfluorocarbon wherein one or more of the fluorine atoms have been replaced with a chlorine atom and wherein one or more of the fluorine atoms have been replaced with a bromine atom.

"Emulsion" refers to a mixture of two or more immiscible substances, such as a mixture of two immiscible liquids. Emulsions are a type of colloid that comprise at least one dispersed phase dispersed in a continuous phase. Emulsions are broadly defined as two immiscible phases dispersed within another, such as a two-phase system in which one liquid is dispersed throughout another liquid in the form of small droplets. This energy can either be supplied by mechanical equipment or the chemical potential inherent within the components. The two phases of an emulsion are generally referred to as the continuous phase and the dispersed phase, with the dispersed phase typically present as a smaller volume percentage. A dispersion of oil in water is referred to as an oil-in-water (o/w) emulsion. For o/w emulsions the emulsifying agent is typically more soluble in the aqueous phase. The reverse emulsion, water-in-oil, is abbreviated w/o and is stabilized by surfactants that are more stable in the oil phase. In an aqueous emulsion, the continuous phase is an aqueous solution.

Emulsions are not thermodynamically stable, but the stability can be improved by additives such as surfactants. As non-equilibrium systems, the formation of nanoemulsions generally requires an input of energy. High-energy emulsification methods commonly involve the introduction of mechanical shear through such equipment as high-shear stirrers, high-pressure homogenizers, microfluidizers or ultrasound generators. A microfluidizer is the piece of equipment used in the pharmaceutical industry for the production of emulsions that works by dividing a stream of liquid into two parts, passing each through a narrow opening and then colliding the streams under high pressure. The high shear forces created by the collision provide very fine emulsions with generally narrow particle size distributions. In typical usage, a coarse emulsion (diameter >1 μm) is first formed by some other method, and the size of that larger emulsion is reduced in the microfluidizer. The final droplet size and distribution shape will be dependent upon both the emulsion components (surfactant amount, oil volume percent, etc.) and the processing parameters (time, temperature, pressure etc.). As the desired droplet size decreases, the energy required for formation increases. Ultrasonic emulsification is also effective to reduce the size of emulsion droplets into the nanoscale. Emulsion can also be formed by changing the temperature of a mixture of immiscible liquids, for example by rapid cooling or heating to produce kinetically stable emulsions with small droplet sizes and narrow size distributions.

Emulsion includes nanoemulsions comprising nanoscale droplets of one immiscible liquid dispersed within another. As used herein a nanoemulsion is a heterogeneous system composed of one immiscible liquid dispersed as droplets within another liquid, where the average droplet diameter is below 1000 nm.

"Flocculation" refers to a process in which clusters of two or more droplets behave kinetically as a unit, but individual droplets still maintain their identity. Flocculation may be reversible, or lead to coalescence, which is irreversible.

"Coalescence" is the collision, and subsequent irreversible fusion, of two droplets. The ultimate end of coalescence is complete phase separation. Flocculation precedes coalescence, so the same methods that are appropriate for prevention of flocculation also prevent coalescence. A thick, surfactant film adsorbed at the interface is often sufficient to prevent coalescence, whether in nano- or macroemulsions.

"Ostwald ripening" refers to the growth in the size of emulsion droplets as the contents of one drop diffuse into another. The driving force for this growth is the difference in chemical potential between droplets, which is generally not substantial for droplets larger than 1 μm. Therefore, Ostwald ripening primarily affects nanoemulsions, and is an important factor for nanoemulsions for therapeutic applications.

"Polymer" refers to a molecule comprising a plurality of repeating chemical groups, typically referred to as monomers. A "copolymer", also commonly referred to as a heteropolymer, is a polymer formed when two or more different types of monomers are linked in the same polymer. "Block copolymers" are a type of copolymer comprising blocks or spatially segregated domains, wherein different domains comprise different polymerized monomers. In a block copolymer, adjacent blocks are constitutionally different, i.e. adjacent blocks comprise constitutional units derived from different species of monomer or from the same species of monomer but with a different composition or sequence distribution of constitutional units. Different blocks (or domains) of a block copolymer may reside on different ends of a polymer (e.g. [A][B]), or may be provide in a selected sequence ([A][B][A][B]). "Diblock copolymer" refers to block copolymer having two different chemical blocks. Polymers of the present invention include block copolymers having a first block comprising a smaller polymer (e.g., 2 to 30 monomers), such as a fluorocarbon, including but not limited to, a fluorocarbon such as a fluorinated or perfluorinated alkane, and a second block comprising a larger polymer (e.g., 10-300) such as a PEG polymer having 10 to 270 monomers. Block copolymers of the present invention are capable of undergoing self assembly to make supramolecular structures, such as encapsulated droplets and micelles. As used herein, the term block copolymer includes compositions comprising a first block comprising a PEG polymer conjugated to a second block comprising a perfluorinated or semifluorinated molecular domain, such as a perfluorinated or semifluorinated alkane or a perfluorinated or semifluorinated tail. As used herein, the term block copolymer also include functionalized block copolymers, such as copolymer having additional moieties for targeting a supramolecular structure to an active site, for stabilizing a supramolecular structure or for selecting the release kinetics of a supramolecular structure containing a fluorinated therapeutic compound. As used herein, the abbreviation FXMY is used to refer to semifluorinated block copolymers having perfluorinated alkane and polyethylene glycol components, wherein FX refers to a perfluorinated alkane block having X carbons and MY refers to a PEG block having an molecular weight equal to Y thousand (i.e., Y,000) amu.

As used herein "hydrophilic" refers to molecules and/or components (e.g., functional groups, block of block polymers etc.) of molecules having at least one hydrophilic group, and hydrophobic refers to molecules and/or components (e.g., functional groups of polymers, and blocks of block copolymers etc.) of molecules having at least one hydrophobic group. Hydrophilic molecules or components thereof tend to have ionic and/or polar groups, and hydrophobic molecules or components thereof tend to have nonionic and/or nonpolar groups. Hydrophilic molecules or components thereof tend to participate in stabilizing interactions with an aqueous solution, including hydrogen boding and dipole-dipole interactions. Hydrophobic molecules or components tend not to participate in stabilizing interactions with an aqueous solution and, thus often cluster together in an aqueous solution to achieve a more stable thermodynamic state. In the context of block copolymer of the present invention, a hydrophilic block is more hydrophilic than a hydrophobic group of an amphiphilic block copolymer, and a hydrophobic group is more hydrophobic than a hydrophilic block of an amphiphilic polymer.

As used herein "fluorophilic" refers to molecules and/or components (e.g., functional groups, blocks of block polymers etc.) of molecules having at least one fluorophilic group. A fluorophilic group is one that is capable of participating in stabilizing interactions with a fluorous phase. Fluorophilic groups useful in block copolymers of the present invention include, but are not limited to, fluorocarbon groups, perfluorinated groups and semifluorinated groups.

In the context of the present invention the term patient is intended to include a subject such as an animal. Patient includes a mammal, for example human subject. Patient includes a subject undergoing a medical procedure, such as undergoing the administration of anesthesia or other medical procedure.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group linked to oxygen and can be represented by the formula R—O.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:
- —COOR where R is a hydrogen or an alkyl group or an aryl group and more specifically where R is methyl, ethyl, propyl, butyl, or phenyl groups all of which are optionally substituted;
- —COR where R is a hydrogen, or an alkyl group or an aryl groups and more specifically where R is methyl, ethyl, propyl, butyl, or phenyl groups all of which groups are optionally substituted;
- —CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds.
- —SR, —SO$_2$R, or —SOR where R is an alkyl group or an aryl groups and more specifically where R is methyl, ethyl, propyl, butyl, phenyl groups all of which are optionally substituted; for —SR, R can be hydrogen;
- —OCOOR where R is an alkyl group or an aryl groups;

—SO$_2$N(R)$_2$ where R is a hydrogen, an alkyl group, or an aryl group and R and R can form a ring;

—OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted;

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The present invention provides therapeutic formulations, including therapeutic emulsions and nanoemulsions, for delivering fluorinated therapeutic compounds, that are well suited for the intravenous administration of fluorinated volatile anesthetics. Supramolecular delivery systems are provided for encapsulating, stabilizing and delivering droplets of fluorinated therapeutic compounds to the blood stream and/or active sites in an organism. At the same time, an internal fluorous phase acts as a recognition element for highly fluorinated molecule. The present semifluorinated block copolymer stabilized emulsions, including present semifluorinated block copolymer stabilized nanoemulisons, are an ideal vector for encapsulating fluorinated molecules, such fluorinated volatile anesthetics, and for providing clinical administration and delivery.

The present invention provides novel drug delivery systems that are based on the self-association properties of fluorinated molecules. Experimental results show that emulsions stabilized by semi-fluorinated polymers are able to encapsulate highly fluorinated, low boiling-point anesthetics. Experimental results also demonstrate that the present block copolymers are capable of solubilizing large amounts of fluorinated volatile anesthetics in water as nanoemulsions. Electrophysiology-based binding experiments on the GABAA receptor indicate that the concentration of anesthetic released by the present nanoemulsions may be enough to induce and maintain anesthesia in human patients. A principal advantage of the present emulsion-based formulations is that they allow intravenous delivery of volatile anesthetics. Accordingly, formulations of the present invention provide a viable alternative to vapor inhalation in general anesthesia and, thus has significant application in a range of important clinical settings. More specifically, the present block copolymer surfactants having a combination of hydrophilic and fluorophilic domains are capable of directly binding and safely delivering anesthetics such as isoflurane and sevoflurane by intravenous injection rather than by either intranasal or transdermal delivery. This aspect of the present invention is beneficial, as intravenous delivery of fluorinated anesthetics permits anesthetic levels to be deepened rapidly without the need to hyperventilate patients and without the use of irritating agents such as desflurane.

Nanoemulsion-based formulations of the present invention allow incorporation of large amounts of fluorinated volatile anesthetics, such as up to 25% by volume. In contrast, previous data published in the literature and referring to the ability of the lipid emulsion known as Intralipid™ (a mixture of various lipids) to deliver intravenously fluorinated anesthetics, indicate that the maximum concentration of anesthetic (sevoflurane) achievable with non-fluorinated surfactants/lipids is only 3.6%. (See, Eger, R. P.; Macleod, B. A. "Anesthesia by Intravenous Emulsified Isoflurane in Mice" *Can. J. Anesth.* 1995, 42, 173-176; and Zhou, J.-X.; Luo, N.-F.; Liang, X.-M.; Liu, J. "The Efficacy and Safety of Intravenous Emulsified Isoflurane in Rats" *Anesth. Analg.* 2006, 102, 129-134).

The possibility of preparing extremely concentrated emulsions of anesthetic enables highly effective clinical use of the present formulations. A single injection of 30 mL of the present therapeutic emulsion formulation is enough to induce anesthesia in a human patient. Maintenance of anesthesia is then achievable by simple slow IV infusion of the present therapeutic formulations. Conventional Intralipid formulations cannot currently be used in human patients because large volumes are expected to be required to achieve effective anesthetic results.

The present nanoemulsions are optionally stabilized by the addition of a stabilizing additive. Perfluorooctyl bromide and perfluorodecalin are effective stabilizers in terms of nanoparticle size and anesthetic concentration in the present invention. It is noteworthy that perfluorooctyl bromide and perfluorodecalin are approved for human use in large concentrations by the FDA.

Experimental results show that the present therapeutic formulations safely and very quickly induce anesthesia in rats. The ability of exactly dosing the amount of anesthetic given via intravenous delivery, compared to classical inhalation, allows the subject to be provided with only the amount of anesthetic needed for a certain duration of anesthesia. In these conditions, recovery from general anesthesia is very rapid, eliminating problems due to the accumulation of unused anesthetic in various tissues, which is a problem that always accompanies general anesthesia by inhalation.

In the some embodiments, perfluorinated molecular domains of block copolymer surfactants are used as elements for directing and enhancing the self-assembly of regular supramolecular structures useful for making an stabilizing fluorinated volatile anesthetic containing nanoemulsions. For example, the fluorinated polymers of the present invention greatly reduce the interfacial tension with fluorinated liquids. Importantly, the reduction of interfacial tension is one of the elements for providing a stable emulsion.

The enhanced stability of the nanoemulsions during long term storage is also an important attribute of the present emulsion-based therapeutic formulations. The present formulations are capable of being provided to the anesthesiologist as fully formed emulsions. In these embodiments, it is useful that the size of the nanodroplets in these emulsions does not change rapidly with time. Strategies of the present invention to suppress ripening of nanodroplets of emulsions of the present invention include the addition of a perhalogenated fluorocarbon stabilizing additive, such as perfluorooctyl bromide, prevents suppresses the rate of ripening of the encapsulated nanodroplets, for example via Ostwald ripening.

The present therapeutic formulations include compositions having different stabilizing additives. In some formulations and methods of the present invention, for example, the stabilizing additive perfluorooctyl bromide (PFOB) is replaced with perfluorodecyl bromide (PFDB). The lower water solubility of PFDB (0.05 nM) compared to the water solubility of PFOB (5.1 nM) results in larger emulsion stabilization by PFDB than for PFOB. Both PFDB and PFOB are FDA approved for use in human patients. PFDB has also been used as an additive to stabilize oxygen emulsions in fluorocarbons.

Figure 2:
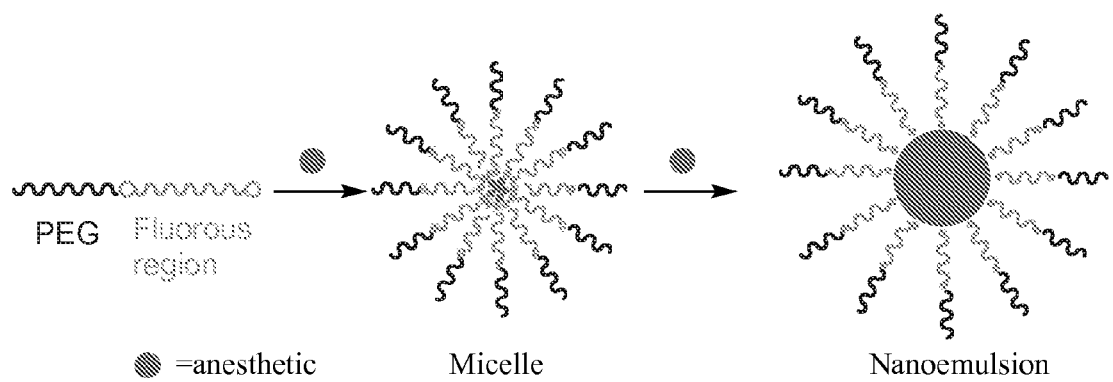
FIG. 2 provides a schematic diagram illustrating transition from micelles to emulsions in the binding of fluorinated anesthetics by semi-fluorinated polymers.

In some aspects, the present therapeutic delivery approach is based on formation of nanoemulsions. In some embodiments, nanoemulsions of the present inventions comprise particles where the inner core is composed of a droplet of anesthetic with diameter less than 1 μm. FIG. 2 provides a schematic diagram illustrating: (i) formation of micelle supramolecular structures encapsulating anesthetic using the present block copolymers having hydrophilic and fluorophilic blocks, and (ii) transition of the micelle supramolecular structures into a nanoemulsion. As shown in the Figure, the droplets are surrounded and stabilized by a layer of block copolymer molecules. In an embodiment, the polymer is organized around the droplets in such a way that its fluorophilic region is in contact with the fluorophilic core of anesthetic. The nanoemulsions generated by mixing volatile anesthetics with our fluoropolymers are more stable at high anesthetic concentrations and are more homogenous in size than the emulsions prepared by using a non-fluorinated lipid. This aspect of the present invention allows extremely large amounts of anesthetic, up to 25% in volume, to be solubilized. It is also worth noticing that the use of stable nanoemulsions is particularly indicated for intravenous injections or infusions as it reduces the risks of cardiovascular blockages.

Methods of this invention comprise the step of administering a "therapeutically effective amount" of the present therapeutic formulations containing fluorinated volatile anesthetics, including therapeutic emulsions, to establish, maintain and/or regulate anesthesia in a patient. The term "therapeutically effective amount," as used herein, refers to the amount of the therapeutic formulation, that, when administered to the individual is effective to establish and, optionally maintain or regulate anesthesia or sedation in a patient. As is understood in the art, the therapeutically effective amount of a given compound or formulation will depend at least in part upon, the mode of administration (e.g. intraveneous administration), any carrier or vehicle employed, and the specific individual to whom the formulation is to be administered (age, weight, condition, sex, etc.). The dosage requirements need to achieve the "therapeutically effective amount" vary with the particular formulations employed, the route of administration, and clinical objectives. Based on the results obtained in standard pharmacological test procedures, projected daily dosages of active compound (e.g. fluorinated volatile anesthetic) can be determined as is understood in the art.

Any suitable form of administration can be employed in connection with the therapeutic formulations of the present invention. The therapeutic formulations of this invention can be administered intravenously, in oral dosage forms, intraperitoneally, subcutaneously, or intramuscularly, all using dosage forms well known to those of ordinary skill in the pharmaceutical arts.

The therapeutic formulations of this invention can be administered alone, but may be administered with a pharmaceutical carrier selected upon the basis of the chosen route of administration and standard pharmaceutical practice.

The therapeutic formulations of this invention and medicaments of this invention may further comprise one or more pharmaceutically acceptable carrier, excipient, or diluent. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985), which is incorporated herein by reference in its entirety.

This invention additionally relates to the use of semi-fluorinated block copolymers, fluorinated therapeutic compounds and perhalogenated fluorocarbon stabilizing additives in the manufacture of a medicament for anesthesia. More specifically, the invention relates to the use of semi-fluorinated block copolymers having a hydrophilic block and a fluorophilic block, fluorinated therapeutic compounds and perhalogenated fluorocarbon stabilizing additives in the manufacture of a medicament for anesthesia. In specific embodiments the medicament manufactured is in the form of an emulsion, such as a nanoemulsion, for intravenous administration. In specific embodiments, the medicament further comprises a pharmaceutically acceptable carrier or diluent and particularly a carrier or diluent suitable for intravenous administration.

Example 1

Emulsion-Based Therapeutic Formulations for the Delivery of Fluorinated Therapeutic Compounds The physical and chemical properties of organic compounds are deeply affected by the introduction of fluorine substituents. While the introduction of one single atom of fluorine in an organic molecule can already change the properties of a molecule, perfluorination of organic molecules can generate a new phase of liquid matter, the so-called fluorous phase. This phase does not mix with both polar and non-polar hydrogenated phases. The formation of a fluorous phase is at the origin of the unusual behavior of heavily fluorinated molecules and polymers. Perfluorinated polymers have a low surface energy, they are both lipo- and hydrophobic, and they are unsurpassed in their high chemical and thermal stabilities. Their potential for drug delivery has only recently started to be explored. Most importantly, a host of fluorinated molecules, from fluorinated steroids (used as anti-inflammatory drugs), to fluorinated nucleotides and nucleosides, to volatile anesthetics are now part of the repertoire of drugs available to the physician.

Fluorinated molecules have revolutionized anesthesia. The fluorinated group of anesthetics illustrates the use of fluorine substitution for the development of safer therapeutic agents. Today, desflurane and sevoflurane are used in half the general anesthetics supplied in North America. Molecular recognition of highly fluorinated molecules such as sevoflurane is extremely challenging as fluorinated compounds are hyperhydrophobic and do not mix with both hydrophilic and hydrophobic components. As an example, perfluorooctane does not mix with water or octane and a mixture of these three compounds produces separation into three phases.

Perfluorinated molecules and molecules containing perfluorinated alkyl chains appear to combine two properties that are usually considered antinomic: hydrophobicity and lipophobicity. The situation is different when fluorinated amphiphilic molecules are considered. Due to the increased hydrophobicity of perfluoro-derivatives and to the concomitant presence of water-solubilizing groups, these amphiphiles form a special class of surfactants. Fluorinated surfactants are characterized by a high surface activity and a strong tendency to self-organize into ordered, stable supramolecular complexes. Microtubules, vesicles, bilayers and complex three-dimensional ordered assemblies can be formed by organic molecules bearing perfluorinated substituents. These complexes and the corresponding multi-phase colloidal systems are useful in the present invention as novel drug delivery systems able to protect sensitive drugs from the surrounding environment.

A principal goal of the present therapeutic formulations for delivery of fluorinated volatile anesthetics is use in vivo for inducing and maintaining general anesthesia. In vivo and in vitro results show that the fluorocarbon moiety in the block copolymers of the present invention does not have any intrinsic toxic action.

1.a. Synthesis and Physical-Chemical Characterization of a Series of Semifluorinated Polymers for the Intravenous Delivery of Volatile Anesthetics.

Surfactants or surface-active agents are able to lower the surface tension of the medium in which they are by selective absorption at the interface. Surfactants are by definition amphiphilic, that is, they consist of two different parts widely differing in solubility properties. One part is solvophilic and the other is solvophobic. Conventional water-soluble amphiphilic molecules contain a charged or polyoxygenated moiety for water solubility and a hydrocarbon or fatty acid derivative part that ensures hydrophobicity. The shape, size and nature of these two different parts determine the aggregation properties of the surfactant. Carefully changing parameters such as relative size of the two parts, sterical hindrance of hydrocarbon chain substituents and addition of polar functionalities can lead to the design of molecules that specifically self-assemble in solution. Function, described by the properties of these supramolecular structures, such as micelles, then emerges as the result of selective self-assembly.

Therapeutic formulations and methods of the present invention include, but are not limited to, the class of semifluorinated diblock copolymers comprising a water-solubilizing and biocompatible poly(ethylene glycol) (PEG) domain coupled to a fluorocarbon domain. In an embodiment, the semifluorinated diblock copolymers have the formula:

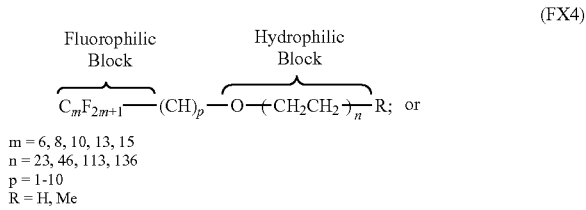

(FX4)

$m = 6, 8, 10, 13, 15$
$n = 23, 46, 113, 136$
$p = 1-10$
$R = H, Me$

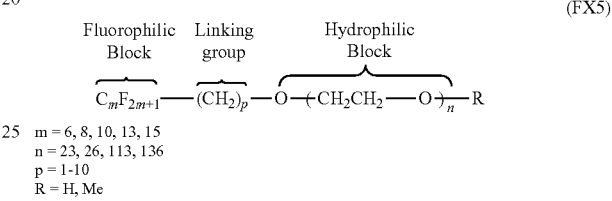

(FX5)

$m = 6, 8, 10, 13, 15$
$n = 23, 26, 113, 136$
$p = 1-10$
$R = H, Me$

In a specific embodiment, the semifluorinated diblock copolymers of this embodiment have the formula FX4 or FX5, wherein p is equal to 1 or 2.

Scheme 1 provides an example synthetic pathway for making semi-fluorinated block polymers of the present invention.

Scheme 1. Synthesis of semi-fluorinated polymers.

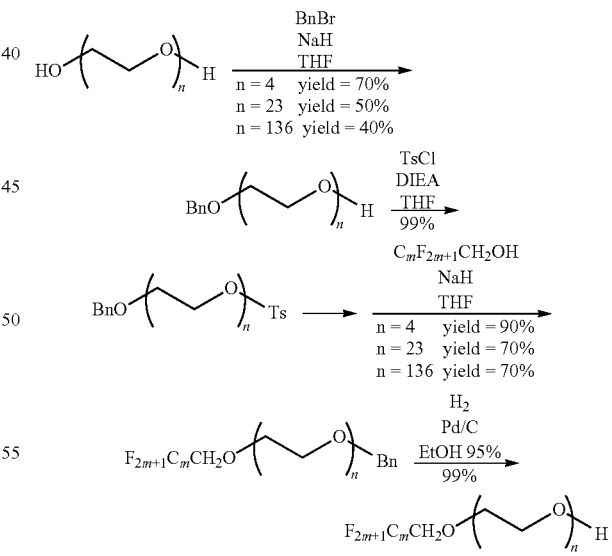

A second more efficient synthetic pathway for making the semi-fluorinated block copolymers of the present invention is shown in Scheme 2. an example of this process makes use of monomethylated PEG with a molecular weight of 5,000 (M5). We have used this synthesis to prepare polymers F8M5, F10M5, F13M1, F13M2, F13M5, and F15M5 (Scheme 2) that have been further characterized and used for preliminary encapsulation and stability studies. This high-yield, two-steps synthesis is promising for the commercial development of these compounds.

Scheme 2. Optimized synthesis for polymers of the FXMY series.

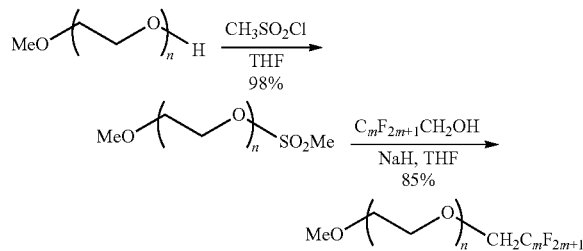

As used herein, the abbreviation FXMY is used to refer to compounds of scheme 2, wherein FX refers to a perfluorinated alkane block having X carbons and MY refers to a PEG block having an molecular weight equal to Y thousand (i.e., Y,000) amu.

The general synthetic methodology used to make these polymers shown in scheme 2. All the needed perfluoro-alcohols are commercially available (Aldrich and Synquest laboratories). Purification of $C_8F_{17}$—$CH_2$—O—($CH_2$—$CH_2$—O)$_{136}$—OH, F8M5, F10M5, and F15M5 is challenging due to their unusual self-assembling and solubility properties. We succeeded in the purification of these polymers by using a combination of polymer precipitation and traditional column chromatography. This procedure has proven effective for all synthesized semifluorinated polymers.

Polymers F8M5, F10M5, F13M5 and F15M5 (See, scheme 2) as well as molecules having the general composition $C_8F_{17}$—$CH_2$—O—($CH_2$—$CH_2$—O)$_{136}$—OH (See, scheme 1) have been studied to experimentally verify the solubility of these molecules and the nature of the aggregates that they can form. We have done this by studying solutions of polymer at different concentrations by dynamic light scattering and fluorescence correlation spectroscopy.

1.b. Nano-Emulsions Containing Fluorinated Volatile Anesthetic

Figure 3:
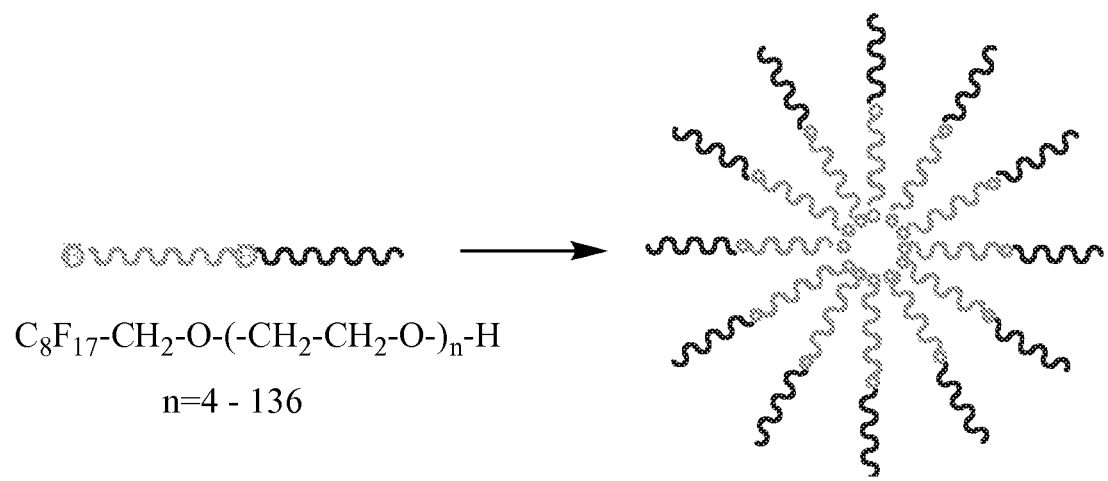
FIG. 3 provides a schematic diagram illustrating the self-assembly of a micelle in aqueous solution.

The semiflourinated block copolymers of the present invention undergo self assembly in aqueous solution by forming an internal fluorous phase between their fluorinated parts. FIG. 3 provides a schematic diagram illustrating the self-assembly of a semiflourinated block copolymers of the present invention, thereby making a micelle structure in solution. While a formulation with polymers alone form micelles, addition of the anesthetic leads to suspension of submicron droplets, a nanoemulsion. We also found that these fluorinated nanoemulsions are stabilized by the addition of an additive such as perfluorooctyl bromide.

Figure 4:
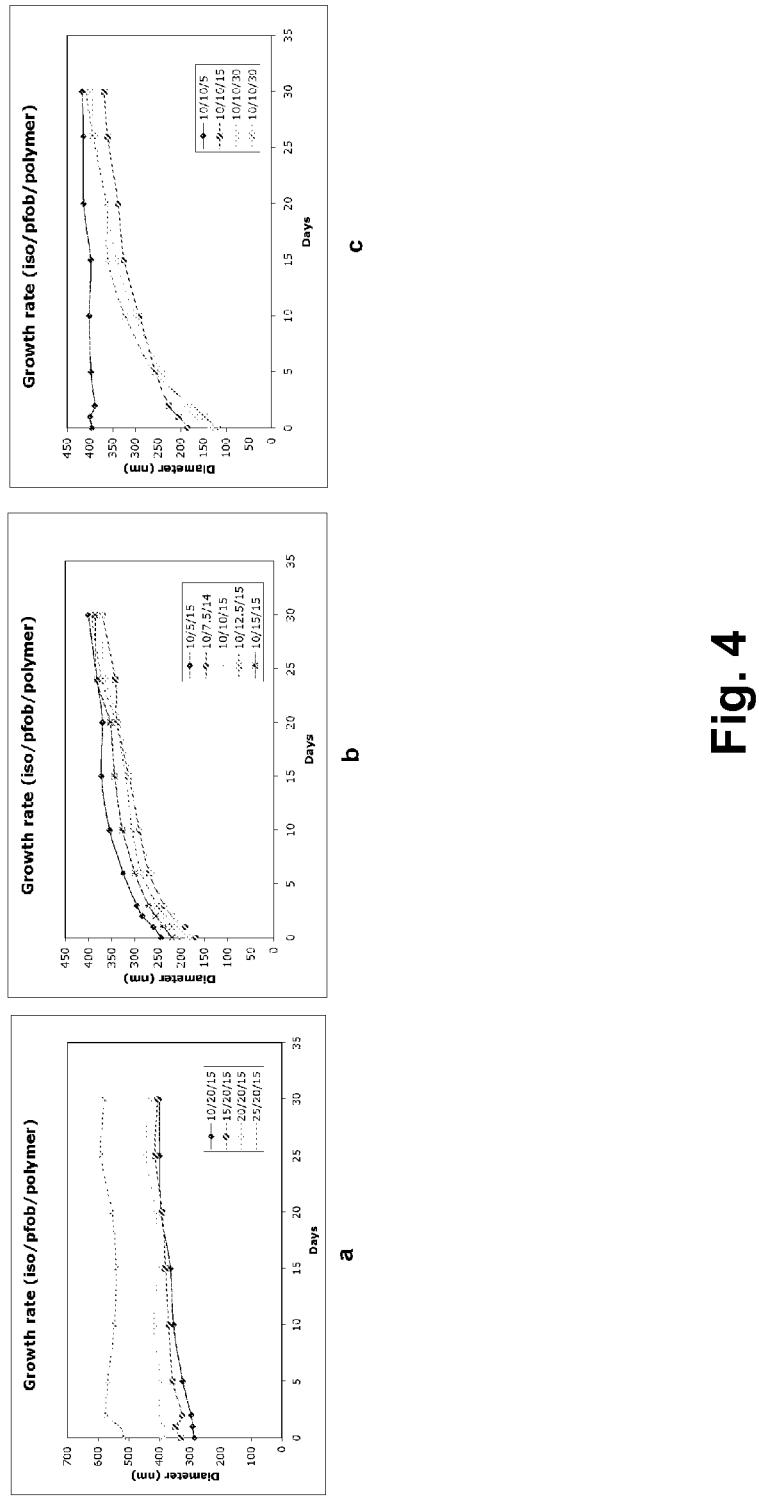
FIG. 4 provides plots showing the effects on the size of the nanoparticles upon changing the concentration of: a. The anesthetic (isoflurane). b. The stabilizing additive. c. The fluoropolymer. Concentrations of isoflurane and perfluorooctyl bromide are in % V/V. Concentrations of the polymers are in mg/mL. iso=isoflurane, pfob=perfluorooctyl bromide. Y axis=diameter (nm), X axis=time (days). Droplet diameter in nanometers is plotted (y-axis) versus time (days).

The stability of both the fluoropolymers and the present anesthetic emulsions may be evaluated by measurement of changes in the size of the nanoparticles over time. FIG. 4 provides plots illustrating the effects on the size of the nanodroplet of an emulsion of the present invention observed upon changing various system parameters. In FIG. 4a, the concentration of the anesthetic (isoflurane) was systematically changed. In FIG. 4b, the concentration of the stabilizing additive (perfluorooctyl bromide) was systematically changed. In FIG. 4a, the concentration of the semifluorinated block copolymer surfactant was systematically changed. Concentrations of isoflurane and perfluorooctyl bromide are in % V/V. Concentrations of the polymers are in mg/mL.

iso=isoflurane, pfob=perfluorooctyl bromide. Y axis=diameter (nm), X axis=time (days). The graphs in FIG. 4 clearly show that our formulations are quite stable.

Figure 5:
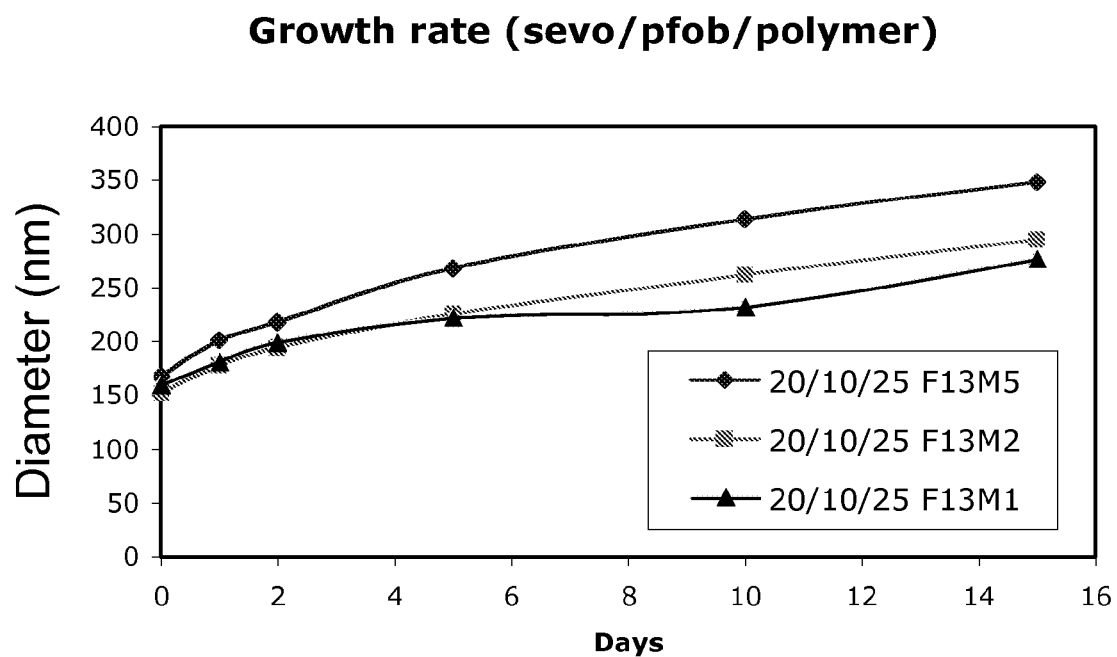
FIG. 5 provides plots showing the effect on the size of the nanoparticles upon changing the size of the PEG and keeping everything else constant. Droplet diameter in nanometers is plotted (y-axis) versus time (days).

An additional study was done by changing the size of the PEG domain of the semifluorinated block copolymer surfactant of the emulsion. FIG. 5 provides plots illustrating the effects on the size of the nanoparticles upon changing the size of the PEG and keeping everything else constant. (Refer to Scheme 2 for the polymer nomenclature). The y axis is FIG. 5 is the size of the droplets in nanometers and the x axis is time in days.

1.c. Use of Perhalogentated Fluorocarbon Stabilization Additives.

In some embodiments, the present therapeutic formulations comprise one or more perhalogentated fluorocarbon stabilization additives, such as perfluorooctyl bromide, to enhance stability and delivery performance. Useful physical and chemical properties of additives in the present formulations include:

a. High fluorophilicity: The additive should have a high affinity for the fluorous block of the stabilizing polymer, which leads to a low interfacial tension with the polymer.

b. Low water solubility: Additives should have sufficiently low water solubility. Ripening is directly related to water solubility. The less water the additive, the slower ripening will occur. Perfluorooctyl bromide has a solubility of 5.1 nm. In some embodiments, therefore, additives have water solubility on the nanomolar range or lower.

c. Chemical inertness: Additives should be sufficiently chemically inert. Perfluorinated compounds tend to be very chemically inert. Also, because of the strong electron withdrawing character of a perfluorinated block, other halogen atoms (bromine or chlorine) on the additive tend to be unreactive.

d. Rapid excretion: Additives should be capable of rapid excretion. Fluorocarbons investigated for blood substitute emulsions were deemed to be acceptable if the circulatory half-time (the time for the PFC concentration to decrease by half in the circulation) was less than two weeks. Perfluorooctyl bromide has a half life in the body of four days. Other suitable candidates include, but are not limited to, perfluorodecalin (7 days), perfluorodichlorooctane (7 days), bis-perfluorobutyl ethylene (7 days) and perfluoro(methyldecalin) (11 days).

e. Appropriate molecular weight: IN some embodiments, additives have a molecular weight selected from the mass range of 400-600 amu, and preferably for some applications a molecular weight selected from the mass range of 460-520 amu. Below this range the vapor pressure may be too high, which can lead to lung emphysema and other pulmonary complications. Above this range the excretion time may be too long.

f. High purity: Additives should be provided as high purity reagents. No toxicity, carcinogenic, mutagenic, or teratogenic effects, nor immunological reactions, have ever been reported for fluorocarbons when pure and chosen with the appropriate molecular weight range.

Figure 6:
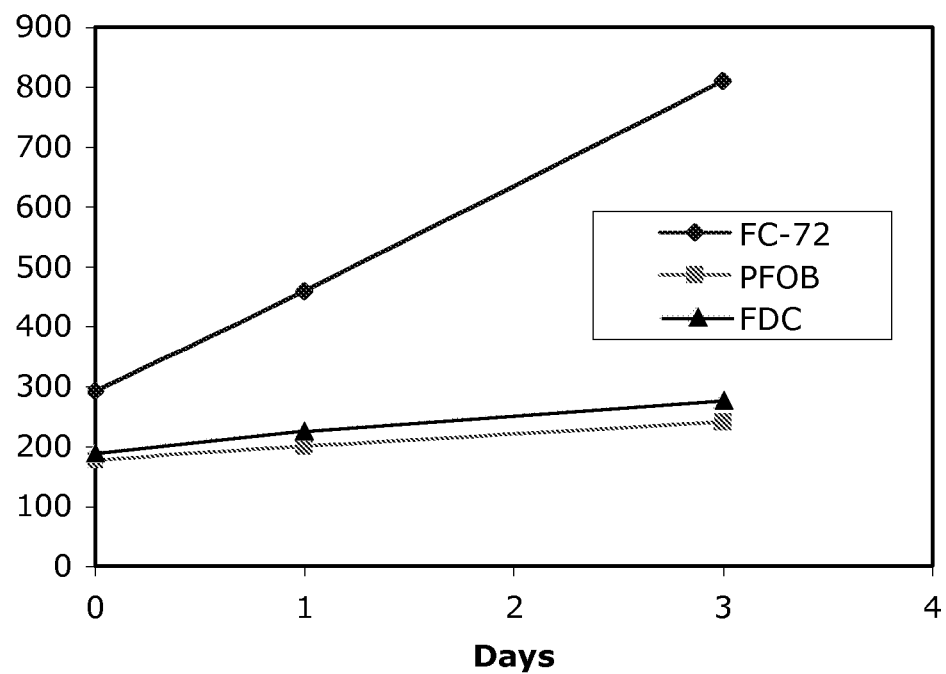
FIG. 6 provides plots of effects on the size of the nanoparticles upon changing the stabilizing additive. Concentrations of the three emulsion constituents are 20/20/15 (sevoflurane/stabilizing additive/F13M5). FC-72=perfluorohexanes, PFOB=perfluorooctyl bromide, FDC=perfluorodecalin. Droplet diameter in nanometers is plotted (y-axis) versus time (days).

In some experimental studies, perfluoroctyl bromide was chosen as an additive for the stabilization of our emulsions because it is FDA approved for use in human patients. FIG. 6 shows the effects of various perfluorocompounds on the stability of the fluoromeulsions. Note how FC-72 (a mixture of perfluorohexanes) is not able to stabilize the nanoemulsions. This is due to the higher water solubility of this compound compared to perfluorooctyl bromide: 300 nM vs. 5.1 nM. Perfluorodecalin is 5 times cheaper than perfluorooctyl bromide and represents a useful alternative to its use as a nanoemulsion stabilizer as shown in FIG. 6. In this plot PFOB refers to perfluorooctyl bromide, FC-72 refers to a mixture of perfluorohexanes and FDC refers to Perfluorodecalin.

1.d Semifluorinated Block Copolymer Surfactants Having a PEG Domain

The present example demonstrates the synthesis and the self-assembly properties of polymers responding to the molecular formulas $C_8F_{17}$—O—$(CH_2$—$CH_2$—$O)_n$—OH and $C_mF_{m+1}$—O—$(CH_2$—$CH_2$—$O)_n$—OMe The self-assembling and encapsulation abilities of polymers are particularly promising wherein the size of the fluorocarbon moiety is m=8, 10, 13, 15, 20 and the molecular weight of the PEG (methoxy terminal) is 5,000, 2,000, 1,000, and 500 g/mol for each of the fluorocarbon moieties. Increasing the number of fluorine atoms has several effects:

1. The polymer water solubility and its critical micelle concentration decrease.
2. The micelle aggregation number (number of polymer molecules in each enlarged micelle in the nano-emulsion) can change due to a variation in the size of the internal fluorophilic phase.

On the other hand, increasing the number of ethylene oxide units in the PEG increases the water solubility and the CMC of the micelles. Therefore, controlling the number of fluorine atoms and size of the PEG block may be useful in the present invention to selective control the pharmacokinetic properties (e.g, release properties etc.) of the encapsulated (fluorophilic) anesthetics.

1.d. Nano-Emulsions.

Nano-emulsification of sevoflurane and isoflurane was using the stabilizing additives and semifluorinated block copolymers of the present invention. The maximum amount of anesthetic that can be solubilized in a submicron emulsion starting from various concentrations of the fluoropolymers and of the additive (PFOB) was determined.

The following is the experimental protocol for generating a 20% V/V/10% V/V/25 mg/mL nanoemulsion between the anesthetic, the additive, and the fluoropolymer respectively. The same procedure can be adapted for any combination of the emulsions three components. Sevoflurane (3.4 mL, 20%) and perfluorooctyl bromide (1.7 mL, 10%) were added to an aqueous solution (11.9 mL) of F13M5 (298 mg, 25 mg/mL) and NaCl (107.1 mg, 0.9%) for a total volume of 17 mL. The two phase mixture was homogenized with a low energy mixer (Power Gen 500, Fisher Scientific) for 1 min at 21000 rpm at room temperature. The crude emulsion was further homogenized under high pressure (5000 psi, 1 min) using a Microfluidizer (model 110 S, Microfluidics Corp.) with the temperature maintained at 20.0° C. with a cooling bath. The product emulsions were stored in 15 mL sterile centrifuge tubes (Corning Inc.) at 4° C. until use.

Example 2

Toxicity Studies on the Anesthetic-Containing Nanoemulsions

In vitro toxicity studies. In vitro toxicity studies at this stage were carried out by determining the ability of solutions of $C_8F_{17}$—$CH_2$—O—$(CH_2$—$CH_2$—$O)_{136}$—OH at various concentrations to induce lysis in mice red blood cells. It was found that this semifluorinated block copolymer is completely inert and does not induce any appreciable cell lysis at concentrations ranging from 0.003 mM, below the critical micelle concentration, to 1.8 mM, fifteen times greater than the critical micelle concentration. Procedures were adapted from Lavasanifar, A.; Samuel, J.; Kwon, G. S. "Micelles Self-Assembled from poly(ethylene oxide)-block-poly(N-hexyl stearate L-aspartamide) by a Solvent Evaporation Method: Effect on the Solubilization and haemolytic Activity of Amphotericin B" J. Control. Rel. 2001, 77, 155-160.

In our studies, we show that our formulations safely and very quickly induce anesthesia in rats. The ability of dosing the amount of anesthetic given via intravenous delivery, compared to classical inhalation, allows us to provide the animal with only the anesthetic needed for a certain duration of anesthesia. In these conditions, recovery from general anesthesia is very rapid, eliminating problems due to the accumulation of unused anesthetic in various tissues. This is a problem that always accompanies general anesthesia by inhalation. Accumulation of unused anesthetic in various tissues is observed in some instances, however, upon infusion of the present therapeutic emulsions.

In Vitro Toxicity Studies.

Toxicity and design of the semifluorinated block copolymers. The main toxicity of perfluoro compounds is related to perfluoroacids. The present block copolymers are constructed in such a way that the metabolic formation of perfluoroacids is very difficult if not impossible. The perfluorocarbon segment of the polymer is linked to the PEG via an ether linkage (See, scheme 1 and 2,). This linkage is selected to provide beneficial properties, such as low toxicity. Easier synthetic procedures to prepare fluorinated surfactants call for ester formation and for other carboxylic acids derivatives. However, most acid derivatives are prone to be enzymatically cleaved to yield toxic perfluorocarboxylic acids. On the contrary, an ether linkage, such as the one used in the block copolymers of the present invention, is stable and unlikely to undergo enzymatic cleavage. In addition, one hydrogenated methylene group has been interposed between the ethereal oxygen and the fluorocarbon. This has been done to minimize activation of the ether linkage by the strongly electron-withdrawing fluorines.

Example 3

Fluoropolymer-Based Emulsions for the Intravenous Delivery of Sevoflurane

Abstract

The intravenous delivery of halogenated volatile anesthetics has been previously achieved using phospholipid-stabilized emulsions, especially with Intralipid. However, fluorinated volatile anesthetics, such as sevoflurane, are partially fluorophilic and do not mix well with classic non-fluorinated lipids. This effect limits the maximum amount of sevoflurane that can be stably emulsified in Intralipid to 3.5% v/v. This is a significant limitation to the potential clinical use of Intralipid-based emulsions.

The present Example demonstrates formulation of a 20% v/v sevoflurane emulsion using a novel fluorinated surfactant and stabilizing agent. The Example also shows the effectiveness and therapeutic index of the present emulsion-based formulations by administering it to male Sprague-Dawley rats via intravenous injection into the jugular vein. The median effective dose to induce anesthesia (ED50), median lethal dose (LD50), and therapeutic index (LD50/ED50) were determined. Anesthesia was measured by loss of the forepaw righting reflex. The ED50 and LD50 values were found to be 0.41 and 1.05 mL emulsion/kg body weight, respectively. These lead to a therapeutic index of 2.6, which compares favorably to previously determined values of emulsified isoflurane, as well as values for propofol and thiopental.

The present emulsion-based formulations increase the maximum amount of stably emulsified sevoflurane compared to Intralipid. These formulations can be used to rapidly induce anesthesia with bolus dosing from which recovery is smooth and rapid.

Introduction

The intravenous delivery of halogenated volatile anesthetics has been of interest for over 40 years, due to the possibility of improving upon traditional methods of delivery. Direct injection into the blood stream eliminates the time for the anesthetic to equilibrate with the lungs and leads to a more rapid onset of anesthesia. Initial instances of direct IV delivery of neat halothane, whether intentional or not, caused significant pulmonary damage and death in both animals and humans. Later efforts successfully utilized fat emulsions as a means of delivery for halothane and more recently isoflurane and sevoflurane. Studies on these emulsions also showed that intravenous delivery of fluorinated volatile anesthetics can be used to produce preconditioning and thereby reduce the extent of myocardial infarction. All of these examples have used either Intralipid (a phospholipid-stabilized soybean oil emulsion sold commercially) or directly used phospholipids as the emulsifier. However, fluorinated volatile anesthetics are partially fluorophilic and they do not mix well with classic non-fluorinated lipids. This property is evident in the limited concentrations of anesthetics that are soluble in Intralipid.

Perfluorocarbon emulsions have been widely studied for use as blood substitutes. The second generation emulsion Oxygent™ (Alliance Pharmaceutical Corp., San Diego, Calif.) incorporates 30% by volume of perfluorooctyl bromide (perflubron). In an in vitro analysis, Cuignet et al. have demonstrated that the presence of Oxygent greatly increases the blood:gas partition coefficient of isoflurane, sevoflurane and desflurane compared to Intralipid. Highly fluorinated compounds such as perfluorooctyl bromide are characterized by both lipophobicity and extreme hydrophobicity, the hallmark of fluorophilicity. The physical-chemical properties of organic molecules are deeply affected by the introduction of fluorine substituents to the point that highly fluorinated organic molecules can generate a new phase of liquid matter, usually referred to as a fluorous phase. This phase does not mix with both polar and non-polar hydrogenated phases. As an example, perfluorooctyl bromide presents only a limited solubility in either water or hydrocarbons, but it is completely miscible with perfluorosolvents. For the same reason, highly fluorinated anesthetics such as isoflurane, sevoflurane, and desflurane will prefer the environment provided by fluorophilic molecules such as perfluorooctyl bromide versus Intralipid. In addition, fluorinated surfactants have been shown to form highly stable o/w emulsions with fluorinated compounds by significantly reducing the interfacial tension between the perfluorocarbon and water.

In the present Example we demonstrate the successful induction of anesthesia in rats via intravenous delivery of sevoflurane, emulsified by the novel semi-fluorinated surfactant 3 (FIG. 7, F13M5) and stabilized by perfluorooctyl bromide. Furthermore, we have determined the median effective dose (ED50) and median lethal dose (LD50) of such emulsions. This study is the first example of emulsification of halogenated anesthetics using surfactants other than phospholipids.

Methods

All animal studies were conducted according to the guidelines laid out in the Guide for the Care and Use of Laboratory Animals and were approved by the University of Wisconsin Animal Care and Use Committee.

Polymer Synthesis

Figure 7:
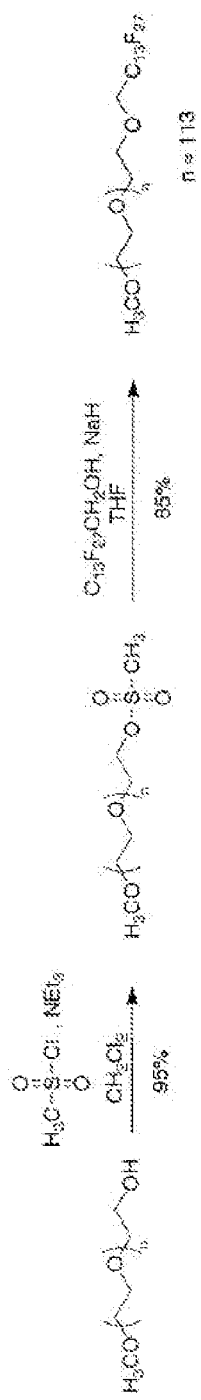
FIG. 7 provides a schematic showing the synthesis of the fluorosurfactant F13M5, used as an emulsifier.

A novel semifluorinated surfactant was synthesized for use as an emulsifier as indicated in FIG. 7. The synthesis starts with the activation of the hydroxyl functionality of polyethylene glycol monomethyl ether (mPEG, MW 5000) with methanesulfonyl chloride. The resulting polymeric methanesulfonate ester is then coupled to 1H,1H-perfluoro-1-tetradecanol (SynQuest Laboratories, Inc., Alachua, Fla.) to afford the final product, F13M5, in high overall yield. The polymer nomenclature FXMY indicates that a certain polymer contains X number of perfluorocarbons and a monomethyl-poly (ethylene glycol) block of averaged molecular weight Y (in thousands g/mol).

Experimental

Polyethylene glycol monomethyl ether 1 (average MW=5000 g/mol), was purchased from Fluka and lyophilized before use. Methanesulfonyl chloride (99.5%) and triethylamine (99.5%) were purchased from Aldrich and used as provided. Methylene chloride (GC Resolv) and THF (Optima) were purchased from Fisher Scientific and dried by flowing through alumina-containing columns. Anhydrous diethyl ether was purchased from EMD. 1H, 1H-perfluoro-1-tetradecanol was purchased from SynQuest Labs. Dry NaH (95%) was purchased from Aldrich. $^{19}$F-NMR and $^{1}$H-NMR spectra were obtained on a Varian Inova spectrometer operating at 400 MHz. HPLC chromatograms for product purity determination were obtained on a Gilson HPLC system, with a Jordi RP-DVB column with particle size of 5 µm and pore size of 1000 Å, and detected with a prepELS detector from Gilson. The solvent gradient started at 10% MeCN/90% $H_2O$ and increased to 100% MeCN over 20 min. The flow rate was 1 mL/min.

Polyethylene glycol monomethyl ether mesylate 2. Lyophilized polyethylene glycol monomethyl ether 1 (30.67 g, 6.1 mmol) was dissolved in anhydrous $CH_2Cl_2$ (200 ml) with mild heating. After cooling to room temperature, triethylamine (1.7 ml, 12 mmol) and mesyl chloride (0.7 ml, 9 mmol) were added and the reaction mixture was stirred overnight under argon at room temperature. The precipitated salts were removed by vacuum filtration, and the filtrate was rotary evaporated to dryness. The remaining solid was taken up in $CHCl_3$ and purified through silica gel with $CHCl_3$, followed by 10:1 $CHCl_3$:methanol to remove any residual salts. The filtrate was evaporated to dryness and taken up in THF (200 ml). Diethyl ether (250 ml) was added and the solution was cooled in a refrigerator at 4° C. for 30 minutes until precipitation was complete. The solid product was collected by vacuum filtration, dissolved in water and lyophilized to yield polyethylene glycol monomethyl ether mesylate, 2, as a white powder (27.4 g, 88%).

$^{1}$H NMR $CDCl_3$ δ3.09 (s, 3H), 3.38 (s, 3H), 3.46-3.83 (m, 450H), 4.38 (m, 2H)

Polyethylene glycol monomethyl ether-perfluorocarbon conjugate 3 (F13M5). Mesylate 2 (8.14 g, 1.6 mmol) and 1H, 1H-perfluoro-1-tetradecanol (2.789 g, 3.98 mmol) were dissolved in anhydrous THF (500 ml) with mild heating. After cooling to room temperature NaH (0.356 g, 14.8 mmol) was added. After reflux for 48 hrs the reaction was quenched with dropwise addition of $H_2O$. The precipitated salts were removed by vacuum filtration. The filtrate volume was reduced by half by rotary evaporation, diethyl ether was added (250 mL) and the solution was cooled until precipitation was complete. The solid was collected by vacuum filtration, taken up in $CHCl_3$ and flowed through silica gel with 10:1 $CHCl_3$:methanol to remove any residual salts. The filtrate was evaporated to dryness and taken up in THF (200 mL). Diethyl ether (250 ml) was added and the solution was cooled in a refrigerator at 4° C. for 30 minutes until precipitation was complete. The solid product was collected by vacuum filtration, dissolved in water and lyophilized to yield 14H, 14H-perfluorotetradecane polyethylene glycol monomethyl ether, 3, (F13M5) as a white powder (7.8 g, 85%).

$^{1}$H NMR CDCl$_3$ δ3.38 (s, 3H), 3.46-3.83 (m, 450H), 4.04 (t, J=13.6 Hz, 2H)

$^{19}$F NMR (CDCl$_3$) δ −81.103 (t, J=10.5, 3F), 120.131 (m, 2F), 122.014 (m, 16F), −123.014 (m, 2F), −123.785 (m, 2F), −126.451 (m, 2F). Polymer purity was confirmed by HPLC. Chromatogram is provided as supporting information.

Emulsion Preparation

Sevoflurane (Abbott Labs, N. Chicago, Ill., 3.4 mL) and perfluorooctyl bromide (SynQuest Laboratories, Inc., Alachua, Fla., 1.7 mL) were added to an aqueous 0.9% NaCl solution (11.9 mL) of F13M5 (298 mg, 25 mg/mL), for a total volume of 17 mL. The two-phase mixture was homogenized with a low energy mixer (Power Gen 500, Fisher Scientific, Hampton, N.H.) for 1 min at 21000 rpm at room temperature. In an embodiment, a formulation of 20% v/v sevoflurane, 10% v/v perfluorooctyl bromide and 25 mg/mL F13M5 in 0.9% NaCl, was used. The crude emulsion was further homogenized under high pressure (5000 psi, 1 min) using a Microfluidizer (model 110 S, Microfluidics Corp., Newton, Mass.) with the temperature maintained at 20.0° C. with a cooling bath. The product emulsions of 20% (v/v) sevoflurane were stored in 15 mL sterile centrifuge tubes (Corning Inc., Corning, N.Y.) at 4° C. until use. Similar emulsions but containing isoflurane were also prepared. Initial studies employing tail vein injection utilized the isoflurane emulsions, and full dose-response studies employing implanted catheters utilized the sevoflurane emulsions.

The emulsions were sized by dynamic light scattering prior to use. For these measurements, the emulsions were mixed by inversion of the centrifuge tube to eliminate inhomogeneity due to either flocculation or sedimentation. The emulsions were then diluted by a factor of 300 by adding 10 μL of the emulsion to 2.990 mL of 0.9% NaCl. Sizing was done by dynamic light scattering (NICOMP 380 ZLS, Particle Sizing Systems, Santa Barbara, Calif.) with a 639 nm laser at a scattering angle of 90°. Each sample was run for 15 min and all numbers are reported as Gaussian volume weighted. The emulsions were only used if the average diameter was less than 350 nm. This cutoff was established to ensure consistent physical characteristics of the emulsion and to prevent acute toxicity that can develop with increased particle size.[15] Additionally, the emulsion was filtered through a 0.45 μm nylon syringe filter. The final nano-emulsions are milky-white.

Intralipid emulsions were prepared by emulsifying the corresponding amount of sevoflurane with commercially available Intralipid using the same methods and equipment described for the nanoemulsions. Intralipid emulsions were not tested in animals due to the small amount of anesthetic that could be stably emulsified.

Animal Studies

Preliminary experiments performed to test for the efficacy of the anesthetic emulsions were performed using tail vein injections in adult male Sprague-Dawley rats (Harlan Sprague Dawley, Inc., Indianapolis, Ind.) weighing approximately 300 g. For these studies rats were restrained using a commercially available rodent restraint tube (manufacturer) during the injection. For complete dose-response measurements, adult male Sprague-Dawley rats (Harlan Sprague Dawley, Inc., Indianapolis, Ind.) weighing approximately 300 g with a jugular catheter surgically implanted prior to purchase were used. Each dose was tested on five rats. The same rats used on multiple days, but rats were only injected once a day to prevent any cumulative effects. Each rat was weighed, so that the dose could be adjusted to be consistent with varying body weights. To determine the dose which was effective for anesthetizing fifty percent of the population (ED$_{50}$), groups composed of five rats each were injected with doses of emulsified anesthetic of 0.33, 0.36, 0.39, 0.43, 0.47, 0.55 and 0.62 mL/kg, respectively. Using a syringe pump (11 plus, Harvard Apparatus, Holliston, Mass.) the rate was adjusted so that the bolus dose was always administered over 20 s regardless of volume. Table 3.1 provides a summary of the doses of emulsified anesthetic utilized and the number of rats anesthetized (out of 5) upon administration.

TABLE 3.1

Summary of dose administered for determination of ED$_{50}$

| Dose (mL/kg) | # Rats Anesthesized (out of 5) |
|---|---|
| 0.33 | 0 |
| 0.36 | 0 |
| 0.39 | 2 |
| 0.43 | 3 |
| 0.47 | 5 |
| 0.55 | 5 |
| 0.62 | 5 |

To determine the dose which was lethal for fifty percent of the population (LD50), groups composed of five rats each were injected with doses of emulsified anesthetic of 0.945, 0.982, 1.018, 1.055, 1.091, and 1.127 mL/kg, respectively. Directly prior to the injections for the LD$_{50}$ measurements the rats were allowed to spontaneously breathe pure oxygen by placing them for 3 minutes in an induction chamber, to simulate the "preoxygenation" that is commonly used prior to induction in human patients. As a control experiment, emulsions containing only 10% perfluorooctyl bromide and no sevoflurane were prepared in the same manner as described above. Five rats were injected with a volume of 1.091 mL/kg, equal to the sevoflurane emulsion volume at which 100% of the rats died.

For the actual injection, animals were restrained and the catheter wire port plug was removed and replaced with a flushing assembly (23 g hypodermic needle connected to a 1 cc syringe). The syringe plunger was gently drawn back until blood was seen in the tubing to ensure that there was no blockage of the catheter. If resistance was encountered, gentle pressure was applied to the plunger in an attempt to dislodge the obstruction. Once the catheter was completely filled with blood it was connected to a syringe containing the experimental solution that was controlled by the syringe pump. The catheter was primed with 40 μL of solution (the volume of the catheter) so that flow into the body was immediate upon the start of the injection, and then the full injection was given. After the injection was complete the rat was rolled onto its back, with a loss of forepaw righting reflex considered inducement of anesthesia. If the righting reflex was lost, the right hind foot was pinched with a steel forceps to determine if there was response to a painful stimulus. If the foot was not withdrawn the pinch was applied every five seconds until there was a response. After injection the rat was observed for three minutes, to measure the time required to regain the righting reflex, and to observe for the presence of uncoordination (unsteady gait) or disorientation (repeated episodes of rearing and falling) during recovery. A "smooth recovery" was defined as resumption of grooming or purposeful exploration without evidence of uncoordination or disorientation during the recovery period. When recovery was complete (within three minutes in all cases), the catheter was flushed with 0.08 mL of a saline solution to remove the residual anesthetic emulsion and then refilled with 0.08 mL of a heparin based fill solution. The sterile wire port plug was restored to seal the catheter.

Estimates for $ED_{50}$ and $LD_{50}$ were calculated through non-linear regression, fitting data to a sigmoidal dose-response relationship using the program Prism (version 4.0a, GraphPad Software, Inc., San Diego, Calif.). The data were fit to the equation:

$$Y = Y_{min} + \frac{Y_{max} - Y_{min}}{1 + 10^{(LogED_{50} - X)*HillSlope}}$$

where X is the logarithm of concentration and Y is the response.

The duration of anesthesia vs. dose graph (FIG. 9) was made using DeltaGraph (version 5.6.1, SPSS Inc. and Red Rock Software, Inc.)

Results

In a set of preliminary experiments conducted using tail vein injections, anesthetic emulsions were found to induce anesthesia rapidly (within approximately 15 seconds, during the course of the injection) and for very brief durations (approximately 30 seconds). On recovery, animals showed no evidence of irritation, such as grooming or biting of their legs or tail, nor was there any obvious visual evidence of irritation at the injection site. Within approximately one minute of the termination of injection, animals had returned to exploring their environment or grooming, with no evidence of uncoordination, disorientation, or residual sedation.

Figure 8:
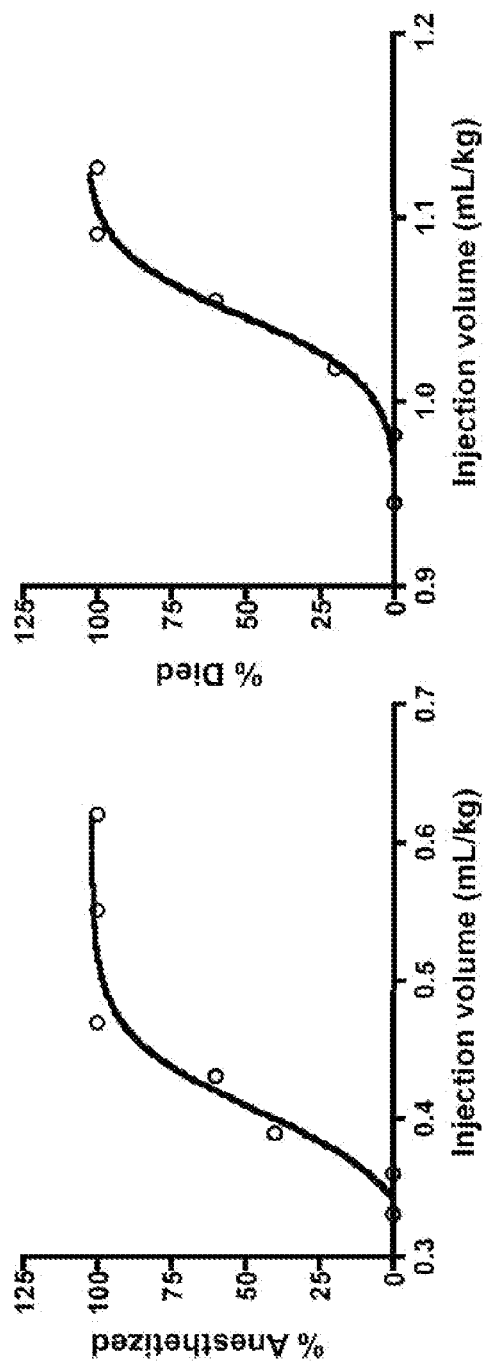
FIG. 8 provides dose-response curves for the determination of the ED50 value (left) and the LD50 value (right).

Because of the rapid onset, the ultrashort duration of action, and the need to repeatedly inject animals to establish $ED_{50}$ and $LD_{50}$ values, we used rats with catheters surgically implanted into the jugular vein and a syringe pump to deliver anesthetic emulsion for further studies. The dose-response curves for the $ED_{50}$ and $LD_{50}$ are presented in FIG. 8. The calculated $ED_{50}$ value was 0.41 mL emulsion/kg body weight, with a 95% confidence interval from 0.37 to 0.45. This $ED_{50}$ value corresponds to 0.081 mL pure sevoflurane/kg body weight based on an emulsion containing 20% v/v of sevoflurane. The calculated $LD_{50}$ value was 1.05 mL/kg body weight, with a 95% confidence interval from 1.03 to 1.07. This $LD_{50}$ value corresponds to 0.21 mL pure sevoflurane/kg body weight based on 20% v/v sevoflurane emulsion. The therapeutic index ($LD_{50}/ED_{50}$) was calculated to be 2.6.

In the rats in which the righting reflex was lost, there was a response to the initial foot pinch (as indicated by a slight withdrawal of the foot) in all rats but one. One rat that was injected with the highest dose of 0.62 mL/kg did not respond to three foot pinches given at five second intervals, but did respond to the fourth pinch.

Control experiments were performed by using anesthetic-free emulsions to test for effects of the fluoropolymer/perfluorocarbon emulsion. In these studies, there was no evidence of any anesthetic effects, gross neurological deficit, or mortality. All rats were living five days later, giving no evidence of acute toxicity from circulating emulsions that had released the sevoflurane content.

Figure 9:
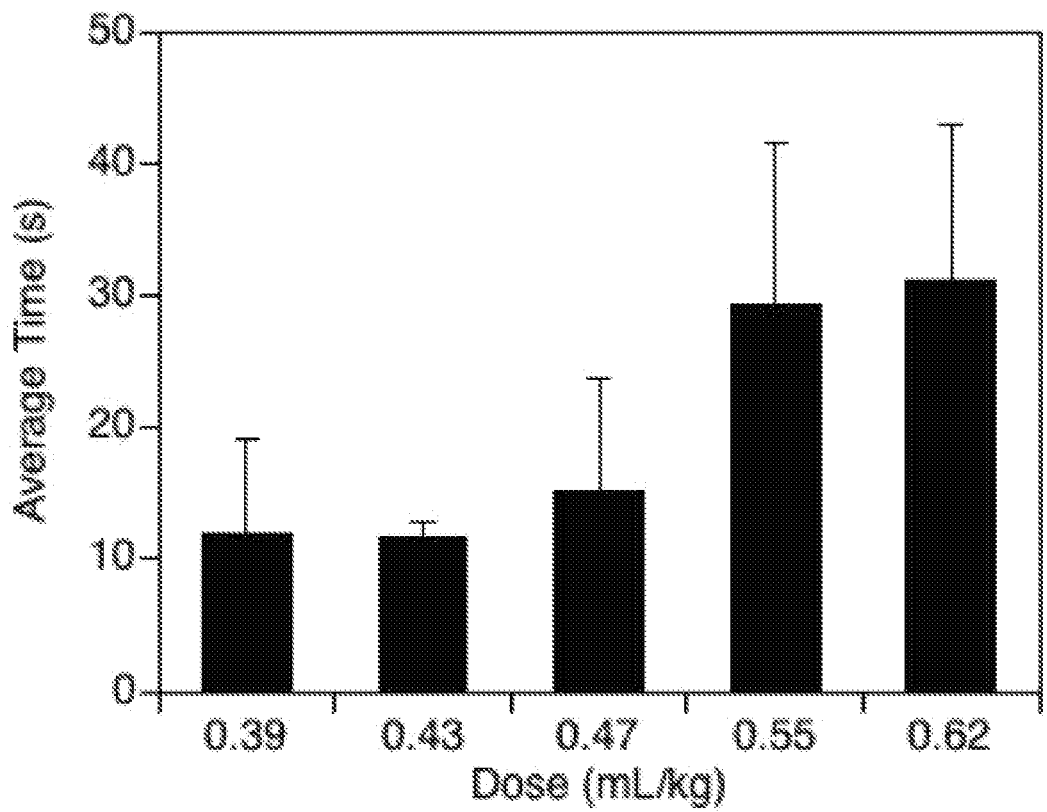
FIG. 9 provides a summary of average duration of anesthesia for rats that were anesthetized during the ED50 determination.

When anesthesia was induced, it happened before the completion of the bolus dose, typically 17-20 s from the start. The average duration of anesthesia before recovery of the righting reflex is shown in FIG. 9. The duration was recorded at every concentration where anesthesia was induced, though by the nature of the ED50 experiments some points had more rats anesthetized than others. The error bars indicate standard deviations, but the number of included points varies from 2-5 based on the number of rats in which anesthesia was induced.

The stability of the nanoemulsions was checked with dynamic light scattering. Over a period of two months, emulsions containing 20% v/v of sevoflurane, 10% v/v of perfluorooctyl bromide and 25 mg/mL of fluoropolymer did not show phase separation and the particle size was always in the submicron range. On the contrary, we found that Intralipid emulsions prepared under the same conditions used for the fluorous formulations and containing just 10% v/v of sevoflurane were extremely unstable and complete phase separation was easily detected within one day.

Discussion

This Example demonstrates that a novel intravenous formulation of sevoflurane prepared using a fluoropolymer surfactant and perfluorocarbon is stable as an emulsion yet releases sevoflurane rapidly enough following intravenous injection that it can be used to induce anesthesia in vivo. The emulsification of volatile anesthetics in lipid formulations has previously been shown. However, for any emulsion formulation to become clinically useful, the volume that can be stably emulsified must be significantly increased from current lipid formulations. The present study is the first use of an emulsifier other than phospholipids for a volatile anesthetic. The fluoropolymer-based emulsion that we tested here can stably emulsify 20% v/v sevoflurane, which is almost a six-fold increase over the recently reported value of 3.46% v/v as the maximum solubility of sevoflurane in 30% Intralipid. Furthermore, the instability of concentrated emulsions of sevoflurane in Intralipid presents a significant limitation to the clinical utility of intravenous delivery using Intralipid in human patients. On the contrary, the use of fluorosurfactants allows a considerably more convenient use of stable and concentrated emulsions of the volatile anesthetic.

While the use of sevoflurane emulsions has been demonstrated before, this work also presents the first measurement of a therapeutic index for emulsified sevoflurane. Our calculated value of 2.6 compares reasonably well to previously published values for emulsified isoflurane of 3.2 and 3.1 as well as 3.1 for propofol and 2.2 for thiopental. This finding suggests that a sevoflurane emulsion may provide an effective and convenient means of inducing anesthesia in human patients.

Doses that were near the $ED_{50}$ for LORR were effective for shorter periods of time than higher amounts. In all instances, both the time to onset of anesthesia and the recovery of the righting reflex was very rapid in comparison to other commonly used intravenous induction agents such as thiopental and propofol.[10] The ability to rapidly induce or to deepen existing anesthesia by intravenous injection, combined with its rapid recovery profile, may prove beneficial under some circumstances. For example, it may be possible to achieve more stable hemodynamics by matching the depth of anesthesia with the intensity of stimulus during intubation, incision, or other brief but intense stimuli such as insertion of cranial pins for neurosurgical procedures.

In conclusion, this Example shows that a mixture of fluoropolymers and a fluorous additive such as perfluorooctyl bromide can stably emulsify 20% by volume of sevoflurane, a highly fluorinated volatile anesthetic. This is at least in part due to the increased affinity of the anesthetic for a fluorophilic surfactant. These formulations can be used to induce anesthesia with bolus dosing, from which recovery is smooth and rapid. The observed difference between the measured $ED_{50}$ and $LD_{50}$ of our formulations supports that these emulsions may be suitable for clinical use.

EXAMPLE 4

Ostwald Ripening in Sevoflurane Emulsions Stabilized by Fluorinated Surfactants This Example provides experimental results characterizing the physical properties and stability of an emulsion of sevoflurane, a moderately water-soluble highly fluorinated ether used clinically as a volatile anesthetic, stabilized with a non-ionic fluorinated surfactant and stabilizing agent. The affinity of sevoflurane for the fluorinated surfactant allowed a significant increase in the amount of sevoflurane that could be stably emulsified compared to a hydrogenated emulsion. Though stable to coalescence, the emulsions were susceptible to Ostwald ripening, which was limited by the presence of a secondary, less soluble additive, perfluorooctyl bromide. An even less water-soluble additive, perfluorotridecane, completely stopped ripening, but also allowed coalescence through its preferential adsorption at the interfacial polymeric layer. Excess surfactant, present as micelles, had no effect on the ripening rate. It is found that a reduction in the size of the polar head group of the surfactant, without modifying the fluorocarbon block, led to a reduction in the rate of Ostwald ripening.

Introduction

The physical-chemical properties of organic molecules are deeply affected by the introduction of fluorine substituents to the point that highly fluorinated organic molecules can generate a new phase of liquid matter, usually referred to as a fluorous phase. Highly fluorinated compounds are characterized by both lipophobicity and extreme hydrophobicity and do not mix with both polar and non-polar hydrogenated phases. As an example, perfluorooctane presents only a limited solubility in either water or hydrocarbons, but it is completely miscible with perfluorosolvents. The modern volatile anesthetics isoflurane, desflurane and sevoflurane are all highly fluorinated, and should thus prefer a fluorous environment over any other phase. FIG. 1 provides the structures of several fluorinated volatile anesthetics.

The intravenous delivery of halogenated volatile anesthetics has been of interest for over 40 years, due to the possibility of improving upon traditional methods of delivery. Direct injection into the blood stream eliminates the time for the anesthetic to equilibrate with the lungs and leads to a more rapid onset of anesthesia. Initial instances of direct IV delivery of neat halothane, whether intentional or not, caused significant pulmonary damage and death in both animals and humans. Later efforts have successfully utilized fat emulsions as a means of delivery for halothane and, more recently, isoflurane and sevoflurane. All of these examples have used either Intralipid (a commercially available phospholipid-stabilized soybean oil emulsion) or directly used phospholipids as the emulsifier.

However, fluorinated volatile anesthetics are partially fluorophilic and do not mix well with classic non-fluorinated lipids. This property is evident in the limited concentrations of anesthetics that are soluble in Intralipid. It has also been shown that an emulsion containing 30% v/v perfluorooctyl bromide increased the blood:gas partition coefficient of isoflurane, sevoflurane and desflurane compared to Intralipid, further supporting the hypothesis that the anesthetics would prefer a fluorous environment.

Emulsions are heterogeneous systems composed of one immiscible liquid dispersed as droplets within another liquid. They are not thermodynamically stable, but the stability can be improved by additives such as surfactants, finely divided solids etc. Perfluorocarbon-in-water emulsions have been widely studied for use as blood substitutes. Though hydrogenated surfactants have generally been used, fluorinated surfactants have been shown to form highly stable oil-in-water (o/w) emulsions with fluorinated compounds by significantly reducing the interfacial tension between the perfluorocarbon and water.

The two primary mechanisms for emulsion destabilization through droplet size growth are coalescence and Ostwald ripening (molecular diffusion). Coalescence is the irreversible collision and subsequent fusion of droplets. If unchecked, the ultimate result is phase separation. With Ostwald ripening the contents of the disperse phase diffuse into the continuous phase causing large droplets to grow continuously larger at the expense of smaller ones due to differences in chemical potential. Ostwald ripening has been shown to be the dominant method of particle size growth in fluorocarbon-in-water emulsions. According to Lifshitz-Slyozov-Wagner (LSW) theory, the rate of Ostwald ripening, $\omega$, can be expressed by the following equation:

$$\omega = \frac{dr^3}{dt} = \frac{8DC_\infty \gamma M}{9\rho^2 RT} \quad (1)$$

where r is the radius of the droplets, t is the time of storage, D is the diffusion coefficient of the molecules of the disperse phase in the continuous phase, $C_\infty$ is the bulk solubility of the disperse phase in the continuous phase, $\gamma$ is the interfacial tension between phases, M is the molar mass of the disperse phase, $\rho$ is the density of the disperse phase, R is the gas constant and T is the absolute temperature. As can be seen in Eq. 1, for an o/w emulsion the rate of ripening is directly related to the water solubility of the oil. With a water solubility of 6 mM, emulsified sevoflurane will likely be susceptible to Ostwald ripening.

Higuchi and Misra suggested that the addition of a secondary, less water soluble, component, could slow ripening. The slower diffusion of the secondary component will lead to a heterogeneous distribution with smaller droplets enriched in the less soluble component and larger droplets enriched in the more soluble component. However, this internal segregation will be thermodynamically opposed as osmotic pressure will act to limit differences between droplets and equilibrium will eventually be reached. This principle has been successfully applied with previous fluorocarbon emulsions.

Examples 2 and 3 demonstrate the in vivo effectiveness of these emulsions for inducing anesthesia in rats and would like to report the complete physical characterization of the emulsion droplets. In addition to describing the first example of emulsification of a volatile anesthetic using surfactants other than phospholipids, the present Example also presents the first comprehensive physical characterization of emulsion stability for an emulsified volatile anesthetic.

Experimental Section

Polymer Synthesis

Figure 10:
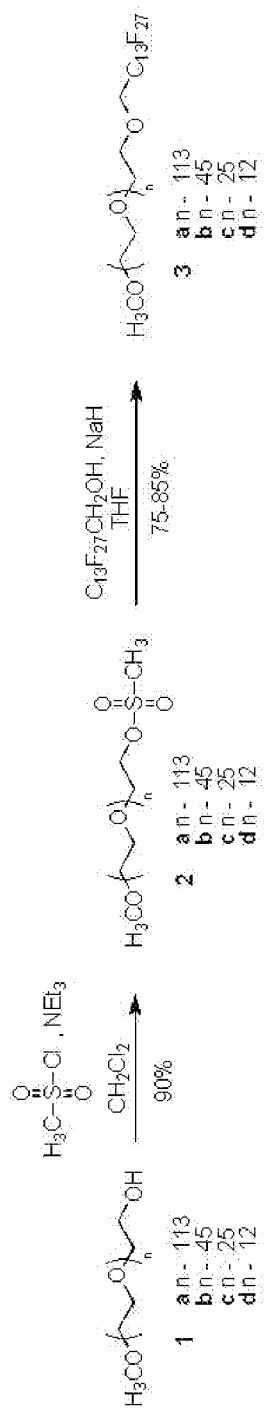
FIG. 10 provides a general synthetic scheme for the reaction of the fluorinated surfactants.

A series of novel semifluorinated surfactants were synthesized for use as emulsifiers as indicated in FIG. 10. The synthesis starts with the activation of the hydroxyl functionality of the corresponding polyethylene glycol monomethyl ether (mPEG, MW 5000, 2000, 1100, 550) with methanesulfonyl chloride. The resulting polymeric methanesulfonate ester is then coupled to 1H,1H-perfluoro-1-tetradecanol to afford the final product in overall yields ranging from 68-78%. Conversion at each step was quantitative, but some mass was lost during purification. The polymer nomenclature FXMY indicates that a certain polymer contains X number of perfluorinated carbon atoms and a monomethyl-poly(ethylene glycol) block of averaged molecular weight Y (in thousands g/mol).

Materials

Polyethylene glycol monomethyl ether of all molecular weights (average MW=5000, 2000, 1100 and 550 g/mol), methanesulfonyl chloride (99.5%), triethylamine (99.5%) and dry NaH (95%) were purchased from Aldrich and used as provided. Methylene chloride (GC Resolv) and THF (Optima) were purchased from Fisher Scientific and dried by flowing through alumina-containing columns. Chloroform and methanol were purchased from Fisher and used as provided. Anhydrous diethyl ether was purchased from EMD. 1H, 1H-perfluoro-1-tetradecanol was purchased from SynQuest Laboratories.

Compound Characterization $^{19}$F-NMR and $^1$H-NMR spectra were obtained on a Varian Inova spectrometer operating at 400 MHz. HPLC chromatograms for product purity determination were obtained on a Gilson HPLC system, with a Jordi RP-DVB column with particle size of 5 μm and pore size of 1000 Å, and detected with a prepELS detector from Gilson. The solvent gradient started at 10% MeCN/90% H$_2$O and increased to 100% MeCN over 20 min. The flow rate was 1 mL/min.

Polyethylene glycol monomethyl ether mesylate 2a. Polyethylene glycol monomethyl ether 1a (30.67 g, 6.1 mmol) was dissolved in anhydrous CH$_2$Cl$_2$ (200 ml) with mild heating. After cooling to room temperature, triethylamine (1.7 ml, 12 mmol) and mesyl chloride (0.7 ml, 9 mmol) were added and the reaction mixture was stirred overnight under argon at room temperature. The precipitated salts were removed by vacuum filtration, and the filtrate was rotary evaporated to dryness. The remaining solid was taken up in CHCl$_3$ and purified through silica gel with CHCl3, followed by 10:1 CHCl$_3$:methanol, to remove any residual salts. The filtrate was evaporated to dryness, taken up in water and lyophilized to yield polyethylene glycol monomethyl ether mesylate, 2a, as a white powder (27.4 g, 90%). The same procedure was followed for the mesylation of mPEG 550, 1100 and 2000, with the exception that those reaction mixtures were cooled to −78°, −78° and 0° C., respectively, before the addition of the mesyl chloride. $^1$H NMR CDCl3 δ3.09 (s, 3H), 3.38 (s, 3H), 3.46-3.83 (m, approximately 450H), 4.38 (m, 2H)

Polyethylene glycol monomethyl ether-perfluorocarbon conjugate 3a (F13M5). Mesylate 2a (8.14 g, 1.6 mmol) and 1H, 1H-perfluoro-1-tetradecanol (2.789 g, 3.98 mmol) were dissolved in anhydrous THF (500 ml) with mild heating. After cooling to room temperature NaH (0.356 g, 14.8 mmol) was added. After reflux for 48 hrs the reaction was quenched with dropwise addition of H$_2$O. The precipitated salts were removed by vacuum filtration, and the filtrate was evaporated to dryness. The remaining solid was taken up in CHCl$_3$ and purified through silica gel with 10:1 CHCl$_3$:methanol to remove any residual salts. The filtrate was evaporated to dryness and taken up in THF (200 mL). Diethyl ether (250 ml) was added and the solution was cooled in a refrigerator at 4° C. for 30 minutes until precipitation was complete. The solid product was collected by vacuum filtration, dissolved in water and lyophilized to yield 14H, 14H-perfluorotetradecane polyethylene glycol monomethyl ether, 3a, (F13M5) as a white powder (7.8 g, 85%). The same procedure was followed for the alkylation of mPEG-Ms 550, 1100 and 2000. $^1$H NMR CDCl$_3$ δ3.38 (s, 3H), 3.46-3.83 (m, approximately 450H), 4.04 (t, J=13.6 Hz, 2H) $^{19}$F NMR (CDCl$_3$) δ −81.10 (t, J=10.5, 3F), −120.13 (m, 2F), −122.01 (m, 16F), −123.01 (m, 2F), −123.79 (m, 2F), −126.45 (m, 2F). Polymer purity was confirmed by HPLC and the chromatograms are provided in the supporting information.

Emulsion Preparation

As a typical example, sevoflurane (Abbott Labs, N. Chicago, Ill., 3.4 mL) and perfluorooctyl bromide (SynQuest Laboratories, Inc., Alachua, Fla., 1.7 mL) were added to an aqueous 0.9% NaCl solution (11.9 mL) of F13M5 (298 mg, 25 mg/mL), for a total volume of 17 mL. The two-phase mixture was homogenized with a low energy mixer (Power Gen 500, Fisher Scientific, Hampton, N.H.) for 1 min at 21000 rpm at room temperature. The crude emulsion was further homogenized under high pressure (5000 psi, 1 min) using a Microfluidizer (model 110 S, Microfluidics Corp., Newton, Mass.) with the temperature maintained at 20.0° C. with a cooling bath. The product emulsions were stored in 15 mL sterile centrifuge tubes (Corning Inc., Corning, N.Y.) at 4° C. until use. All emulsions were prepared in this same manner with the requisite percentages of each component as necessary. Intralipid emulsions were prepared by adding sevoflurane to Intralipid (20%, Fresenius Kabi, Uppsala, Sweden) and then homogenizing and microfluidizing as above.

Particle Sizing

Prior to sizing the emulsions were mixed by inversion of the centrifuge tube to eliminate inhomogeneity due to either flocculation or sedimentation. The emulsions were diluted by a factor of 300 by adding 10 μL of the emulsion to 2.990 mL of 0.9% NaCl. Sizing was done by dynamic light scattering (NICOMP 380 ZLS, Particle Sizing Systems, Santa Barbara, Calif.) with a 639 nm laser at a scattering angle of 90°. Each sample was run for 15 min and all numbers are reported as Gaussian volume weighted.

Results and Discussion

Figure 11:
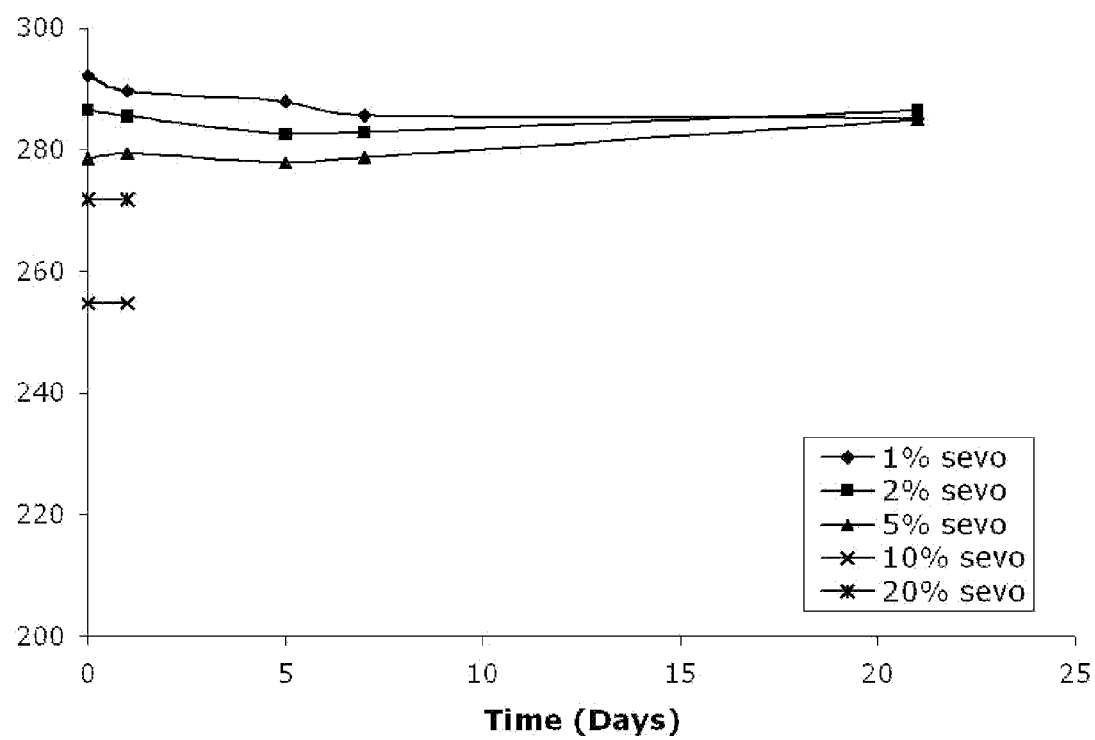
FIG. 11 provides a plot showing the stability of sevoflurane (percent v/v) emulsified in 20% Intralipid. The 10% and 20% lines do not continue because there was phase separation after only one day. Droplet diameter in nanometers is plotted (y-axis) versus time (days).
Figure 12A:
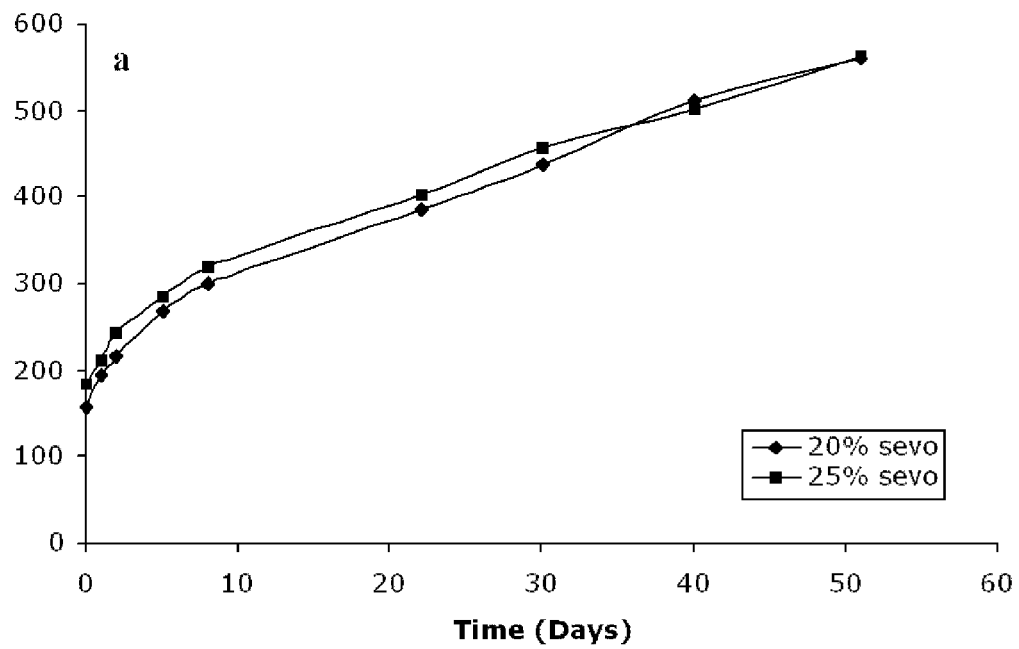
FIG. 12a shows a plot of the changes in particles diameter (nanometers) with time (days).

It has previously been determined that the maximum amount of sevoflurane that can be stably emulsified in 30% Intralipid is 3.46% v/v. The experimental methodology used for that determination allowed a gas containing 2.2% sevoflurane to diffuse into the Intralipid emulsion until equilibrium was reached. Because emulsions are thermodynamically unstable they generally require the input of energy for their formation. It is possible that an emulsification procedure, such as homogenization, that provides an energy input could enable more sevoflurane to be stably emulsified. Sevoflurane in concentrations of 1, 2 and 5% v/v formed stable emulsions with Intralipid when prepared with homogenization and microfluidization (See, FIG. 11). However, concentrations of 10 and 20% showed almost complete phase separation after only one day. These results confirm that the maximum amount of sevoflurane that can be emulsified in Intralipid is limited, regardless of the method of emulsification. By contrast, there was no evidence of phase separation in any system that only used the semi-fluorinated surfactant F13M5, even up to volumes of 25% sevoflurane (See, FIG. 12a).

Figure 12B:
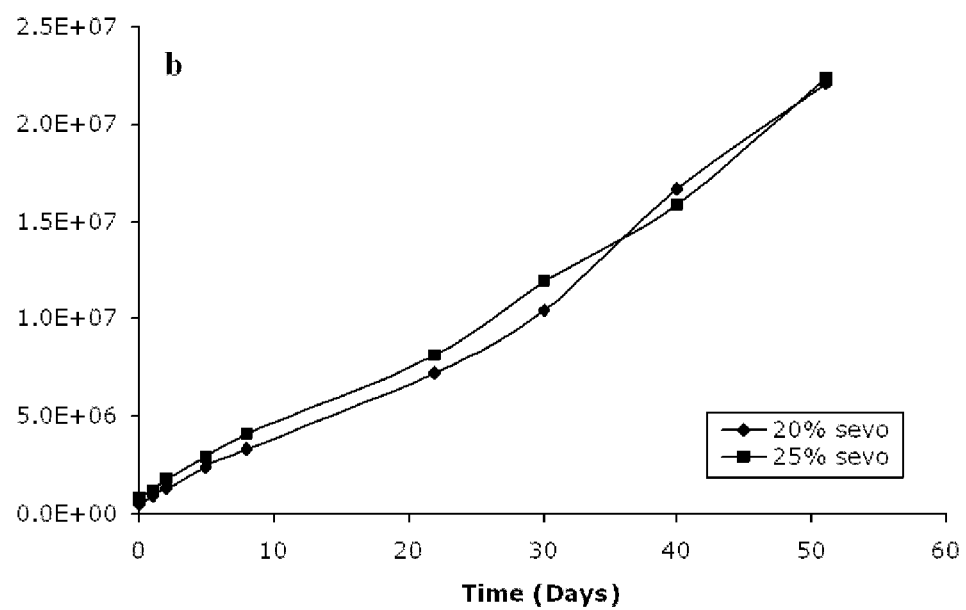
FIG. 12b shows changes in the cube of particle radius with time.

As shown by LSW theory, emulsions that undergo Ostwald ripening will exhibit linear growth with the cube of the radius over time. If coalescence is the dominant mechanism, the change of the cube of the radius should be exponential with time. Furthermore, of the two mechanisms for emulsion destabilization, coalescence is the only one that directly leads to phase separation. In addition to not visually observing any signs of gross phase separation, the linear growth rate (See, FIG. 12b) gives no indication that coalescence is happening. This is unsurprising as it has previously been demonstrated that the steric layer provided by a polymer such as PEG can be effective as a barrier against coalescence. If coalescence is prevented and Ostwald ripening is the primary destabilization mechanism, then particle growth will be linear with the cube of the radius in all cases. While this is the case in FIG. 12b and for graphs throughout the paper, for the sake of clarity subsequent graphs will show the change in diameter over time (which is not linear) because from those graphs the actual size is more readily understood.

Figure 13:
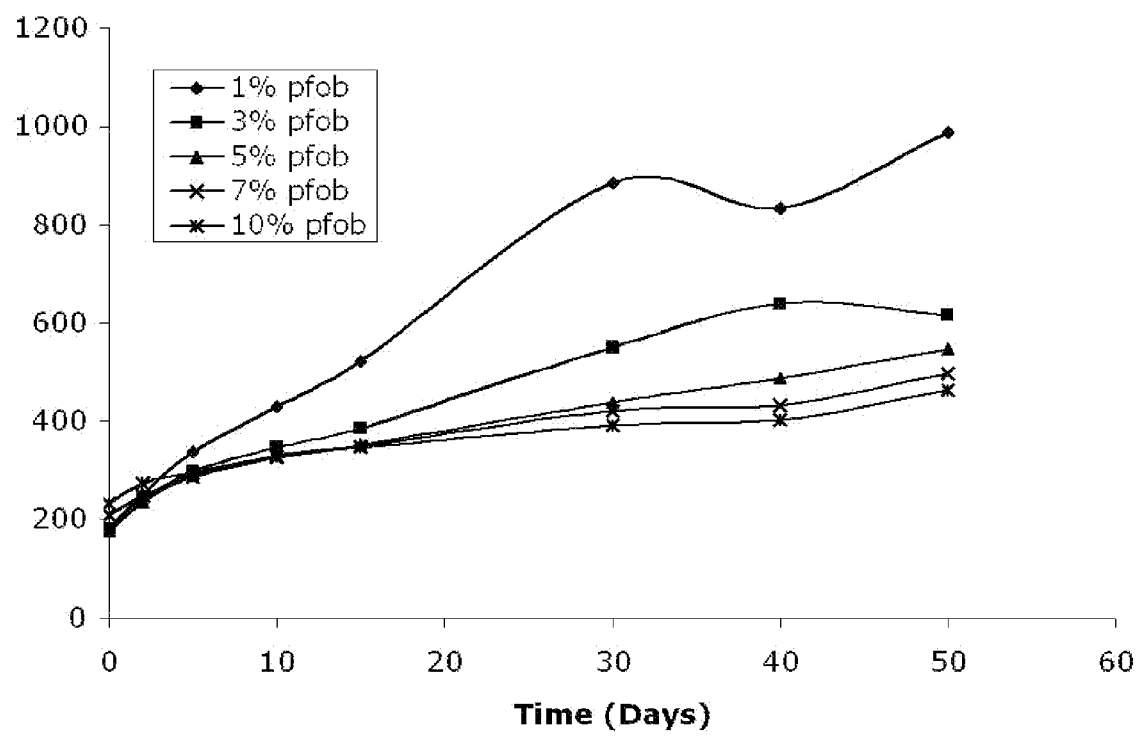
FIG. 13 provides a plot showing the effect of perfluorooctyl bromide (pfob) amount (% v/v) of emulsion stability. All emulsions contain 20% v/v sevoflurane and 1.5% w/v F13M5. Droplet diameter in nanometers is plotted (y-axis) versus time (days).

An emulsion of 20% v/v sevoflurane, without additive and stabilized by F13M5, showed no visual phase separation, indicating that coalescence was prevented. However, ripening was rapid enough that the DLS was unable to converge upon a value for the size within the 15 min period of measurement, which prevented the acquisition of statistically meaningful data. The addition of perfluorooctyl bromide slowed ripening enough to allow measurement. This additive was chosen because it is fluorophilic, non-toxic, has a limited retention time in the body and is commercially available. As might be expected, increasing amounts of additive slows the ripening, but the relationship is not linear (See, FIG. 13). While there is a significant change between 1, 3, and 5%, the variation between 5, 7 and 10% is minimal. This effect of diminishing benefit has been noted before with other hydrocarbon and fluorocarbon-in-water emulsions. The rate of ripening of a two-component disperse phase system is represented by the following equation:[18]

$$\omega_{mix} = (\phi_1/\omega_1 + \phi_2/\omega_2)^{-1} \quad (2)$$

where $\phi$ represents the volume fraction and the subscripts 1 and 2 refer to the more and less water-soluble components, respectively. As $\phi_2$ becomes larger, it becomes the dominant term until it solely controls the ripening rate.

Figure 14:
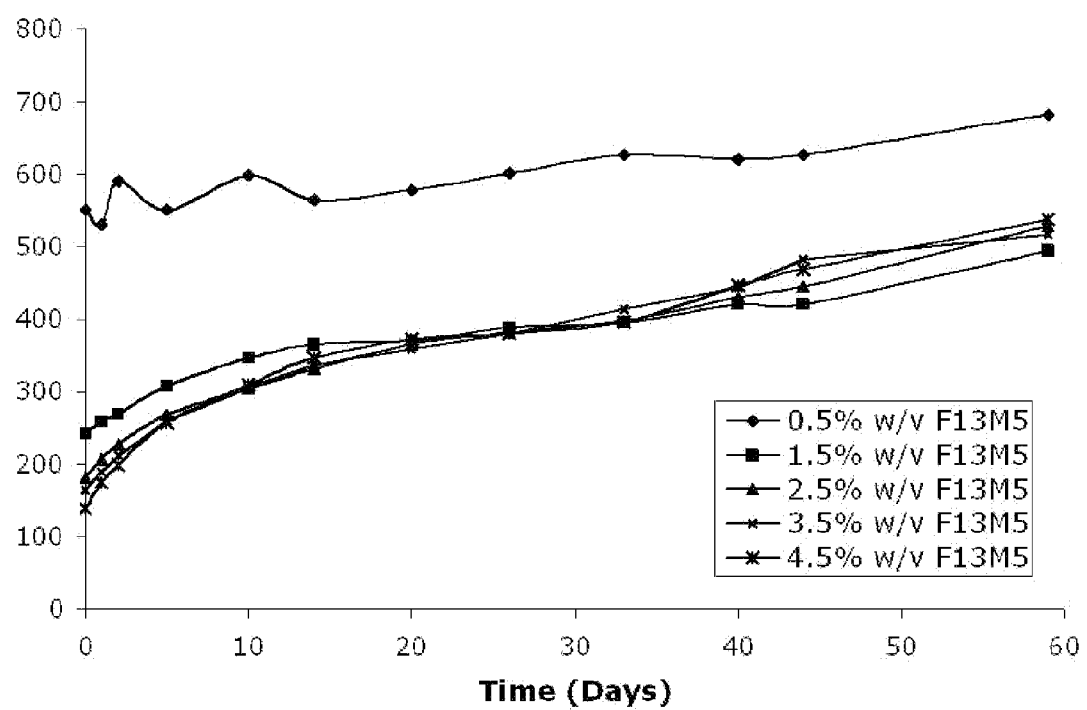
FIG. 14 provides a plot showing the effect of the amount of F13M5 polymer (% w/v on emulsion stability. All emulsions contained 20% v/v sevoflurane and 10% v/v perfluorooctyl bromide. Droplet diameter in nanometers is plotted (y-axis) versus time (days).
Figure 15:
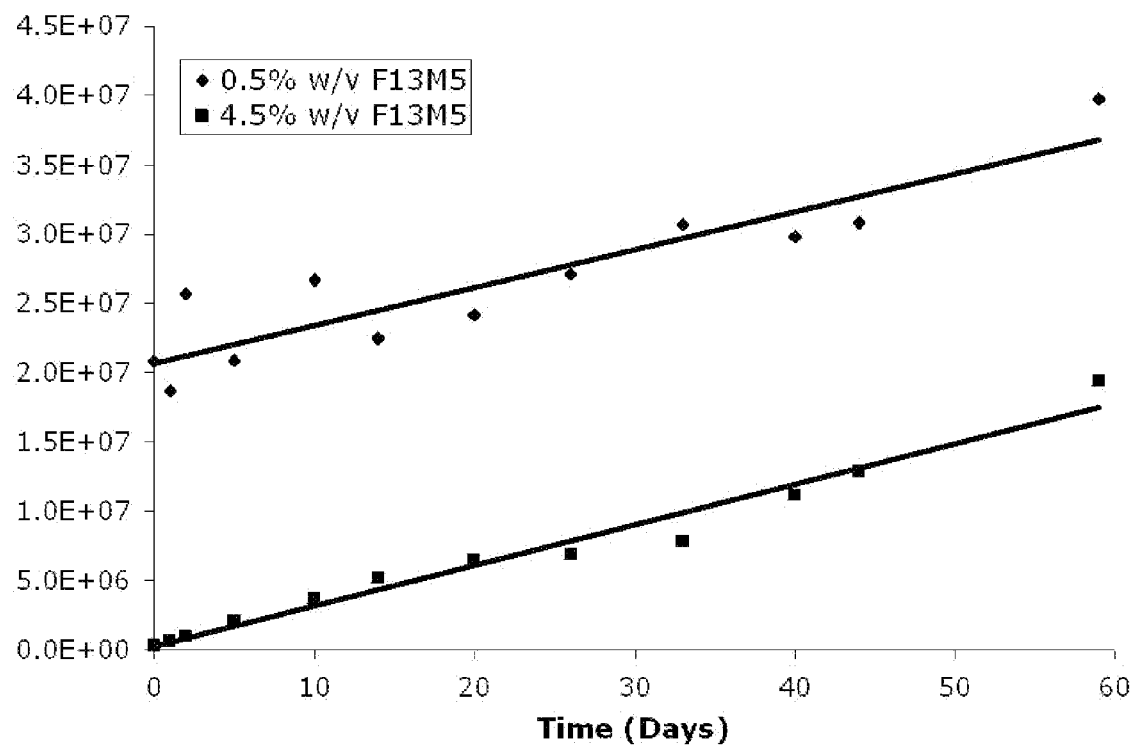
FIG. 15 provides a plot showing ripening with 0.5 and 4.5% w/v F13M5 replotted as the cube of the radius, with the linear best-fit line added.

Because the addition of perfluorooctyl bromide alone wasn't sufficient to completely stop ripening, measurements were taken with varying amounts of polymer and constant amounts of the other components. FIG. 14 shows the starting size and ripening rates for polymer amounts between 0.5-4.5% w/v. Mathematically, as the size of the average droplet decreases, the amount of total surface area increases, thus requiring more surfactant for complete coverage. At 0.5% w/v the significantly larger initial droplet size indicates that there was not enough available surfactant. An increase from 0.5 to 1.5% w/v polymer leads to a drop in the starting size from 550 to 241 nm. As expected, each subsequent polymer increase leads to a further reduction in the starting size (Table 1). Despite the changing initial size, however, the ripening rate is unaffected by different amounts of polymer. FIG. 15 shows the change in the cube of the radius for the graphs with the least (0.5% w/v) and greatest amount of polymer (4.5% w/v), with the others removed for clarity. In comparison of those two, the slope between the best-fit lines changes by only 6%, a statistically insignificant difference considering the nine-fold increase in polymer amount and inherent experimental error.

TABLE 1

Droplet starting size with varying polymer amount.
All emulsions contained 20% v/v sevoflurane
and 10% v/v perfluorooctyl bromide.

| Polymer Amount (% w/v) | Initial size (nm) |
|---|---|
| 0.5 | 550.6 |
| 1.5 | 241.5 |
| 2.5 | 181.5 |
| 3.5 | 163.9 |
| 4.5 | 139.3 |

The effect of polymer amount on emulsion stability can be studied by keeping the volume constant and varying the polymer amount, as above, or by keeping the polymer amount constant and varying the volume of emulsified oil. The latter was measured in emulsions of perfluorooctyl bromide alone, with the polymer fixed at 2.5% w/v, and the volume fraction of the oil varied between 10, 20 and 30% (See, FIG. 16). The actual droplet sizes over time, and therefore the rate of growth, are the same for all three volumes, suggesting that ripening has no dependence upon the volume fraction. It is clear, then, that in this system, excess surfactant, present in the form of micelles, has no effect on the ripening.

Figure 16:
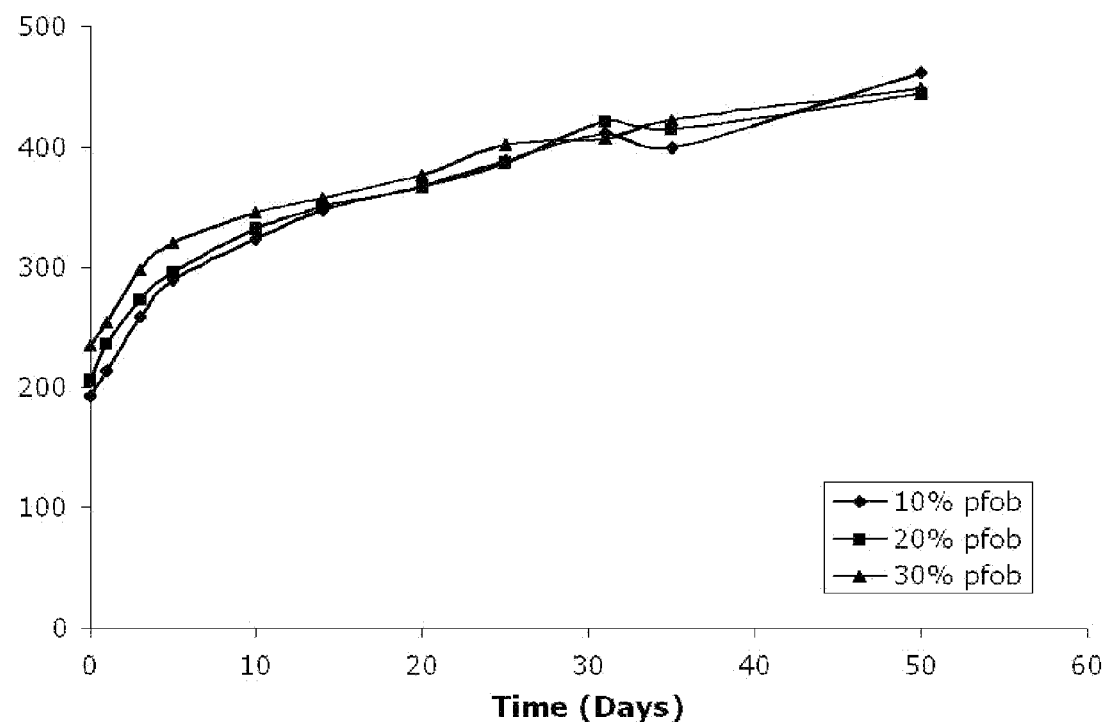
FIG. 16 provides a plot showing ripening with perfluorooctyl bromide as the sole emulsified oil. All emulsions were prepared with 2.5% w/v F13M5. Droplet diameter in nanometers is plotted (y-axis) versus time (days).
Figure 17:
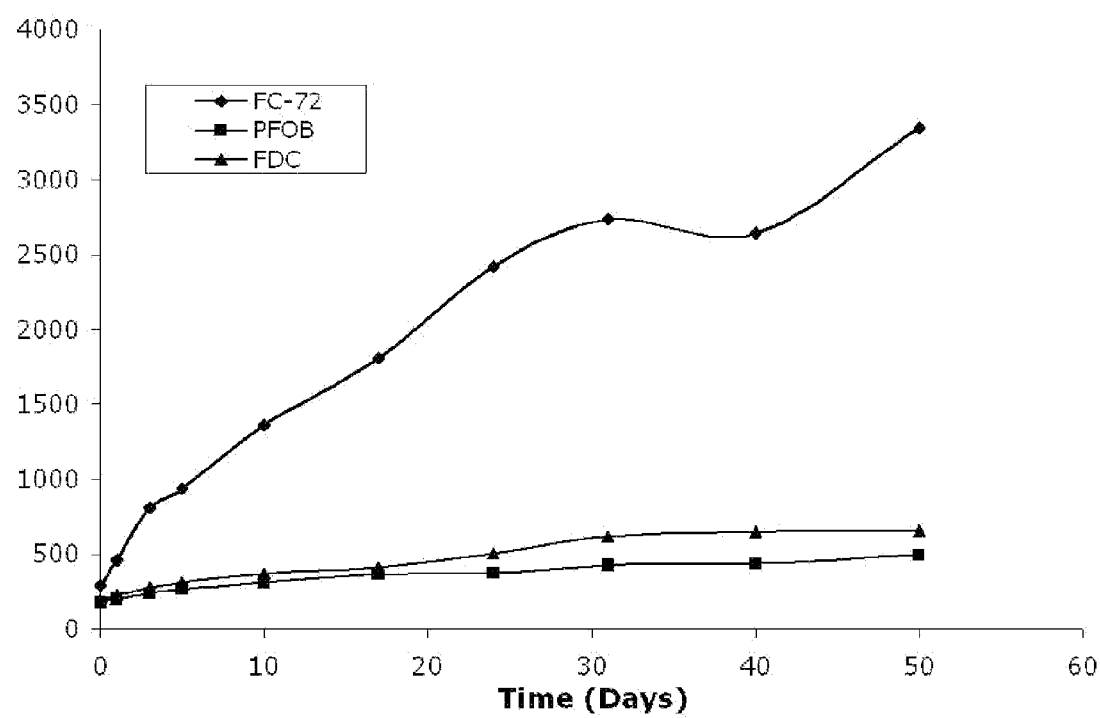
FIG. 17 provides a plot showing ripening rates with different stabilizing additives. All emulsions contained 20% v/v sevoflurane, 10% v/v stabilizing additive and 2.5% w/v. F13M5. Droplet diameter in nanometers is plotted (y-axis) versus time (days).

There have been contradictory reports within the literature regarding the effect of excess surfactant upon emulsion stability. In some instances the rate of ripening has increased as the amount of surfactant has increased, whether the excess surfactant is present in the form of vesicles or micelles. One of the justifications cited for such an effect is that the supramolecular aggregate (micelle or vesicle) provides a reservoir to solubilize excess oil, thus increasing the effective solubility of the oil in water. As can be seen in Eq. 1, as the solubility, $C_\infty$, increases, so too does the rate of ripening. However, a decrease in the ripening rate as the amount of surfactant increases has also been reported. In these cases, it has been proposed that the oil solubilized in the micelles is not dispersed in the continuous phase, and therefore is not subject to the same mass transfer between droplets. In this argument, $C_\infty$ is lowered as oil is withdrawn from the continuous phase into micelles, thus causing the ripening rate to decrease. An additional study showed that alkane emulsions stabilized by hexaethylene glycol dodecyl ether were unaffected by surfactant concentration. Our own results better agree with the conclusions of this latter study. As shown in FIGS. 15, 16 and 17, changes in the rate of ripening as the surfactant concentration increases are not statistically significant.

Although ripening was slowed by addition of the additive, it wasn't ever really prevented or significantly retarded. To confirm that the ripening was behaving classically, with a direct dependence upon water solubility, a comparison was made between different additives. All are highly fluorophilic, but differ in their water solubility. Perfluorohexanes (FC-72) has a water solubility of $2.7 \times 10^{-7}$ mol/L, perfluorooctyl bromide $5.1 \times 10^{-9}$ and perfluorodecalin $9.9 \times 10^{-9}$. FIG. 17 shows the comparison in ripening. As expected, FC-72, which is two orders of magnitude more water soluble, ripens much quicker. Perfluorodecalin and perfluorooctyl bromide, which have similar solubilities, also ripen similarly.

Figure 18:
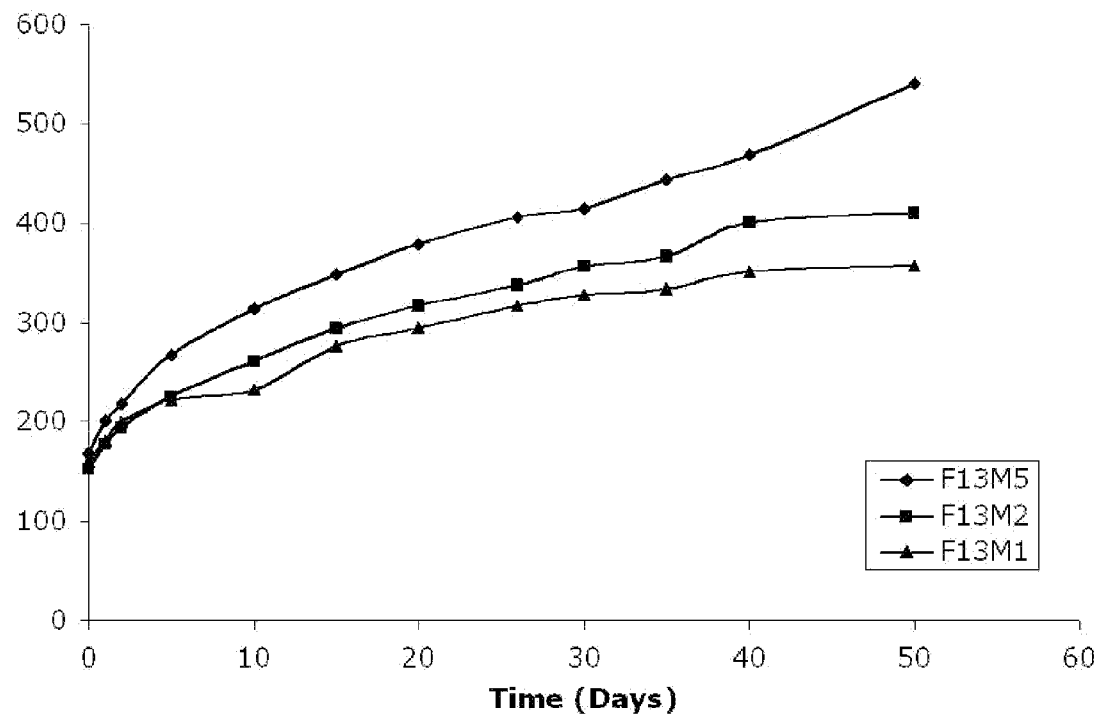
FIG. 18 provides a plot showing ripening rates for polymers with different PEG chain lengths. All emulsions contained 20% v/v sevoflurane, 10% v/v perfluorooctyl bromide and 2.5% w/v polymer. Droplet diameter in nanometers is plotted (y-axis) versus time (days).

Riess has previously shown that an F-alkylated derivative of trehalose was sufficient to slow the ripening of perfluorooctyl bromide to acceptable levels as the sole surfactant. However, maltose coupled to the same perfluorocarbon block was unable to emulsify perfluorooctyl bromide at all. These results show that the conformation of the polar head group can play a significant role in emulsion stability. Using that idea, the fluorocarbon block was kept the same and the PEG chain was shortened from 5000 to 2000 (F13M2), 1100 (F13M1) and 550 (F13M05). The F13M05 was significantly less water-soluble than the other polymers and further comparative study was not undertaken. FIG. 18 shows the ripening for the different polymers, with the component mixture kept the same. As the length of the PEG chain decreased, so too did the rate of ripening. This data, combined with the ripening for different polymer amounts (See, FIG. 14) suggests that while the steric bulk of each polymer is effective in preventing coalescence it also prevents sufficient amounts of polymer from tightly packing around each droplet. When there is less steric hindrance between each individual chain, as is presumably the case with F13M2 and F13M1, more polymer molecules can surround each droplet in a more dense, less penetrable polymeric monolayer and ripening is slowed.

Figure 19:
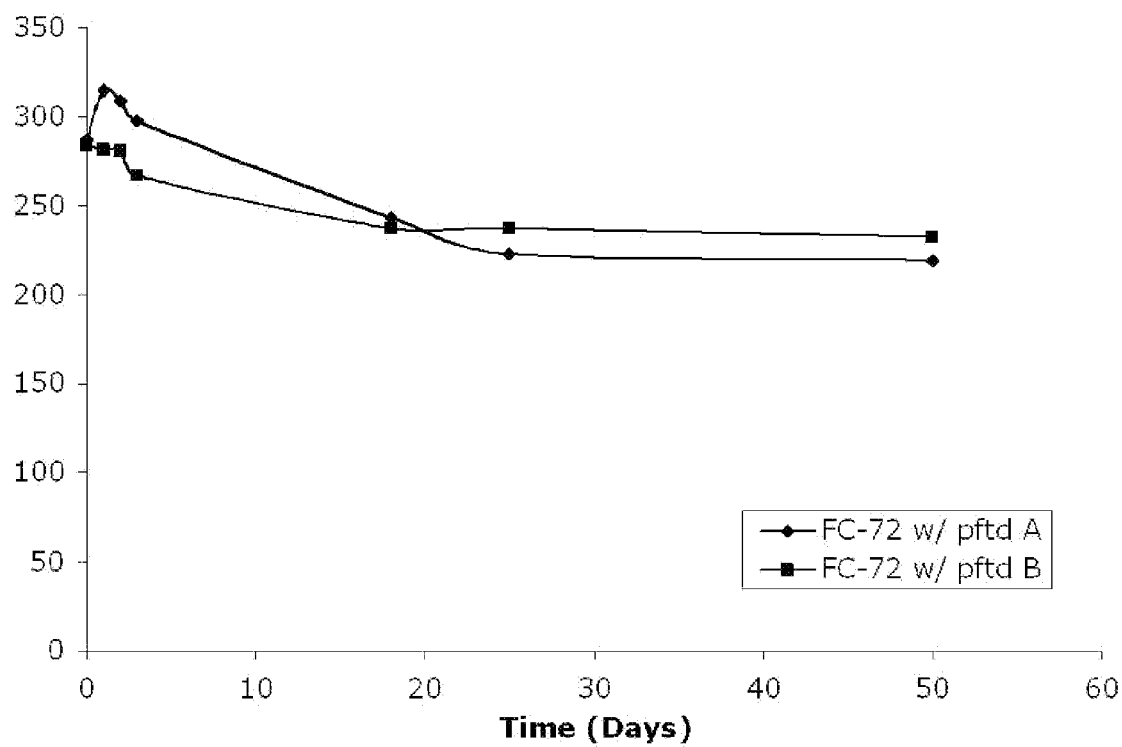
FIG. 19 provides a plot showing ripening rates with FC-72 as the primary oil and perfluorotridecane as the stabilizing additive. Both samples contained 20% v/v FC-72, 2% w/v perfluorotridecane and 1.5% w/v F13M5. Droplet diameter in nanometers is plotted (y-axis) versus time (days).
Figure 20:
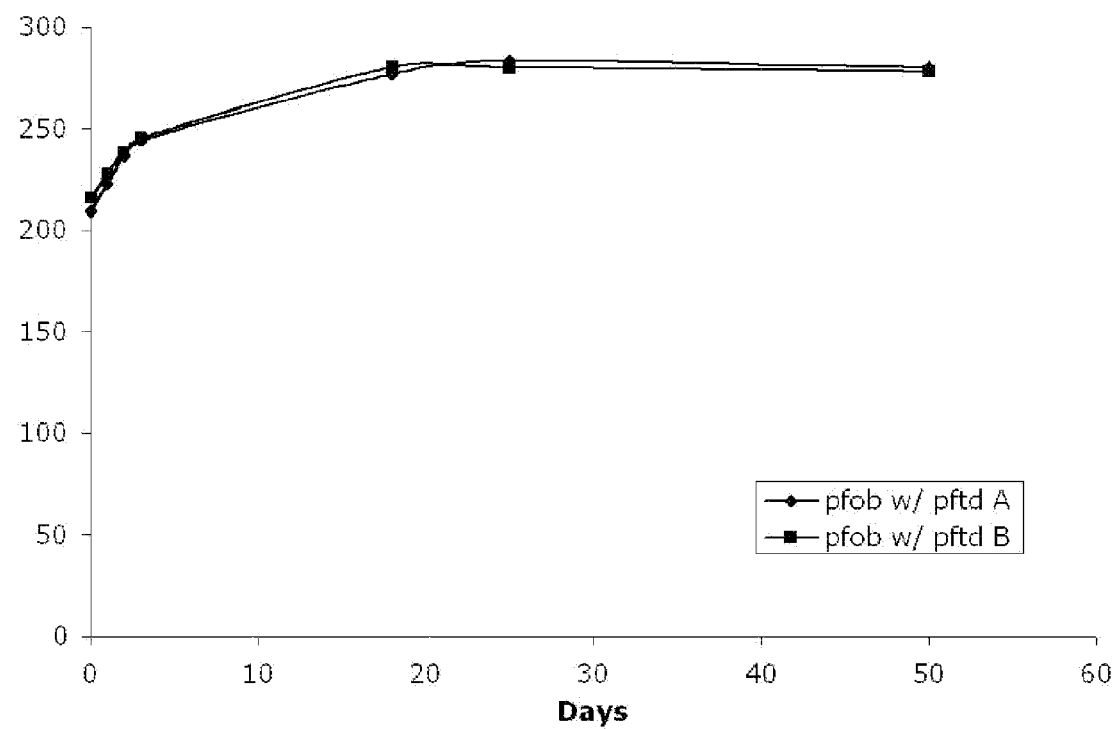
FIG. 20 provides a plot showing ripening rates with perfluorooctyl bromide as the primary oil and perfluorotridecane as the stabilizing additive. Both samples contained 20% v/v perfluorooctyl bromide, 2% w/v perfluorotridecane and 1.5% w/v F13M5. Droplet diameter in nanometers is plotted (y-axis) versus time (days).
Figure 21:
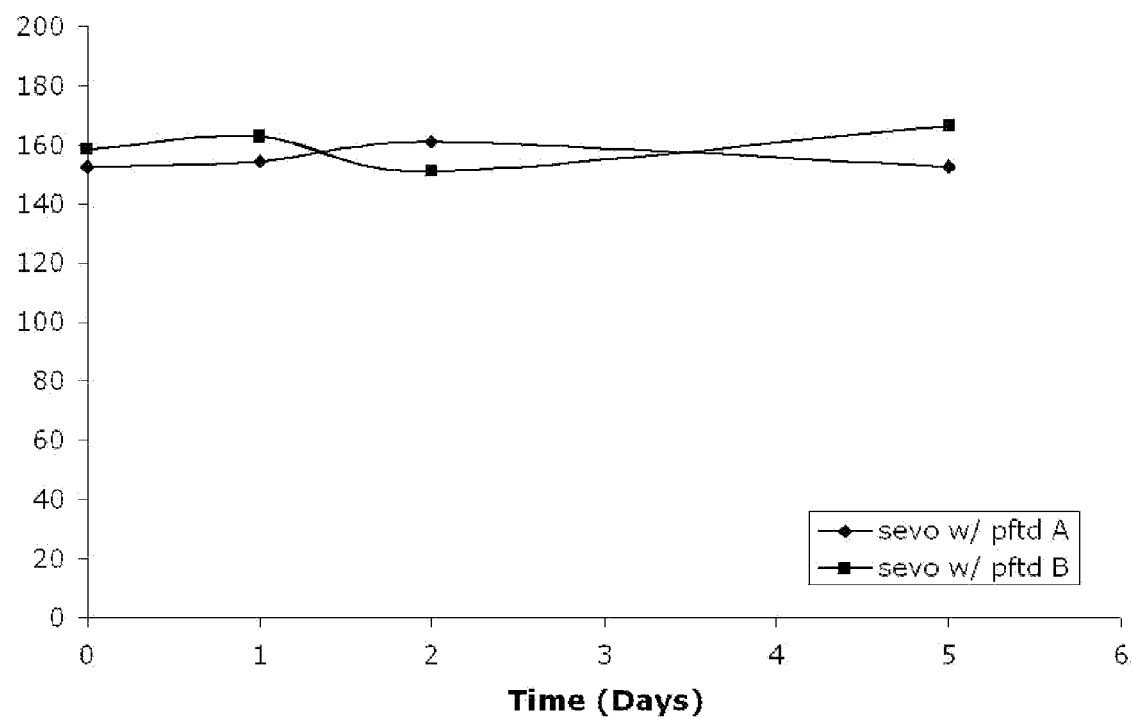
FIG. 21 provides a plot showing ripening rates with sevoflurane as the primary additive and perfluorotridecane as the additive. Both samples contained 20% v/v sevoflurane, 1.5% w/v perfluorotridecane and 1.5% w/v F13M5. Droplet diameter in nanometers is plotted (y-axis) versus time (days).

To determine if the design of the head group was allowing ripening or if ripening was exclusively mediated by the additive, a significantly less water-soluble additive, perfluorotridecane, n-$C_{13}F_{28}$, was studied. Though its high MW would lead to an unacceptably long residence time in the body, and thus preclude its use in any formulations intended for in vivo use, it was still useful as a probe to determine the physical properties of the emulsion. Three primary oils were investigated, FC-72, perfluorooctyl bromide and sevoflurane, all with perfluorotridecane as the additive. With both FC-72 (See, FIG. 19) and perfluorooctyl bromide (See, FIG. 20), after an initial equilibration time, the size stabilized and Ostwald ripening appeared to be stopped. With sevoflurane (See, FIG. 21) the results were even more promising as there was no initial equilibration and the size was constant from the beginning. Though the emulsion droplets had no change in size, at day 6 there was visual evidence of phase separation.

Figure 22:
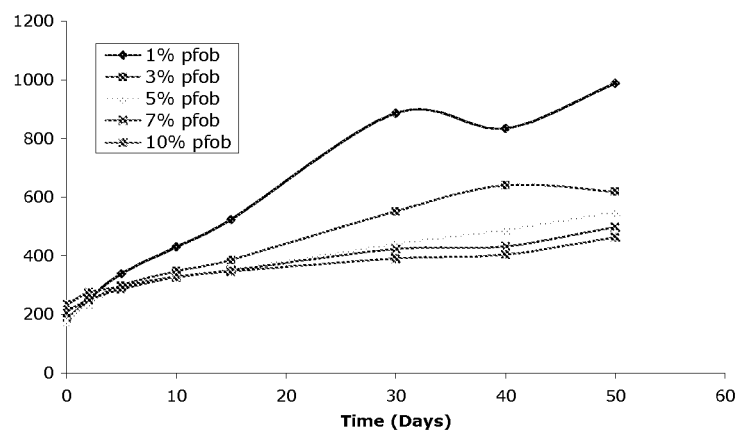
FIG. 22 provides plots showing ripening as function of the amount of stabilizing additive.
Figure 22:
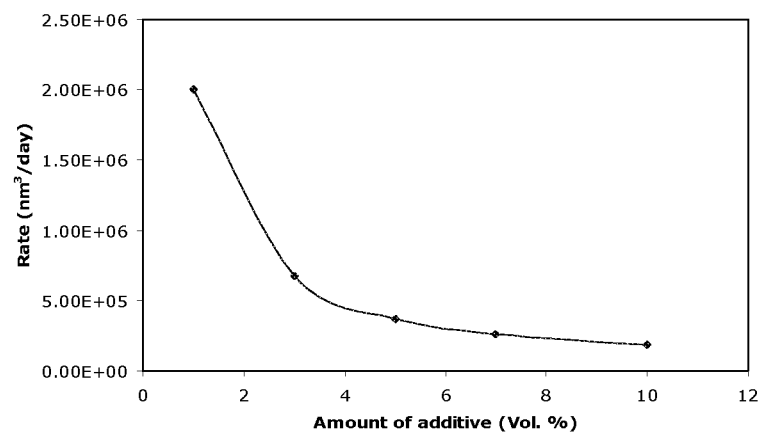

FIG. 22 provides plots showing ripening as function of the amount of stabilizing additive. FIG. 22A shows a plot of droplet diameter as a function of time for perfluorooctyl bromide (pfob) percentages by volume ranging from 1% to 10%. FIG. 22b shows a plot of ripening rate as a function of amount of additive. In these experiments the emulsions contain 20% by volume sevflurane and 1.5% weight by volume of the semifluorinated block copolymer surfactant F13M5.

As stated previously, coalescence is the only mechanism that can lead to phase separation and polymeric stabilizers are generally sufficient to prevent coalescence. Though sevoflurane with perfluorotridecane had the same polymeric stabilizer as the other emulsions studied, it was the only system to show coalescence. This suggests that the polymeric monolayer was modified, most likely by the intercalation of the perfluorotridecane between the perfluorocarbon blocks of F13M5. Then, if there were droplets that had a higher content of perfluorotridecane, it is possible that smaller amounts of F13M5 in the monolayer were insufficient to prevent coalescence. Interestingly, though some phase separation did happen after day 5, the sample never showed total phase separation, even after three months.

If intercalation of perfluorotridecane between the perfluorocarbon blocks of F13M5 is the reason that phase separation occurred with sevoflurane, the same effect might be expected to happen when perfluorotridecane is used as an additive to stabilize emulsions of either FC-72 and perfluorooctyl bromide. However, this is not the case as neither of the latter systems shows coalescence. The difference in emulsion stability is likely due to the different solubility of perfluorotridecane in the three fluorinated compounds. Perfluorotridecane is very miscible with both FC-72 and perfluorooctyl bromide, while the maximum solubility of perfluorotridecane in sevoflurane is only 78 mg/mL. It is likely that the limited solubility of perfluorotridecane in sevoflurane led to its preferential adsorption at the interface, rather than at the center of the droplet. The greater solubility of perfluorotridecane in the other solvents allowed it to more easily reside in the center of the droplet and act truly as a secondary oil additive.

Conclusions

A semi-fluorinated surfactant allowed the emulsification of considerable amounts of sevoflurane, up to 25% v/v, by exploiting the greater solubility of the anesthetic in a fluorous phase. This is a significant improvement over the maximum amount of sevoflurane that can be emulsified in classic lipid emulsions (Intralipid) and makes such formulations promising for potential clinical development. Though there was no any evidence of coalescence and ultimate phase separation, the sevoflurane/fluoropolymer emulsions were susceptible to Ostwald ripening. The addition of perfluorooctyl bromide as a secondary component did slow the ripening. It was demonstrated that both reduction of the size of the polar head group, as well as modification of the interfacial polymeric layer can lead to greater stability.

STATEMENTS REGARDING INCORPORATION BY REFERENCE AND VARIATIONS

All references throughout this application, for example patent documents including issued or granted patents or equivalents; patent application publications; unpublished patent applications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Separate embodiments of the invention are also intended to be encompassed wherein the terms "comprising" or "comprise(s)" or "comprised" are optionally replaced with the terms, analogous in grammar, e.g.; "consisting/consist(s)" or "consisting essentially of/consist(s) essentially of" to thereby describe further embodiments that are not necessarily coextensive.

The invention has been described with reference to various specific and preferred embodiments and techniques. However, it should be understood that many variations and modifications may be made while remaining within the spirit and scope of the invention. It will be apparent to one of ordinary skill in the art that compositions, methods, devices, device elements, materials, procedures and techniques other than those specifically described herein can be applied to the practice of the invention as broadly disclosed herein without resort to undue experimentation. All art-known functional equivalents of compositions, methods, devices, device elements, materials, procedures and techniques described herein are intended to be encompassed by this invention. Whenever a range is disclosed, all subranges and individual values are intended to be encompassed as if separately set forth. This invention is not to be limited by the embodiments disclosed, including any shown in the drawings or exemplified in the specification, which are given by way of example or illustration and not of limitation. The scope of the invention shall be limited only by the claims.

Pharmaceutically acceptable salts comprise pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl⁻, Br⁻), sulfate, acetates (e.g., acetate, trifluoroacetate), ascorbates, aspartates, benzoates, citrates, and lactate.

The compounds of this invention may contain one or more chiral centers. Accordingly, this invention is intended to include racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

REFERENCES

1. Eger, R. P.; Macleod, B. A. "Anaesthesia by Intravenous Emulsified Isoflurane in Mice" *Can. J. Anesth.* 1995, 42, 173-176.
2. Zhou, J.-X.; Luo, N.-F.; Liang, X.-M.; Liu, J. "The Efficacy and Safety of Intravenous Emulsified Isoflurane in Rats" *Anesth. Analg.* 2006, 102, 129-134.
3. Riess, J. G. "Fluorous Micro- and Nanophases with a Biomedical Perspective", *Tetrahedron* 2002, 58, 4113-4131.
4. Hoang, K. C.; Mecozzi, S. "Aqueous Solubilization of Highly Fluorinated Molecules by Semifluorinated Surfactants" *Langmuir* 2004, 20, 7347-7350.
5. a) Smart, B. E. "Characteristics of C—F Systems" in *Organofluorine Chemistry: Principles and Commercial Applications,* 57-88, Plenum Press, New York, 1994.
   b) Smart, B. E. "Fluorocarbons" *The Chemistry of Functional Groups, Supplement D,* 603-655 John Wiley & Sons, 1983.
6. Hudlicky, M.; Pavlath A. E.; Editors, *"Chemistry of Organic Fluorine Compounds II: a Critical Review", ACS Monograph No. 18"*. American Chemical Society, Washington, D.C., 1995.
7. Kissa, E. "Fluorinated Surfactants and Repellents", 2$^{nd}$ Ed. Surfactant Science Series, Vol. 97, Marcel Dekker, Inc. 2001.
8. Kobayashi, Y.; Yagupolskii L. M.; Editors, *"Organofluorine Compounds in Medicinal Chemistry and Biomedical Applications"* Studies in Organic Chemistry Vol. 48, Elsevier, 1993.
9. Eger, E. I. "Current and Future Perspectives on Inhaled Anesthetics" *Pharmacotherapy* 1998, 18, 895-910.
10. Holmgren, S. K.; Taylor, K. M.; Bretscher, L. E.; Raines, R. T. "A Hyperstable Collagen Mimic" *Nature.* 1998, 77, 666-667.
11. Holmgren, S. K.; Bretscher, L. E.; Taylor, K. M.; Raines, R. T. "Code for Collagen's Stability Deciphered" *Chem. Biol.* 1999, 6, 63-70.
12. Neil, E.; Marsh, G. "Towards the Nonstick Egg: Designing Fluorous Proteins" *Chem. & Biol.* 2000, 7, R153-R157.
13. Bilgicer, B.; Xing, X.; Kumar K. "Programmed Self-Sorting of Coiled Coils with Leucine and Hexafluoroleucine Cores" *J. Am. Chem. Soc.* 2001, 123, 11815-11816.
14. Bilgicer, B.; Kumar, K. "Synthesis and Thermodynamic Characterization of Self-Sorting Coiled Coils" *Tetrahedron.* 2002, 58, 4105-4112.
15. Tang, Y.; Ghirlanda, G.; Vaidehi, N.; Kua, J.; Mainz, D. T.; Goddard, W. A.; DeGrado, W. F.; Tirrell D. A. "Stabilization of Coiled-Coil Peptide Domains by Introduction of Trifluoroleucine." *Biochemistry* 2001, 40, 790-2796.
16. Xue, L.; DesMarteau, D. D.; Pennington, W. T.; "Perfectly Staggered and Twisted Difluoromethylene Groups in Perfluoroalkyl Chains: Structure of $M[C_4F_9SO_2NSO_2C_4F_9]$ (M=Na, K)" *Angew. Chem. Int. Ed. Engl.* 1997, 36, 1331-1333.
17. Martin, O.; Mecozzi, S. "Synthesis and Self-Assembly of Amphiphilic Semifluorinated Calix[4]arenes" *Supramol. Chem.* 2005, 17, 9-15.
18. Martin, M. O.; Yu, L.; Mecozzi, S. "Solution Self-Assembly and Solid-State Properties of Fluorinated Amphiphilic Calix[4]arenes. *Chem Comm* 2005, 4964-4966".
19. Martin, O.; Mecozzi, S. Synthesis and pH-Dependent Self-Assembly of Semifluorinated Calix[4]arenes. Submitted, 2006.
20. Krafft, M. P.; Riess, J. G. "Highly Fluorinated Amphiphiles and Colloidal Systems, and their Applications in the Biomedical Field. A Contribution" *Biochimie* 1998, 80, 489-514.
21. Krafft, M. P. "Fluorocarbons and Fluorinated Amphiphiles in Drug Delivery and Biomedical research" *Adv. Drug Del. Rev.* 2001, 47, 209-228.
22. Monduzzi, M. "Self-Assembly in Fluorocarbon Surfactant Systems" *Curr. Opin. Coll. Int. Sci.* 1998, 3, 467-477.
23. Schmutz, M.; Michels, B.; Marie, P.; Kraft, M. P. "Fluorinated Vesicles Made from Combinations of Phospholipids and Semifluorinated Alkanes. Direct Experimental Evidence of the location of Semifluorinated Alkane within the Bilayer" *Langmuir* 2003, 19, 4889-4894.
24. Zarif, L.; Gulik-Krzywicki, T.; Riess, J. G.; Pucci, B.; Guedj, C.; Pavia, A. "Alkyl and Perfluoroalkyl Glycolipid-Based Supramolecular Assemblies" *Coll. Surf. A* 1993, 84, 107-112.
25. Oda, R.; Huc, I.; Damino, D.; Talmon Y.; "Aggregation Properties and Mixing Behavior of Hydrocarbon, Fluorocarbon, and Hybrid Hydrocarbon-Fluorocarbon Cationic Dimeric Surfactants" *Langmuir* 2000, 16, 9759-9769.
26. Kraft, M. P.; Giulieri, F.; Riess, J. G "Supramolecular Assemblies from Single Chain Perfluoroalkylated Phosphorylated Amphiphiles" *Coll. Surf. A* 1994, 84, 113-119.
27. Messina, M. T.; Metrangolo, P.; Panzeri, W.; Ragg, E.; Resnati, G. "Perfluorocarbon-Hydrocarbon Self-Assembly. Part 3. Liquid Phase Interactions between perfluoroalkylhalides and heteroatom Containing Hydrocarbons" *Tetrahedron Lett.* 1998, 9069-9072.
28. Percec, V.; Bera, T. K. "Cell membrane as a Model for the Design of Semifluorinated Ion-Selective Nanostructured Supramolecular Systems" *Tetrahedron* 2002, 58, 4031-4040.
29. Riess, J. G. "Fluorous Materials for Biomedical Uses" in *Handbook of Fluorous Chemistry,* Wiley-VCH, 2004 521-573.
30. Kwon, G. S.; Naito, M.; Kataoka, K.; Yokoyama, M.; Sakurai, Y.; Okano, T. "Block Copolymer Micelles as Vehicles for Hydrophobic Drugs" *Colloids and Surfaces, B: Biointerfaces* 1994, 2, 429-34.
31. Torchilin, V. P. "Structure and Design of Polymeric Surfactant-Based Drug Delivery Systems" *J. Controlled Release* 2001, 73, 137-172.
32. Kwon, G. S. "Polymeric Micelles for Delivery of Poorly Water-Soluble Compounds" *Crit. Rev. Ther. Drug Carrier Syst.* 2003, 20, 357-403.
33. Adams, M. L.; Lavasanifar, A.; Kwon G. S. "Amphiphilic Block Copolymers for Drug Delivery" *J. Pharm. Sci.* 2003, 92, 1343-1355.
34. Rosier, A.; Vandermeulen, G. W.; Klok, H.-A. "Advanced Drug Delivery Devices Via Self-Assembly of Amphiphilic Block Copolymers". *Adv. Drug Del. Rev* 2001, 53, 95-108.
35. Jones, M.-C.; Leroux J.-C.; "Polymeric Micelles: A New Generation of Colloidal Drug Carriers" *Eur. J. Pharm. Biopharm.* 1999, 48, 101-111.
36. Burt, H. M.; Zhang, X.; Toleikis, P.; Embree, L.; Hunter, W. L. "Development of Copolymers of poly(D,L-lactide)

and Methoxypolyethylene Glycols as Micellar Carriers of Paclitaxel" *Coll. Suff. B Biointerfaces.* 1999, 16, 161-171.
37. Lavasanifar, A.; Samuel, J.; Kwon G. S. "Poly(ethylene oxide)-block-poly(L-amino acid) Micelles for Drug Delivery"". *Adv. Drug Del. Rev.* 2002, 54, 169-190.
38. Lavasanifar, A.; Samuel, J.; Kwon G. S. "The Effect of fatty Acid Substitution on the in vitro Release of Amphotericin B from Micelles Composed of poly(ethylene oxide)-block-poly(N-hexyl stearate-L-aspartamide" *J. Control Release.* 2003, 87, 23-32.
39. Chiari, P. C.; Pagel, P. S.; Tanaka, K.; Krolikowski, J. G.; Ludwig, L. M.; Trillo, R. A.; Puri, N.; Kersten, J. R.; Warltier, D. C. "Intravenous Emulsified Halogenated Anesthetics produce Acute and Delayed Preconditioning against Myocardial Infarction in Rabbits" *Anesthesiology* 2004, 101, 1160-1166.
40. Gelbart, W., M.; Ben-Shaul, A.; Roux, D., Editors, "Micelles, Membranes, Microemulsions, and Monolayers". Springer-Verlag, New York, 2004.
41. Riess, J. G. "Oxygen Carriers (Blood Substitutes)-Raison d'Etre, Chemistry and Some Physiology" *Chem. Rev.* 2001, 101, 2797-2919.
42. Ravey, J. C.; Gherbi, A.; Stebe, M. J. "Comparative Study of Fluorinated and Hydrogenated Nonionic Surfactants" *J. Phys. Chem.* 1988, 76, 234-241.
43. Kalyanasundaram, K.; Thomas, J. K. "Environmental Effects on Vibronic band Intensities in Pyrene Monomer Fluorescence and their Application in Studies of Micellar Systems" *J. Am. Chem. Soc.* 1976, 99, 2039-2044.
44. Dong, D. C.; Winnik, M. A. "The Py Scale of Solvent Polarities" *Can. J. Chem.* 1984, 62, 2560-2565.
45. Kalyanasundaram, K. Pyrene fluorescence as a probe of fluorocarbon micelles and their mixed micelles with hydrocarbon surfactants" *Langmuir* 1988, 4, 942-945.
46. Lavasanifar, A.; Samuel, J.; Kwon, G. S. "Micelles Self-Assembled from poly(ethylene oxide)-block-poly(N-hexyl stearate L-aspartamide) by a Solvent Evaporation Method Effect on the Solubilization and haemolytic Activity of Amphotericin B" *J. Control. Rel.* 2001, 77, 155-160.
47. Gladysz, J. A.; Curran D. P.; Horvath, I. T.; Editors, *Handbook of Fluorous Chemistry*, Wiley-VCH, 2004 521-573.
48. Franks, N. P.; Lieb W. R. "Molecular and Cellular Mechanisms of General Anaesthesia" *Nature* 1994, 367, 607-14.
49. Zimmerman, S. A.; Jones, M. V.; Harrison, N. L. "Potentiation of GABAA Receptor Cl⁻ Current Correlates with in Vivo Anesthetic Potency" *J. Pharmacol. Experim. Therap.* 1994, 270, 987-991.
50. Franks, N. P.; Lieb, W. R. "Temperature Dependence of the Potency of Volatile General Anesthetics: Implications for in Vitro Experiments" *Anesthesiology* 1996, 84, 716-720.
51. Wu, J.; Harata, N.; Akaike, N. "Potentiation by Sevoflurane of the γ-aminobutyric acid Induced Chloride Current in Acutely Dissociated CA1 Pyramidal Neurons from Rat Hippocampus" *Brit. J. Pharmacol* 1996, 119, 1013-21.
52. Krasowski, M. D.; Harrison, N. L. "The Actions of Ether, Alcohol and Alkane General Anaesthetics on GABA and Glycine Receptors and the Effects of TM2 and TM3 Mutations" *Brit. J. Pharmacol* 2000, 129, 731-743.
53. Hapfelmeier, G.; Schneck, H.; Kochs, E. "Sevoflurane Potentiates and Blocks GABA-Induced Currents through Recombinant alpha(1)ss(2)gamma(2) GABA(A) Receptors: Implications for an Enhanced GABAergic Transmission" *Eur. J. Anesthesology;* 2001, 18, 377-83.
54. Boileau, A. J.; Czajkowski, C. "Identification of Transduction Elements for Benzodiazepine Modulation of the GABA(A) Receptor: Three Residues are Required for Allosteric Coupling" *J. Neuroscience;* 1999, 19, 10213-10220.
55. Boileau, A. J.; Li, T.; Benkwitz, C.; Czajkowski, C. R. A. Pearce "Effects of Gamma2S Subunit Incorporation on GABAA Receptor Macroscopic Kinetics" *Neuropharmacol.* 2003, 44, 1003-12.
56. Chesney, M. A., Perouansky, M.; Pearce, R. A. "Differential uptake of volatile agents into brain tissue in vitro. Measurement and application of a diffusion model to determine concentration profiles in brain slices" *Anesthesiology* 2003, 99, 122-130.
57. Boileau, A. J.; Li, T.; Benwitz, C.; Czajkowski, C.; Pearce, R. A. "Effects of γ2S Subunit Incorporation on $GABA_A$ Receptor Macroscopic Kinetics" *Neuropharm.* 2003, 44, 1003-1012.
58. Benkwitz, C.; Banks, M. I.; Pearce, R. A. "Influence of $GABA_A$ Receptor γ2 Splice Variants on Receptor Kinetics and Isoflurane Modulation" *Anesthesiology* 2004, 101, 924-936.
59. Kennedy, G. L., Jr.; Butenhoff, J. L.; Olsen, G. W.; O'Connor, J. C.; Seacat, A. M.; Perkins, R. G.; Biegel, L. B.; Murphy, Sandra R.; Farrar, D. G. "The Toxicology of Perfluorooctanoate" *Crit. Rev. Tox.* 2004, 34, 351-384.
60. Lau, C.; Butenhoff, J. L.; Rogers, J. M. "The Developmental Toxicity of Perfluoroalkyl Acids and their Derivatives" *Tox. Appl. Pharm.* 2004, 198, 231-241.
61. Jones, P. D.; Newsted, J. L.; Giesy, J. P. "Toxicological Perspectives on Perfluorinated Compounds" *Organohalogen. Comp.* 2003, 62, 311-314.
62. Yu, K.; Toral-barza, L.; Dsicafani, C.; Zhang, W.-G.; Skotnicki, J.; Frost, P.; Gibbons, J. J. "mTOR, a Novel Target in Breast Cancer: the Effect of CCI-779, an mTOR Inhibitor, in Preclinical Models of Breast Cancer" *Endocrine-Related Cancer* 2001, 8, 249-258.

We claim:
1. A therapeutic formulation comprising:
an aqueous solution;
semi-fluorinated block copolymers having a hydrophilic block and a fluorophilic block, wherein said fluorophilic block is a perfluorinated linear alkyl chain having a length of 6 to 16 carbons, and wherein said hydrophilic block is a poly(ethylene glycol) block having a molecular weight selected over the range of 500 g mol$^{-1}$ to 5,000 g mol$^{-1}$;
a fluorinated anesthetic compound selected from the group consisting of sevoflurane, isoflurane, desflurane, enflurane and methoxyflurane; and
a stabilizing additive comprising a perhalogenated fluorocarbon selected from the group consisting of perfluorooctyl bromide and perfluorodecalin;
wherein said formulation is a nanoemulsion comprising a continuous phase and a dispersed phase, wherein said continuous phase comprises said aqueous solution and said dispersed phase comprises said semi-fluorinated block copolymers, said fluorinated anesthetic compound and said stabilizing additive; and
wherein said fluorinated anesthetic compound is greater than or equal to 5% by volume of said therapeutic formulation, said perhalogenated fluorocarbon is 1% to 20% by volume of said therapeutic formulation; and said semi-fluorinated block copolymers have a concentration selected over the range of 1 mg ml$^{-1}$ to 45 mg ml$^{-1}$.

2. The therapeutic formulation of claim 1 wherein said semi-fluorinated block copolymers have the chemical formula:

$$C_mF_{2m+1}\text{-}L_1\text{-}(\text{---}CH_2CH_2\text{---}O\text{---})_n\text{---}R; \quad (FX1)$$

wherein m is selected from the range of 6 to 16;
n is selected from the range of 12 to 113,
$L_1$ is a linking group; and
wherein R is a hydrogen, a methyl group, a substituted or unsubstituted alkoxy group, a substituted or unsubstituted alkyl group, a substituted or unsubstituted aryl group, a substituted or unsubstituted alkenyl; or a substituted or unsubstituted alkynyl group.

3. The therapeutic formulation of claim 2 wherein said linking group ($L_1$) is a $C_{1-10}$ alkyl group.

4. The therapeutic formulation of claim 1 wherein said semi-fluorinated block copolymers have the chemical formula:

$$C_mF_{2m+1}\text{-}(CH_2)_p\text{---}O\text{---}(\text{---}CH_2CH_2\text{---}O\text{---})_n\text{---}R; \text{ or} \quad (FX2)$$

$$C_mF_{2m+1}\text{---}O\text{---}(\text{---}CH_2CH_2\text{---}O\text{---})_n\text{---}R; \quad (FX3)$$

wherein m is selected from the range of 6 to 16;
n is selected from the range of 12 to 113;
p is selected from the range 1 to 10; and
wherein R is a hydrogen, a methyl group, a substituted or unsubstituted alkoxy group, a substituted or unsubstituted alkyl group, a substituted or unsubstituted aryl group, a substituted or unsubstituted alkenyl; or a substituted or unsubstituted alkynyl group.

5. The therapeutic formulation of claim 1 wherein said perhalogenated fluorocarbon stabilizing additive has a solubility in water less than or equal to 20 nanomolar.

6. The therapeutic formulation of claim 1 further comprising one or more additional fluorocarbon stabilizing additives.

7. The therapeutic formulation of claim 1 wherein the fluorinated anesthetic compound is 5% to 30% by volume of said therapeutic formulation.

8. The therapeutic formulation of claim 1 wherein said dispersed phase comprises a plurality of droplets dispersed in said continuous phase.

9. The therapeutic formulation of claim 8 wherein said droplets have an average diameter less than or equal to 1000 nanometers.

10. The therapeutic formulation of claim 8 wherein said droplets have an average diameter less than or equal to 400 nanometers.

11. The therapeutic formulation of claim 8 wherein said droplets dispersed in said continuous phase comprise self assembled supramolecular structures.

12. The therapeutic formulation of claim 11 wherein said supramolecular structures comprise an interior fluorous core of said fluorinated anesthetic compound; wherein said interior fluorous core comprises droplets of fluorinated anesthetic compound encapsulated by said semi-fluorinated block copolymers.

13. The therapeutic formulation of claim 12 wherein said fluorophilic block of said semi-fluorinated block copolymers is oriented proximate to said interior fluorous core of said particles; and wherein said hydrophilic block is oriented distal to said interior fluorous core of said particles.

14. The therapeutic formulation of claim 12 wherein said droplets of fluorinated anesthetic compound have an average diameter ranging from 100 nm to 1 micron.

15. The therapeutic formulation of claim 1 wherein said fluorinated anesthetic compound is 5% to 50% by volume of said therapeutic emulsion.

16. The therapeutic formulation of claim 1 wherein said fluorinated anesthetic compound is greater than 5% by volume of said therapeutic emulsion.

17. The therapeutic formulation of claim 1 wherein said therapeutic emulsion is for administration to a patient via intraveneous injection.

18. A method of administering a fluorinated anesthetic compound to a patient, said method comprising the steps of:
providing a therapeutic formulation comprising:
an aqueous solution;
semi-fluorinated block copolymers having a hydrophilic block and a fluorophilic block, wherein said fluorophilic block is a perfluorinated linear alkyl chain having a length of 6 to 16 carbons, and wherein said hydrophilic block is a poly(ethylene glycol) block having a molecular weight selected over the range of 500 g mol$^{-1}$ to 5,000 g mol$^{-1}$;
a fluorinated anesthetic compound selected from the group consisting of sevoflurane, isoflurane, desflurane, enflurane and methoxyflurane; and
a stabilizing additive comprising a perhalogenated fluorocarbon selected from the group consisting of perfluorooctyl bromide and perfluorodecalin;
emulsifying said therapeutic formulation, thereby making a therapeutic nanoemulsion comprising a continuous phase and a dispersed phase, wherein said continuous phase comprises said aqueous solution and said dispersed phase comprises said semi-fluorinated block copolymers, said fluorinated anesthetic compound and said stabilizing additive;
delivering said therapeutic nanoemulsion to said patient; and
wherein said fluorinated anesthetic compound is greater than or equal to 5% by volume of said therapeutic formulation, said perhalogenated fluorocarbon is 1% to 20% by volume of said therapeutic formulation; and said semi-fluorinated block copolymers have a concentration selected over the range of 1 mg ml$^{-1}$ to 45 mg ml$^{-1}$.

19. The method of claim 18 wherein said therapeutic nanoemulsion is delivered to said patient via intravenous injection.

20. The method of claim 18 wherein a volume of therapeutic nanoemulsion selected over the range of 1 ml to 100 ml is delivered to said patient.

21. The method of claim 18 wherein said therapeutic nanoemulsion is delivered to said patient at a rate selected over the range of 0.1 ml min$^{-1}$ to 20 ml min$^{-1}$.

22. The method of claim 18 wherein said step of emulsifying said therapeutic formulation comprises the steps of:
adding said fluorinated anesthetic compound and said stabilizing additive to said aqueous solution having said semi-fluorinated block copolymers therein, thereby generating a therapeutic mixture; and
homogenizing said therapeutic mixture, thereby generating said therapeutic nanoemulsion.

23. The method of claim 22 further comprising the step of lowering the temperature of said therapeutic mixture during said step of homogenizing said therapeutic mixture.

24. The method of claim 23 wherein said step of homogenizing said therapeutic mixture is carried out using a lower energy mixer, a microfluidizer or both a lower energy mixer and microfluidizer.

25. The method of claim 18 wherein the fluorinated anesthetic compound is 5% to 30% by volume of said therapeutic formulation.

26. The method of claim 18 wherein said fluorinated anesthetic compound is greater than 5% by volume of said therapeutic emulsion.

27. A method of making a therapeutic nanoemulsion containing a fluorinated anesthetic compound, said method comprising the steps of:
providing a therapeutic formulation comprising:
an aqueous solution;
semi-fluorinated block copolymers having a hydrophilic block and a fluorophilic block, wherein said fluorophilic block is a perfluorinated linear alkyl chain having a length of 6 to 16 carbons, and wherein said hydrophilic block is a poly(ethylene glycol) block having a molecular weight selected over the range of 500 g mol$^{-1}$ to 5,000 g mol$^{-1}$;
a fluorinated anesthetic compound selected from the group consisting of sevoflurane, isoflurane, desflurane, enflurane and methoxyflurane;
and a perhalogenated fluorocarbon stabilizing additive selected from the group consisting of: perfluorooctyl bromide and perfluorodecalin;
emulsifying said therapeutic formulation, thereby making said therapeutic nanoemulsion comprising a continuous phase and a dispersed phase, wherein said continuous phase comprises said aqueous solution and said dispersed phase comprises said semi-fluorinated block copolymers, said fluorinated anesthetic compound and said fluorocarbon stabilizing additive; and
wherein said fluorinated anesthetic compound is greater than or equal to 5% by volume of said therapeutic formulation, said perhalogenated fluorocarbon is 1% to 20% by volume of said therapeutic formulation; and said semi-fluorinated block copolymers have a concentration selected over the range of 1 mg ml$^{-1}$ to 45 mg ml$^{-1}$.

28. The method of claim 27 wherein said step of emulsifying said therapeutic formulation comprises the steps of:
adding said fluorinated anesthetic compound and said perhalogenated fluorocarbon stabilizing additive to said aqueous solution having said semi-fluorinated block copolymers therein, thereby generating a therapeutic mixture; and
homogenizing said therapeutic mixture, thereby generating said therapeutic nanoemulsion.

29. The method of claim 28 further comprising the step of lowering the temperature of said therapeutic mixture during said step of homogenizing said therapeutic mixture.

30. The method of claim 28 wherein said step of homogenizing said therapeutic mixture is carried out using a lower energy mixer, a microfluidizer or both a lower energy mixer and microfluidizer.

31. A method of stabilizing a therapeutic emulsion containing a fluorinated anesthetic compound, said method comprising the steps of:
providing a therapeutic formulation comprising: an aqueous solution;
semi-fluorinated block copolymers having a hydrophilic block and a fluorophilic block;
and the fluorinated anesthetic compound, wherein said fluorophilic block is a perfluorinated alkyl chain having a length of 6 to 16 carbons, and wherein said hydrophilic block is a poly(ethylene glycol) block having a molecular weight selected over the range of 500 g mol$^{-1}$ to 5,000 g mol$^{-1}$;
adding a perhalogenated fluorocarbon stabilizing additive selected from the group consisting of perfluorooctyl bromide and perfluorodecalin to said therapeutic formulation;
emulsifying said therapeutic formulation to generate a nanoemulsion comprising a continuous phase and a dispersed phase, wherein said continuous phase comprises said aqueous solution and said dispersed phase comprises said semi-fluorinated block copolymers, said fluorinated anesthetic compound and said stabilizing additive, thereby stabilizing said therapeutic emulsion; and
wherein said fluorinated anesthetic compound is selected from the group consisting of sevoflurane, isoflurane, desflurane, enflurane and methoxyflurane and is greater than or equal to 5% by volume of said therapeutic formulation, said perhalogenated fluorocarbon is 1% to 20% by volume of said therapeutic formulation; and said semi-fluorinated block copolymers have a concentration selected over the range of 1 mg ml$^{-1}$ to 45 mg ml$^{-1}$.

* * * * *